(12) United States Patent
Helmerhorst et al.

(10) Patent No.: US 6,933,272 B1
(45) Date of Patent: Aug. 23, 2005

(54) USE OF NON-PEPTIDYL COMPOUNDS FOR THE TREATMENT OF INSULIN RELATED AILMENTS

(76) Inventors: Erik Helmerhorst, 5 Selsted Place, Glendalough (AU); Brian Scott Plewright, 253 Grand Promenade, Doubleview (AU)

(*) Notice: Subject to any disclaimer, the term of this patent is extended or adjusted under 35 U.S.C. 154(b) by 0 days.

(21) Appl. No.: 09/400,769

(22) Filed: Sep. 22, 1999

Related U.S. Application Data

(60) Provisional application No. 60/101,339, filed on Sep. 22, 1998.

(51) Int. Cl.[7] .............................................. A01N 37/18
(52) U.S. Cl. ..................... 514/2; 514/2; 514/3; 514/12; 514/13; 514/14; 514/21; 530/350; 530/323; 530/324; 530/325; 530/326; 530/327; 424/464
(58) Field of Search ................................ 530/350, 326, 530/323, 325, 327, 324; 514/2, 3, 12, 13, 14, 21; 424/464

(56) References Cited

U.S. PATENT DOCUMENTS

| | | | |
|---|---|---|---|
| 4,871,739 A | 10/1989 | Baldwin et al. | 514/254 |
| 4,992,418 A | 2/1991 | Katsoyannis et al. | 514/3 |
| 5,008,241 A | 4/1991 | Markussen et al. | 514/3 |
| 5,149,777 A | 9/1992 | Hansen et al. | 530/303 |
| 5,175,145 A | 12/1992 | Cooper | 514/4 |
| 5,227,466 A | 7/1993 | DeMeyts | 530/305 |
| 5,514,646 A | 5/1996 | Chance et al. | 514/3 |
| 5,599,841 A | 2/1997 | Meglasson | 514/557 |
| 5,618,913 A | 4/1997 | Brange et al. | 530/303 |
| 5,629,319 A | 5/1997 | Luo et al. | 514/284 |
| 5,641,796 A | 6/1997 | Dominianni et al. | 514/374 |
| 5,652,221 A | 7/1997 | Larner et al. | 514/35 |
| 5,656,722 A | 8/1997 | Dorschug | 530/303 |
| 5,661,168 A | 8/1997 | Panetta et al. | 514/369 |
| 5,674,900 A | 10/1997 | Ubillas et al. | 514/557 |
| 5,686,411 A | 11/1997 | Gaeta et al. | 514/12 |
| 5,691,386 A | 11/1997 | Inman et al. | 514/691 |
| 5,693,609 A | 12/1997 | Baker et al. | 514/3 |
| 5,698,669 A | 12/1997 | Hoffmann et al. | 530/303 |
| 5,716,927 A | 2/1998 | Balschmidt et al. | 514/3 |
| 5,716,975 A | 2/1998 | Bue-Valleskey et al. | 514/369 |
| 5,817,684 A | 10/1998 | Fleisch et al. | |
| 5,851,988 A * | 12/1998 | Sportman et al. | 514/4 |
| 6,329,431 B1 * | 12/2001 | Sportman et al. | 514/598 |

FOREIGN PATENT DOCUMENTS

| | | | |
|---|---|---|---|
| AU | A 54495/86 | 9/1986 | |
| AU | A 62066/86 | 3/1987 | |
| EP | 0 325 224 B1 | 7/1989 | ............ C12N/15/12 |
| EP | 0 433 225 A1 | 6/1991 | ............ C07K/7/10 |
| EP | 0 618 227 A1 | 10/1994 | ............ C07K/15/00 |
| EP | 0 132 366 A2 | 1/1995 | |
| FR | 2 037 002 A | 12/1970 | |
| JP | 1 305097 | 12/1989 | ......... C07H/17/065 |
| WO | WO 88/06599 | 9/1988 | |
| WO | WO 90/01038 | 2/1990 | |
| WO | WO 90/07522 | 7/1990 | |
| WO | WO 90/12814 | 11/1990 | |
| WO | WO 90 15816 A | 12/1990 | |
| WO | WO 95/17183 | 6/1995 | |
| WO | WO 96/13613 | 5/1996 | ............ C12Q/1/68 |
| WO | WO 97/27847 | 8/1997 | ......... A61K/31/095 |
| WO | WO 97/40017 | 10/1997 | ......... C07D/231/00 |

OTHER PUBLICATIONS

Journal of the Japan Diabetes Society, vol. 42, No. 6, p. 461–465, 1999, Azami et al.*
Ganong, 1989 Review of Medical Physiology, 1989.*
Bajaj et al., *Biochem. J.*, 238:345–351 (1986) "Coypu insulin—Primary structure, conformation and biological properties of a hystricomorph rodent insulin".
Bao et al., *Proc. Nat'l Acad. Sci. (USA)*, 94:2975–2980 (Apr. 1997) "Crystal structure of desheptapeptide (B24–B30)insulin at 1.6 Å resolution: Implications for receptor binding".
Blundell et al., *Biochem. J.,125(3)*:50P–51P (Dec. 1971) "The Structure and Biology of Insulin".
Blundell et al.,*Proc. Nat'l. Acad. Sci. (USA)*, 75(1):180–184 (Jan. 1978) "Insulin–like growth factor: A model for tertiary structure accounting for immunoreactivity and receptor binding".
Blundell et al., *Advances in Protein Chemistry: 26, XII+ 431P.*, Academic Press: New York, NY USA, London, England, pp. 279–403 (1972) "Insulin: The Structure in the Crystal and its Reflection in Chemistry and Biology".
Chu et al., *Biochemistry 26:*6966–6971 (1987) "Possible Involvement of the $A^{20}$–$A^{21}$ Peptide Bond in the Expression of the Biological Activity of Insulin. 1. [21–Desasparagine, 20–cysteinamide–A]insulin and [21–Desasparagine, 20–cysteine isopropylamide–A]Insulin".
Chu et al., *Biochemistry, 26:*6972–6979 (1987) "Possible Involvement of the $A^{20}$–$A^{21}$ Peptide Bond in the Expression of the Biological Activity of Insulin. 2. [21–Asparagine diethylamide–A]insulin".
Chu et al., *Biochemistry, 26:*6975–6979 (1987) "Possible Involvement of the $A^{20}$–$A^{21}$ Peptide Bond in the Expression of the Biological Activity of Insulin. 3. [21–Desasparagine, 20–cyteine ethylamide–A]insulin and [21–Desasparagine, 20–cysteine 2–,2,2–trifluoroethylamide–a]insulin".
Corin et al., *J. Biol. Chem., 257(1)*:104–110 (Jan. 10, 1982) "Insulin Receptors Convert to a Higher Affinity State Subsequent to Hormone Binding—A Two–State Model for the Insulin Receptor".

(Continued)

Primary Examiner—Jon Weber
Assistant Examiner—Hope A. Robinson
(74) Attorney, Agent, or Firm—Marshall, Gerstein & Borun LLP

(57) ABSTRACT

The present invention relates to the use of at least a non-peptidyl compound as a biological modulator of insulin activity or insulin-related activity, which compound possesses ionic and hydrophobic chemical moieties spatially located so as to mimic at least an ionic and hydrophobic amino acid residue of insulin, which amino acids are associated with the binding of insulin to its receptor.

34 Claims, 35 Drawing Sheets

OTHER PUBLICATIONS

De Meyts et al., *Biochem. Biophys. Res. Comm.*, 55(*1*): 154–161 (1973) "Insulin Interactions With Its Receptors: Experimental Evidence For Negative Cooperativity".

De Meyts, *Bull. Mem. Acad. R. Med. Belg.*, 149(*3–4*):181–194 (1994) Abstract Only in English "Insulin receptors and mechanism of action of insulin and of insulin-like growth factors".

Djuric et al., *J. Med. Chem.*, 32(*6*):1145–1147 (Jun. 1989) "Communications to the Editor".

Donner, *Proc. Nat'l. Acad. Sci. (USA)*, 77(*6*):3176–3180 (Jun. 1980) "Regulation of insulin binding to isolated hepatocytes: Correction of bound hormone fragments linearizes Scatchard plots".

Donner et al., *J. Biol. Chem.*, 258(*15*):9413–9418 (1983) "Hormone–induced Conformational Changes in the Hepatic Insulin Receptor".

Easter et al., *Hoppe–Seylers A. Physiol. Bd.*, *359*:S.229–1236 (Sep. 1978) "Crystalline [A21–Desamido] Bovine Insulin".

Ferderigos et al., *Int. J. Peptide Protein Res.*, *13*:43–53 (1979) "[21—Arginine—A]Insulin: A Biologically Active Analog".

Gammeltoft, *Physiol. Rev.*, 64(*4*):1321–1379 (Oct. 1984) "Insulin Receptors:Binding Kinetics and Structure–Function Relationship of Insulin".

Gapinski et al., *J. Med. Chem.*, *33*:2807–2813 (1990) "Benzophenone Dicarboxylic Acid Antagonists of Leukotriene $B_4$. 2. Structure–Activity Relationships of the Lipophilic Side Chain".

Garrett et al., *Nature*, *394*:395–399 (Jul. 23, 1998) "Crystal structure of the first three domains of the type–1 insulin –like growth factor receptor".

Gattner et al., *Hoppe–Seyler's Z. Physiol. Chem. Bd.*, *358*:S.105–112 (Jan. 1977) "[A21–Asparaginimide] Insulin—Saponification of Insulin Hexamethyl Ester, I".

Hammond et al., *Am. J. Physiol*, 272(*6*):1136–1144 (1997) "An Evaluation of the cross–linking model for insulin–receptor interactions".

Harmon et al., *J. Biol. Chem.*, 258(*11*):6875–6881 (Jun. 10, 1983) "Characterization of a Membrane Regulator of Insulin Receptor Affinity".

Harper et al., *J. Med. Chem.*, *37*:2411–2420 (1994) "Leukotriene $B_4$ ($LTB_4$) Receptor Antagonists: A Series of (Hydroxyphenyl)pyrazoles".

Helmerhorst, *Biochem. Biophys. Res. Commun.*, 147(*1*) 399–407 (Aug. 31, 1987) "The Insulin–Receptor Interaction: Is The Kinetic Approach For Inferring Negative–Cooperative Site–Site Interactions Valid?".

Helmerhorst et al., *Biochem.*, 32(*9*):2356–2362 (1993) "Insulin Binding to Rat Liver Membranes Predicts a Homogeneous Class of Binding Sites in Different Affinity States That May Be Related to a Regulator of Insulin Binding".

Hua et al., *Biochem.*, *30*:5505–5515 (1991) "Comparative 2D–NMR Studies of Human Insulin and Des–pentapeptide Insulin: Sequential Resonance Assignment and Implications for Protein Dynamics and Receptor Recognition".

Hua et al., *Nature*, *354*:238–240 (Nov. 21, 1991) "Receptor binding redefined by a structural switch in a mutant human insulin".

Hua et al., *Biochem.*, *31*:11940–11951 (1992) "Nonlocal Structural Perturbations in a Mutant Human Insulin Sequential Resonance Assignment and $^{13}C$–Isotope–Aided 2D–NMR Studies of [PheB24–Gly]Insulin with Implications for Receptor Recognition".

Hua et al., *Biochem.*, *32*:1433–1442 (1993) "Dynamics of a Monomeric Insulin Analogue: Testing the Molten–Globule Hypothesis".

Hubbard et al., *Nature*, *372*:746–755 (Dec. 22/29, 1994) "Crystal structure of the tyrosine kinase domain of the human insulin receptor".

Hubbard, *EMBO J.*, 16(*18*):5572–5581 (1997) "Crystal structure of the activated insulin receptor tyrosine kinase in complex with peptide substrate and ATP analog".

Isakoff et al., *Proc. Nat'l. Acad. Sci. (USA)*, *92*:10247–10251 (Oct. 1995) "The inability of phosphatidylinositol 3–kinase activation to stimulate GLUT4 translocation indicates additional signaling pathways are required for insulin–stimulated glucose uptake".

Jackson et al., *J. Med. Chem.*, *36*:1726–1734 (1993) "Design, Synthesis, and Pharmacological Evalution of Potent Xantone Dicarboxylic Acid Leukotriene $B_4$ Receptor Antagonists".

Kahn et al., *J. Biol. Chem.*, 249(*7*):2249–2257 (Apr. 10, 1974) "Quantitative Aspects of the Insulin–Receptor Interaction in Liver Plasma Membranes".

Knegtel et al., *J. Biochem.*, *202*:447–458 (1991) "The solution structure of a monomeric insulin; A two–dimensional $^1H$–NMR study of des–(B26–B30)–insulin in combination with distance geometry and restrained molecular dynamics".

Kohanski et al., *J. Biol. Chem.*, 258(*11*):5014–5025 (Apr. 25, 1985) "Homogeneous Functional Insulin Receptor from 3T3–L1 Adipocytes".

Konstantopoulos, Thesis Paper present to The University of Melbourne (Jan. 1997) "Involvement of Insulin and its Receptor in Cell–Matrix Interactions".

Kristensen et al., *J. Biol. Chem.*, 272(*20*):12978–12983 (May 16, 1997) "Alanine Scanning Mutagenesis of Insulin".

Li et al., *J. Biol. Chem.*, 266(*11*):7051–7057 (1991) "Insulin Receptors Prepared with Iodoacetamide Show Enhanced Autophosphorylation and Receptor Kinase Activity".

Liang et al., *Science in China (Series B)*, 35(*5*):547–557 (May 4, 1991) "The Possible Mechanism of Binding Interaction of Insulin Molecule Binding With Its Receptor".

Luo et al., *Science*, *285*:1077–1080 (Aug. 13, 1999) "Quaternary Structure of the Insulin–Insulin Receptor Complex".

Maturo III et al., *Proc. Nat'l. Acad. Sci. (USA)*, 75(*7*):3070–7074 (Jul. 1978) "Insulin receptor: Interaction with nonreceptor glycoprotein from liver cell membranes".

Maturo et al., *Chem. Pharmacology*, 37(*19*):3755–3760 (1988) "Taurine Binding to the Purified Insulin Receptor".

Mirmira et al., *J. Biol. Chem.*, 264(*11*):6349–6354 (Apr. 15, 1989) "Role of the Phenylalanine B24 Side Chain in Directing Insulin Interaction with Its Receptor".

Mirmira et al., *J. Biol. Chem.* 266(*3*):1428–1436 (1991) "Importance of the Character and Configuration of Residues B24, B25, and B26 in Insulin–Receptor Interactions".

Mirmira et al., *Biochemistry*, 30(*33*):8222–8229 (1991) "Disposition of the Phenylalanine B25 Side Chain during Insulin–Receptor and Insulin–Insulin Interactions".

Mortensen et al., *Biochem. J.* *281*:735–743 (1992) "Guanosine Nucleotides regulate hormone binding of insulin receptors".

Murray–Rust et al., *BioEssays, 14*(5):325–331 (May 1992) "Structure and Evolution of Insulins: Implications for Receptor Binding".

Nakagawa et al., *J. Biol. Chem., 262*(25):12054–12058 (Sep. 1987) "Role of the COOH–terminal B–chain Domain in Insulin–Receptor Interactions".

Nakagawa et al., *J. Biol. Chem., 261*(16):7332–7341 (Jun. 5, 1986) "Role of the Phenylalanine B25 Side Chain in Directing Insulin Interaction with Its Receptor".

Nakagawa et al., *Biochemistry, 31*:3204–3214 (1992) "Importance of Aliphatic Side–Chain Structure at Positions 2 and 3 of the Insulin Chain in Insulin–Receptor Interactions".

Peterson et al., *J. Biol. Chem., 250*:5183–5190 (1975) "The amino Acid Sequence of the Insulin from a Primitive Vertebrate, the Atlantic Hagfish (*Myxine glutionosa*)".

Pollet et al., *J. Biol. Chem., 252*(16):5828–5834 Aug. 25, 1977) "Insulin Binding to the Human Lymphocyte Receptor".

Pullen et al., *Nature, 259*:369–373 (Feb. 5, 1976) "Receptor–binding region of insulin".

Saunders, *Diabetologia, 23*:386–390 (1982) "A New Interpretation of Structure–Function Relationships in Insulin–Receptor Interactions".

Sawyer et al., *J. Med. Chem., 36*:3982–3984 (1993) "Biohenylyl–Substituted Xanthones: Highly Potent Leukotriene $B_4$ Receptor Antagonists".

Schaffer, *Eur. J. Biochem., 221*:1127–1132 (1994) "A model for insulin binding to the insulin receptor".

Sørensen et al., *Biochemistry, 33*:13727–13733 (1994) "Structural Details of Asp(B9) Human Insulin at Low pH from Two–Dimensional NMR Titation Studies".

Soos et al., *Proc. Nat'l. Acad. Sci. (USA),86*:5217–5221 (Jul. 1989) "Monoclonal antibodies to the insulin receptor mimic metabolic effects of insulin but do not stimulate receptor autophosphorylation in transfected NIH 3T3 fibroblasts".

Steele–Perkins et al., *J. Biol. Chem., 265*(16):9458–5464 (1990) "Insulin–mimetic Anti–insulin Receptor Monoclonal Antibodies Stimulate Receptor Kinase Activity in Intact Cells".

Varma et al., *Biochem. Mol. Biol. Internat'l., 32*(5):807–817 (Apr. 1994) "Association of $G_{(B)}$, A Novel 66kDa GTP–Binding Placental Protein, with Insulin Receptor".

Weiss et al, *Biochemistry, 28*:9855–9873 (1989) "Two–Dimensional NMR and Photo–CIDNP Studies of the Insulin Monomer:Assignment of Aromatic Resonances with Application to Protein Folding, Structure, and Dynamics".

Weitzel et al., *Hoppe–Seyler's Z. Physiol. Chem. Bd., 359*:S 945–958 (Aug. 1978) "Structure and Activity of Insulin, XVI$^{[1-6]}$, Semisyntheses of Desheptapeptide–(B24–30)–up fo Destripeptide (B28–30)–Insulin with Lysine or Alanine in Place of Arginine in Position B22: Influence on the Three–Step–Increase of Activity in Positions B24–26 (Phe–Phe–Tyr)".

Wood et al., *Eur. J. Biochem., 55*:531–542 (1975) "The Relation of Conformation and Association of Insulin to Receptor Binding; X–Ray and Circular–Dichroism Studies on Bovine and Hystricomorph Insulins".

Yip, *J. Cellular Biochem., 48*.19–25 (1992) "The Insulin–Binding Domain of Insulin Receptor Is Encoded by Exon 2 and Exon 3".

Zhang et al., *Biochem. Molec. Biol. Internat'l., 36*(5):1079–1085 (Aug. 1995) "Recombinant A17 LYS Human Insulin:Purification and Characterization".

PCT International Search Report—International Application No. PCT/AU 99/00786.

Aguilar–Bryan e t al., Chemical Abstracts, Abstract No.: 490788 (1990) Photoaffinity labelling and partial purification of the beta cell sulfonylurea receptor using a novel, biologically active glyburide analog., *J. Biol. Chem. 265*(14):8218–24 (1990).

Bahn et al., Chemical Abstracts, Abstract No.: 42678 (1980) Cystic Acids as a solubilizing protective group in peptide chemistry, *Schriftenr Dtsch Wollforschungsinst, 76*:5–7 (1978).

Aubert, "Antidiabétiques oraux: les biguandes," *Sciences Medicales* 10(47): 31–32 (1980). (French).

Klijn, et al., "Growth factor–receptor pathway interfering treatment by somatostatin analogs and suramin: preclinical and clinical studies," *J. Steroid Biochemistry and Molecular Biology, 37*(6): 1089–1095 (Dec. 1990).

Lundquist, "Islet lysosomal enzyme activities and plasma insulin levels in obese hyperglycemic mice following injection of the lysosomotropic drug suramin," *Diabetes Research 2*: 207–211 (1985).

"A new salt of metformin proposed in the oral treatment of diabetes: embonate (or pamoate) of metformin," *Journées Annuelles de Diabetologie de L'Hotel–Dieu*: 382–385 (1977). (French).

Setyono–Han et al., "Suramin: Pharmokinetic Monitoring, Haematological and Antitumor Effects of Rats bearing Transplantable Pancreatic Tumors," *Eur. J. Cancer 26*(2): 184 (1990).

\* cited by examiner

| Hypothesis | Residue | | | | | | | | | | |
|---|---|---|---|---|---|---|---|---|---|---|---|
| | A21 | B21 | A17 | B24 | B25 | A19 | B12 | B16 | A1 | A2 | A3 |
| 1 | □ | □ | □ | □ | □ | | | | | | |
| 2 (1a) | □ | □ | | □ | □ | | | | | | |
| 3 | □ | □ | | □ | □ | | | | □ | □ | □ |
| 4 | □ | □ | □ | | | □ | | | □ | □ | □ |
| 5 | □ | □ | □ | | | | □ | | □ | □ | □ |
| 5a | | | | | | | □ | | □ | □ | □ |
| 6 | □ | □ | □ | | | | | □ | □ | □ | □ |
| 7 | □ | □ | □ | | | □ | □ | □ | | | |
| 7a | □ | □ | | | | □ | □ | □ | | | |
| 8 | □ | □ | □ | □ | □ | □ | □ | □ | | | |
| 8a | □ | □ | | □ | □ | □ | □ | □ | | | |
| 8d | □ | □ | | □ | □ | | □ | □ | | | |
| 9 | □ | □ | □ | □ | □ | □ | | | | | |
| 9a | □ | □ | | □ | □ | □ | | | | | |
| 9b | □ | | □ | □ | □ | □ | | | | | |
| 9e | | □ | □ | □ | □ | □ | | | | | |
| 10 | □ | □ | □ | □ | □ | | □ | | | | |
| 10a | □ | □ | | □ | □ | | □ | | | | |
| 10b | □ | | □ | □ | □ | | □ | | | | |
| 10e | | □ | □ | □ | □ | | □ | | | | |
| 11 | □ | □ | □ | □ | □ | | | □ | | | |
| 11a | □ | □ | | □ | □ | | | □ | | | |
| 11b | □ | | □ | □ | □ | | | □ | | | |
| 11e | | □ | □ | □ | □ | | | □ | | | |
| 12 | □ | □ | □ | □ | | | □ | □ | □ | | |
| 12a | □ | □ | | □ | | | □ | □ | □ | | |
| 12b | □ | | □ | □ | | | □ | □ | □ | | |
| 12e | | □ | □ | □ | | | □ | □ | □ | | |
| 13 | □ | □ | □ | | □ | | □ | □ | □ | | |
| 13a | □ | □ | | | □ | | □ | □ | □ | | |
| 13b | □ | | □ | | □ | | □ | □ | □ | | |
| 13e | | □ | □ | | □ | | □ | □ | | | |

Figure 2

| Residue | Feature | Tolerance HIU Å | Tolerance HIT3 Å | Tolerance HIT4 Å |
|---|---|---|---|---|
| A17 COO$^-$ | Negative ionisable | 5 | 3 | 3 |
| A21 COO$^-$ | Negative ionisable | 5 | 3 | 3 |
| B21 COO$^-$ | Negative ionisable | 5 | 3 | 3 |
| B24 Phe | Hydrophobic | 5 | 3 | 3 |
| B25 Phe | Hydrophobic | 5 | 3 | 3 |
| A 1 NH$_3^+$ | Positive ionisable | 5 | 3 | 3 |
| A2 Ile | Hydrophobic | 5 | 3 | 3 |
| A3 Val | Hydrophobic | 3 | 3 | 3 |
| A19 Tyr | Hydrophobic | 3.6 | 3 | 3 |
| B16 Tyr | Hydrophobic | 3.6 | 3 | 3 |
| B12 Val | Hydrophobic | 3.6 | 3 | 3 |

Figure 3

| Hypothesis | Tolerance | | | |
|---|---|---|---|---|
| | 1.5Å | 2Å | 3Å | 5Å |
| 1 | | ☐ | ☐ | ☐ |
| 2 (1a) | ☐ | ☐ | ☐ | ☐ |
| 3 | | | | |
| 4 | | | | |
| 5 | | | | |
| 5a | | | | |
| 6 | | | | |
| 7 | | | ☐ | ☐ |
| 7a | | | ☐ | ☐ |
| 8 | | | | ☐ |
| 8a | | | | ☐ |
| 8d | | | ☐ | ☐ |
| 9 | | | ☐ | ☐ |
| 9a | | ☐ | ☐ | ☐ |
| 9b | | ☐ | ☐ | ☐ |
| 9e | | ☐ | ☐ | ☐ |
| 10 | | | ☐ | ☐ |
| 10a | | ☐ | ☐ | ☐ |
| 10b | | ☐ | ☐ | ☐ |
| 10e | | ☐ | ☐ | ☐ |
| 11 | | | ☐ | ☐ |
| 11a | | ☐ | ☐ | ☐ |
| 11b | | | ☐ | ☐ |
| 11e | | ☐ | ☐ | ☐ |
| 12 | | | ☐ | |
| 12a | | | ☐ | ☐ |
| 12b | | | ☐ | ☐ |
| 12e | | | ☐ | ☐ |
| 13 | | | | ☐ |
| 13a | | | | ☐ |
| 13b | | | | ☐ |
| 13e | | | | ☐ |

Figure 4

USE OF NON-PEPTIDYL COMPOUNDS FOR THE TREATMENT OF INSULIN RELATED AILMENTS

CROSS REFERENCE OF THE INVENTIONS

This application claims the benefit of U.S. Provisional Application No. 60/101,339 filed Sep. 22, 1998, the disclosure of which is hereby incorporated herein by reference.

FIELD OF THE INVENTION

The present invention relates to the use of one or more non-peptidyl compounds for the treatment of a patient suffering from one or more insulin related ailments.

BACKGROUND ART

General

Those skilled in the art will appreciate that the invention described herein is susceptible to variations and modifications other than those specifically described. It is to be understood that the invention includes all such variation and modifications. The invention also includes all of the steps, features, compositions and compounds referred to or indicated in the specification, individually or collectively, and any and all combinations or any two or more of the steps or features.

The present invention is not to be limited in scope by the specific embodiments described herein, which are intended for the purpose of exemplification only. Functionally equivalent products, compositions and methods are clearly within the scope of the invention as described herein.

Bibliographic details of the publications numerically referred to in this specification are collected at the end of the description. All references cited, including patents or patent applications are hereby incorporated by reference. No admission is made that any of the references constitute prior art.

As used herein the term "derived from" shall be taken to indicate that a specific integer may be obtained from a particular source albeit not necessarily directly from that source.

Throughout this specification and the claims which follow, unless the context requires otherwise, the word "comprise", or variations such as "comprises" or "comprising", will be understood to imply the inclusion of a stated integer or group of integers but not the exclusion of any other integer or group of integers.

Scientific

It is generally accepted that agents such as hormones and growth factors elicit their biological functions by binding to specific recognition sites, or receptors, in the plasma membranes of their target cells. This typically causes a conformational change in the receptor, and triggers secondary cellular responses which may result in the activation or inhibition of intracellular processes. Such agents are often referred to as biological modifiers. They may be categorised into two classes according to their activity. Agents which have a stimulatory activity are termed agonists, and those which inhibit the effect of the original ligand are termed antagonists.

The discovery of biological modifiers that differ in structure from the original ligand may be medically useful. Such compounds may have slightly different spectra of biological activity, allowing them to be used in very specific situations. Compounds that are chemically simpler than the agent which they mimic are potentially produced in greater quantities and at lower costs. Compounds that are more chemically robust than the original ligand may be administered by more convenient means. For example, peptidyl ligands cannot be taken orally as they will be broken down in the digestive tract, whereas a non-peptidyl agonist may potentially be administered by this route.

Insulin is a peptidyl ligand, and the identification of agonists and antagonists thereof has important pharmaceutical applications in the treatment of insulin related ailments.

Insulin is regarded as the most important regulatory hormone involved in maintaining glucose homeostasis. In vivo, insulin is produced in the pancreatic $\beta$-cells of the Islets of Langerhans. It is secreted from these cells in response to a wide range of nutrients, hormones and neurotransmitters. However, glucose is considered the most important regulator of insulin release. Following its release insulin is carried systemically to target tissues such as liver, muscle and fat. It promotes the uptake of glucose in the peripheral tissues and inhibits gluconeogenesis in the liver. Insulin also is involved in: promoting the synthesis of glycogen, lipid, and protein; gene transcription and mRNA turnover, and the transport of specific amino acids and ions.

Insulin works by first binding to the insulin receptor on the cell surface of its target tissues. The insulin receptor is a specific transmembrane glycoprotein composed of two $\alpha$-subunits and two $\beta$-subunits linked by disulfide bonds. The $\alpha$-subunits are located extracellularly and contain the insulin binding domain. The $\beta$-subunits of the receptor pass through the plasma membrane and have an intrinsic tyrosine kinase activity associated with their intracellular domain. The X-ray coordinates of part of the tyrosine kinase domain has been resolved (1, 2), however, the coordinates detailing the structure of the $\alpha$-subunits are not yet available. Some inferences about the structure of some domains of the $\alpha$-subunit can be made from fibronectin structures of homologous protein domains resolved by NMR spectroscopy and from the X-ray structure of the closely related IGF-1 receptor (3). Most recently, the general quaternary structure of the insulin receptor has been resolved using electron cryomicroscopy (4). These studies indicate that one insulin molecule probably binds and effectively crosslinks a L1-cysteine rich domain of one $\alpha$-subunit and the L2 domain of the other $\alpha$-subunit. This viewpoint is supported by models derived from the complex kinetics of insulin binding and the models of receptor oligomerisation described below. Following insulin binding to the $\alpha$-subunit, the $\beta$-subunit is autophosphorylated on specific tyrosine residues and this promotes the tyrosine kinase activity of the receptor.

The interaction of insulin with its receptor leading to receptor activation is a complex, key initial event in insulin action. The kinetics of insulin binding to its receptor have been discussed in a plethora of literature over the past twenty years and many different models have been proposed to explain the interaction. Much debate still exists over which of these proposed models effectively describes the correct binding kinetics.

The simplest model proposes that the insulin receptor population is characterised by a single class of homogeneous, non-interacting binding sites and that insulin action is directly proportional to the fraction of these receptors that are occupied. Other studies confirm a single class of receptors, with reported dissociation constants in the order of 0.5 to 5 nM, depending on the source of insulin receptors and experimental conditions employed (eg. temperature).

An alternate model is based on studies that report curvilinear Scatchard plots and assume multiple classes of binding sites. R. Kahn et al. (5) propose two specific receptor sites; a high affinity-low capacity site and a low affinity-high capacity site. However, in a recent review, B. J. Hammond et al. (6), question the validity of this and suggest that because these two binding sites exist on each receptor, there is no logical reason why they would possess different affinities or more importantly widely differing concentrations.

Another model explaining the non-linear nature of Scatchard plots assumes negative cooperativity. P. De Meyts et al. (7), suggest that the filling of empty receptor sites by unlabelled insulin increases the dissociation of labelled insulin from other sites, leading to curvilinear Scatchard plots. This was interpreted as resulting from site-site interactions. However, E. Helmerhorst (8) demonstrates that insulin enhances its own dissociation even when binding is characterised by linear Scatchard plots. Additionally, R. Pollet et al. (9) recognise that the dissociation rate of insulin is nearly independent of receptor occupancy, with enhanced dissociation of bound $^{125}I$ insulin by native insulin occurring in certain conditions where binding occupancy is decreased. D. Donner (10) also question the theory of negative cooperativity because correction for insulin degradation products result in linear Scatchard plots, suggesting that heterogeneous distribution of binding may in fact be due to insulin degradation rather than negative cooperative interactions.

Another two-state model, proposed by R. Corin and D. Donner (11) explains the kinetics observed upon insulin/receptor dissociation and is illustrated below:

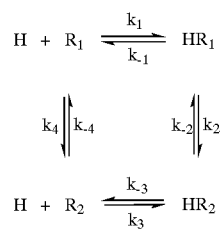

The hormone (H) interacts with the receptor ($R_1$) to result in the formation of a complex ($HR_1$), with subsequent rapid dissociation ($k_{-1}$). Stabilisation of the complex ($HR_1$) is through conversion ($k_2$) to another state, from which hormone dissociation is slow ($k_{-2}$). R. Corin and D. Donner (11) postulate that increasing occupancy time favours the formation of the second complex at the expense of the first. Thus, this model supports the kinetic data that identifies a constant association rate, but a dissociation rate which decreases with time. As a result of a decreased dissociation rate, the dissociation constant is also reduced, therefore providing an explanation for the presence of receptors of two apparent different affinities. It is not known if the bound complex $HR_2$ may dissociate directly to H and $R_2$ through $k_{-3}$ and to $R_1$ through $k_{-4}$.

A study by E. Helmerhorst and C. Yip (12) support this two-state model, with the binding of insulin to rat liver membranes producing Scatchard plots of both a linear and curvilinear nature. Insulin binding to rat liver membranes at temperatures of 4 to 15° C. is characterised by linear Scatchard plots, while higher temperatures result in plots that are distinctly curvilinear. E. Helmerhorst and C. Yip (12) implicate a single class of homogeneous, non-interacting binding sites of low affinity below 15° C. However, at physiological temperatures, two receptor states exist. In reference to the model of R. Corin and D. Donner (11), this suggests that insulin receptors exist primarily in one state at temperatures below 15 degrees, where $R_1 > R_2$ and $k_4$ is less than $k_{-4}$. However, as the temperature increases, these values become more similar, leading to increased $R_2$, and a curvilinear Scatchard plot.

Several models are based on the original suggestion of D. B. Donner and K. Yonkers (13), that insulin binding induces a conformational change in its receptor, with a conversion to a more slowly dissociating complex. P. De Meyts (14) and L. Schaffer (15) models are consistent with this notion where the initial binding of insulin to one α-subunit of the insulin receptor is followed by the cross-linking of insulin to a second α-subunit.

Briefly, the model proposes that insulin contains two binding surfaces on each α-subunit which can interact independently with corresponding surfaces on another α-subunit of the receptor. These binding sites, termed α1 and α2, have differing affinities with α1 having a higher affinity than the α2 region. If insulin binds to the α1 site on one α-subunit, it is suggested that this induces a conformational change in the receptor which ultimately allows the insulin molecule to interact with the α2 site on the second subunit. Consequently, the two α-subunits are cross-linked (homo dimerisation), resulting in high affinity binding between insulin and its receptor and subsequent activation of the receptor. However, although another insulin molecule may potentially bind to the α1 site that is vacant, the previous conformational change prevents it from interacting with the second α2 site, causing this interaction to be one of lower affinity. L. Schaffer (15) suggests that negative interactions between the cross-linked tracer insulin and a native insulin molecule bound at this second α1 site may explain the accelerated dissociation in the presence of high concentrations of insulin. However, B. J. Hammond et al. (6) discount this explanation and propose that the acceleration is in fact due to the destabilisation of the cross-linked formation upon the second insulin molecule binding. At very high concentrations of unlabelled insulin, acceleration of tracer insulin dissociation from receptor is inhibited and is attributed by both P. De Meyts (14) and L. Schaffer (15) to monovalent insulin binding of a third insulin molecule to the vacant low affinity α2 site (B. J. Hammond et al. (6)). Therefore, although the stoichiometry of insulin binding to its receptor can support up to three molecules of insulin bound per α2β2 receptor, the more complex 1:2 and 1:3 complexes occur at supra physiological concentrations of insulin and may not be physiologically relevant.

Another factor that may contribute to the complexity of the interaction between insulin and its receptor is the possible involvement of other non-receptor related molecules. J. T. Harmon et al. (16), propose the presence of a membrane protein affinity regulator of insulin binding in rat liver membranes from ob/ob mice. They report that the effect of this protein is to cause a lowering of insulin affinity for its receptor. In the presence of high salt, high pH or purification of receptors on lectin columns, insulin's apparent affinity for its receptor increases. This effect is reversed by dilution of salt or reduction of pH. A similar effect in human placental plasma membranes has been observed and the apparent increase in affinity that has been determined is due to a two-fold increase in the high affinity component of insulin binding rather than an increase in affinity of either the high or low affinity site. R. A. Kohanski and M. D. Lane (17) also demonstrate the presence of a peripheral membrane glycoprotein which is involved in the modulation of insulin binding, while J. Maturo and M. Hollenberg (18) observe a reduction in binding affinity when purified insulin receptors are supplemented with the glycoprotein eluant from the affinity column used to purify them (also observed in our laboratory). E. R. Mortensen et al (19) demonstrate that mild reduction of adipocyte plasma membranes increases the proportion of high affinity insulin binding which is decreased in the presence of GTP, and is temperature and concentration dependent. Thus, the temperature effect observed by E. Helmerhorst and C. Yip (12) may be attributed to the presence of a G-protein that modulates insulin binding. More recently, the presence of a 66 kDa GTP-binding protein in human placental plasma membrane preparations has been shown to influence the binding kinetics of insulin (20). A decrease in insulin binding to the insulin receptor occurs upon pre-incubation of the insulin receptor-G-protein fraction with GTPγS (a stable analogue of GTP), suggesting an important interaction between the insulin receptor and a G-protein. The presence of such a peripheral membrane protein has not been widely espoused in the literature, however, it may well explain some of the complexities of the binding interaction.

Receptor oligormerisation is a ubiquitous phenomenon among growth factor receptors. It may be induced by monomeric ligands such as EGF to induce conformational changes that result in receptor-receptor interactions, or bivalent ligands (eg human growth hormone (hGH)) that mediate dimerisation of neighbouring receptors. The structure of subclass II receptors eg. insulin and IGF-1, are different because they exist as disulfide linked pairs of dimers in a heterotetrameric structure. In these cases, ligand binding to the receptor induces allosteric interaction between the two αβ halves to activate the receptors.

Recently, through high resolution structural and functional studies the fundamental mechanics of ligand-induced receptor activation is beginning to be elucidated. These studies indicate that oligomerisation of receptor subunits may be all that is required for receptor activation. Moreover, the proposed models explain some of the complex kinetics observed in ligandireceptor binding and dose-response studies of these molecules. For example, a model of homodimerisation of growth hormone receptor explains the unusual bell-shaped dose response curve which is caused by monovalent binding of hGH to each receptor monomer and subsequent prevention of dimerisation.

It is generally accepted that insulin binding induces a conformational change in the insulin receptor that is responsible for receptor activation. A number of studies indicate that this conformational change may occur by a cross-linking mechanism, similar to that described above. Firstly, insulin receptors are activated by a number of anti insulin receptor antibodies, but not by monovalent Fab' fragments, which implies a receptor cross-linking mechanism of activation similar to EGF receptors. Secondly, the homobifunctional cross-linking agent disuccinimide suberate forms more $\alpha_2$ species in the presence than in the absence of insulin, indicating that insulin draws the α-subunits into close proximity. Thirdly, reduced αβ dimer half receptors, when immobilised on wheat germ agglutinin Sepharose do not phosphorylate in the presence of insulin. However, when they are free to associate in solution, insulin causes phosphorylation of the β-subunits, indicating that cross-linking of receptor αβ halves must occur for receptor activation. Finally, concanavalin A induces insulin receptor activation by cross-linking receptors in intact cells, but when monovalent, only slightly induces receptor activation.

Although the dimeric insulin receptor can bind two (or more) insulin molecules (compared with growth hormone which cross-links two hGH receptors) the first insulin molecule binds more tightly than the second molecule and maybe all that is physiologically relevant for receptor activation. In this respect, insulin receptor activation may well be synonymous with hGH activation of its receptor (or similar cytokine/hormone receptor activation). Indeed, the increased rate of dissociation of tracer insulin in the presence of unlabelled insulin has been explained by analogy to the self-antagonism seen for hGH and its receptors.

Insulin binding to the two receptor α-subunits causes activation of the receptor β-subunit tyrosine kinase activity which leads to the phosphorylation of various substrates of insulin action. This includes the phosphorylation of a family of insulin receptor substrates (IRS) that are believed to be the immediate downstream effector molecules of much of insulin action. At present four members of the IRS family have been discovered. It is believed that these molecules have the potential to interact with, and thereby activate, other downstream signalling molecules, leading to many of the actions of insulin. However, the signalling pathways regulated by the individual substrates may vary.

Given the importance of insulin in maintaining glucose homeostasis then, it is clear that any change in the levels of insulin secreted or the responsiveness of cells to insulin may have significant consequences. Decreased secretion of insulin, or decreased responsiveness of cells to insulin results in Diabetes Mellitus, a group of individual conditions, distinguished by the varying causes of hyperglycemia.

Diabetes is a complex disease with many causative factors. Hyperglycemia is a major characteristic of the disease and over time, especially if poorly controlled, leads to many complications of the disease. These complications include microvascular and macrovascular diseases, retinopathy, neuropathy, stroke, hypertension, heart and kidney disease. Careful control of blood glucose levels is, therefore, a key strategy in treatment of diabetes.

Type 1 diabetes mellitus, or insulin-dependent diabetes mellitus (IDDM) is the more severe form of the disease, and is usually detected before 40 years of age. IDDM results from an autoimmune disorder leading to an inability of the body to produce the insulin needed to help maintain blood glucose levels within a normal range (the roles of insulin and how it works is described in more detail below). The symptoms of IDDM include polyuria, polyphagia, polydipsia, weight loss and drowsiness.

Presently, IDDM patients are absolutely dependent on regular injections of insulin for survival. Over 20 million people worldwide are dependent upon insulin in this manner.

Several different types of human insulin are commercially available for diabetics, ranging from the fast-acting Humulin™BR and Novolin™ to slower acting treatments, such as Protamine-zinc-insulin (PZI), Neutral protamine Hagedorn (NPH) insulin and Lente insulin. Insulin analogues like Humalog (LysPro) with altered properties are also available. Each of these insulin therapies have their advantages and disadvantages and so the choice of insulin therapy should be made by the patient and physician with all information about the patient's lifestyle, physical performance, and drug preferences.

The more common form of diabetes, representing in excess of 90% of all diagnosed cases, is referred to as Type 2 diabetes mellitus or non-insulin dependent diabetes mellitus (NIDDM). NIDDM can be triggered by both genetic and environmental factors and is often found in obese individuals. There are at least two fundamental defects associated with NIDDM. One is an increase in the resistance of cells in peripheral tissue to the presence of insulin.

Another is decreased secretion of insulin by the β-cells damaged by long-term, elevated blood glucose levels.

The disruption of the insulin receptor substrate (IRS) signalling system involved in mediating the cellular response to insulin also may play a role in the development of NIDDM. Unlike IDDM, the clinical symptoms of NIDDM are often mild, and the condition may even be asymptomatic. NIDDM patients usually do not depend upon insulin injections for their survival. About half adequately control blood glucose levels through dietary therapy and exercise regimes. The others use various oral hypoglycemia agents such as sulfonylureas, biguanides, and α-glucosidase inhibitors, or insulin, or various combinations of them to help regulate their blood glucose levels. The exact drug prescribed to a patient depends not only on the patient's clinical characteristics, but also the pharmacological properties of the treatment.

The sulfonylureas are the most common oral hypoglycemics and are traditionally used in the treatment of non-obese sufferers of NIDDM. They promote the beta-cells in the Islets of Langerhans of the pancreas to secrete insulin and so they effectively augment glucose-induced insulin secretion.

However, these drugs appear to be responsible for inducing hypoglycemic episodes in patients with the incidence of this apparently increasing when sulfonylureas are used in conjunction with alcohol, drugs which potentiate sulfonylurea action, poor food intake or renal impairment. A weight gain is often associated with sulfonylurea use making these compounds undesirable for the treatment of NIDDM in overweight patients.

The biguanide class of oral hypoglycemic agents increase insulin sensitivity and therefore can be used to lower blood glucose levels in NIDDM. Their mechanism of action is unclear. Phenformin is no longer used to treat NIDDM as it can cause fatal lactic acidosis. Metformin now is the only biguanide in clinical use worldwide. It is most commonly used when dietary therapy is unsuccessfully used to regulate blood glucose levels in obese patients. Metformin may be used in conjunction with sulfonylureas in instances where sulfonylurea therapy alone is inadequate or it may be used in combination with insulin in the treatment of IDDM. However, the adverse side-effects of metformin therapy may include lactic acidosis, nausea, bloating, diarrhoea and abdominal cramping.

α-Glucosidase inhibitors are also used to treat NIDDM as an adjunct to dietary measures or sulfonylureas therapy. These compounds allow carbohydrate in the gut to be processed more effectively by slowing down their absorption from the intestinal tract. Adverse side effects of these compounds include flatulence, diarrhoea and abdominal pain.

The thiazolidinediones are another class of compounds that may ameliorate symptoms of NIDDM. These compounds work by reducing insulin resistance at the sites of insulin action in the muscle and liver. They may be used in combination with insulin or sulfonylurea drugs but are not recommended for the treatment of IDDM. Severe adverse side-effects are rarely observed, however, some NIDDM patients fail to respond to this treatment.

Conversely, a number of clinical conditions are characterised by hyperinsulinism that leads to hypoglycaemia.

Insulin or hypoglycaemic drug overdose are clinical conditions that are often difficult to manage and may require hospitalisation and several days of intensive care. Non-accidental overdose or suicide attempts are fairly rare but often lead to death or profound neurologic impairment. The key symptoms of insulin overdose are hypoglycaemia, hypokalaemia and acid-base imbalance. Sulfonylurea drug overdose predominantly causes hypoglycaemia.

Insulinomas account for about 90% of all pancreatic endocrine tumours. They occur with an incidence of about 0.5 per million population and people of all ages can be affected. Early diagnosis and treatment of insulinomas is essential because of their variable manifestations and potential lethality. These tumours are usually benign but synthesise and secrete insulin autonomously causing spontaneous hypoglycaemia. Symptoms may include deep coma, epilepsy, dizziness, weakness, hunger and epigastric pain.

Congenital hyperinsulinism is the most common cause of severe, persistent hypoglycaemia in infants. It may be familial as up to 20% of affected families have more than one affected child. A defect in beta-cell function is the most likely explanation for the hyperinsulinism that can lead to brain damage and death if not detected early.

Gastric dumping syndrome is encountered in approximately 25–50% of patients following gastric surgery and may persist post-operatively for several months. Early dumping usually involves gastrointestinal and vasomotor complaints. Late dumping predominantly involves vasomotor complaints and is a consequence of a reactive hypoglycaemia resulting from hyperinsulinism and an exaggerated release of glucagon-like peptide-1. The gastric dumping syndrome is infrequently reported in children, but is difficult to diagnose and manage and has significant morbidity.

It is critical that the hypoglycaemia, secondary to the hyperinsulinism and characteristic of clinical conditions like those described above, be managed quickly if death or profound neurologic impairment is to be avoided.

The mainstay of therapy in the management of severe hypoglycaemia is glucose or dextrose infusion. In cases of drug overdose, this may follow gut decontamination. Glucagon is used sometimes but considerable caution must be taken because its success depends on limited hepatic glycogen stores. Surgical intervention is quite successful for many insulinomas where the lesion can be appropriately localised. In the case of congenital hyperinsulinism, partial or complete pancreotectomy is often necessary. Surgical excision of injection sites in cases of massive, non-accidental insulin overdose also is sometimes the preferred option.

Diazoxide is sometimes used to combat hyperinsulinism. It is a potent antihypertensive agent and acts to promote blood glucose level by suppressing insulin secretion from the pancreas. However, this drug is not specific in its treatment of hyperinsulinism and a number of undesirable side effects may follow its use. Hypotension, nausea, vomiting, dizziness, weakness and mild liver damage have been reported with its use. Severe hypoglycaemia also persists in some patients following diazoxide therapy.

Octreotide is a peptide analog of somatostatin and, like diazoxide, one of its actions is to inhibit insulin secretion from the pancreas. Octreotide has shown some promise in treating patients with hyperinsulinism, however, resistance to the drug has been reported in some patients with insulinoma. It has been used with some success in treating gastric dumping syndrome in patients refractory to standard therapy. However, its long term use is limited by side-effects such as diarrhoea and steatorrhoea. Moreover, octreotide may in some instances worsen existing hypoglycaemia by suppressing glucagon and growth hormone in the presence of unresponsive pancreatic hyperinsulinism. Octreotide therapy may also have undesired effects on reducing long term growth in infants.

Thus, as can be deduced from the foregoing discussion, the only drugs available for treating hyperinsulinism with secondary hypoglycaemia, act by suppressing further insulin secretion from the pancreas. No other drugs are presently available.

Antagonists of insulin action would be therapeutically useful agents for treating a range of diseases or clinical conditions involving hyperinsulinism and hypoglycaemia. They would work by directly competing with insulin for binding to the insulin receptor (the first step of insulin action) and would thereby counter the effects of hyperinsulinism. Their effect would be to reduce the hypoglycaemic action of insulin evident in clinical conditions described above.

In view of the foregoing, it will be appreciated that there is a current on going need for biological modifiers that are capable of mimicing insulin activity.

SUMMARY OF THE INVENTION

The present invention relates to the use of at least a non-peptidyl compound as a biological modulator of insulin activity or insulin-related activity, which compound possesses ionic and hydrophobic chemical moieties spatially located so as to mimic at least an ionic and hydrophobic amino acid residue of insulin, which amino acids are associated with the binding of insulin to its receptor.

Compounds of the present invention exert their effects by mimicking amino acids spatially located on insulin, enabling those compounds to bind to the insulin receptor or a like receptor causing biological modulation of the activity of the receptor. Compounds used in the present invention may act either as agonists or antagonists of insulin or insulin-like activity.

Thus, in a first embodiment the invention resides in a method for treating a patient suffering from one or more insulin related ailments, which method comprises the step of: administering to a patient an therapeutically effective amount of a compound that is a biological modulator of insulin activity, which compound possesses ionic and hydrophobic chemical moieties spatially located so as to mimic at least an ionic and hydrophobic amino acid residue of insulin, which amino acids are associated with the binding of insulin to its receptor.

In a second embodiment, there is provided a method for identifying a non-peptidyl compound possessing ionic and hydrophobic chemical moieties spatially located so as to mimic particular ionic and hydrophobic amino acid residues of insulin which are associated with the binding of insulin to its receptor, said method comprising the steps of: (1) comparing the three dimensional structure of the non-peptidyl compound with a three dimensional pharmacophore of an active site of insulin; and (2) selecting a non-peptidyl compound with ionic and hydrophobic chemical moieties spatially located so as to mimic said site.

In a third embodiment, there is provided a method for determining whether a non-peptidyl compound identified by the third embodiment of the invention is an agonist or an antagonist, said method comprising the step of: exposing the compound to an insulin or insulin like receptor and measuring the change in biological activity following exposure of the compound to the receptor.

The present invention also contemplates novel chemical compounds identified by the method of the present invention as well as the use of those molecules in a pharmaceutical composition. The pharmaceutical composition comprising a chemical compounds capable of modulating the biological activity of insulin or and a pharmaceutically acceptable carrier and/or diluent.

BRIEF DESCRIPTION OF THE FIGURES

FIG. 2 tabulates a series of hypotheses generated from the insulin pharmacophore of FIG. 1.

FIG. 3 tabulates features and tolerances of the hypotheses of FIG. 2 used in the searching of three dimensional chemical databases.

FIG. 4 tabulates hypotheses and tolerances found to identify IM 175 in database searches, where the tolerance sphere for all features of the listed hypotheses was the size indicated in the body of the table.

DETAILED DESCRIPTION OF THE INVENTION

Figure 1:
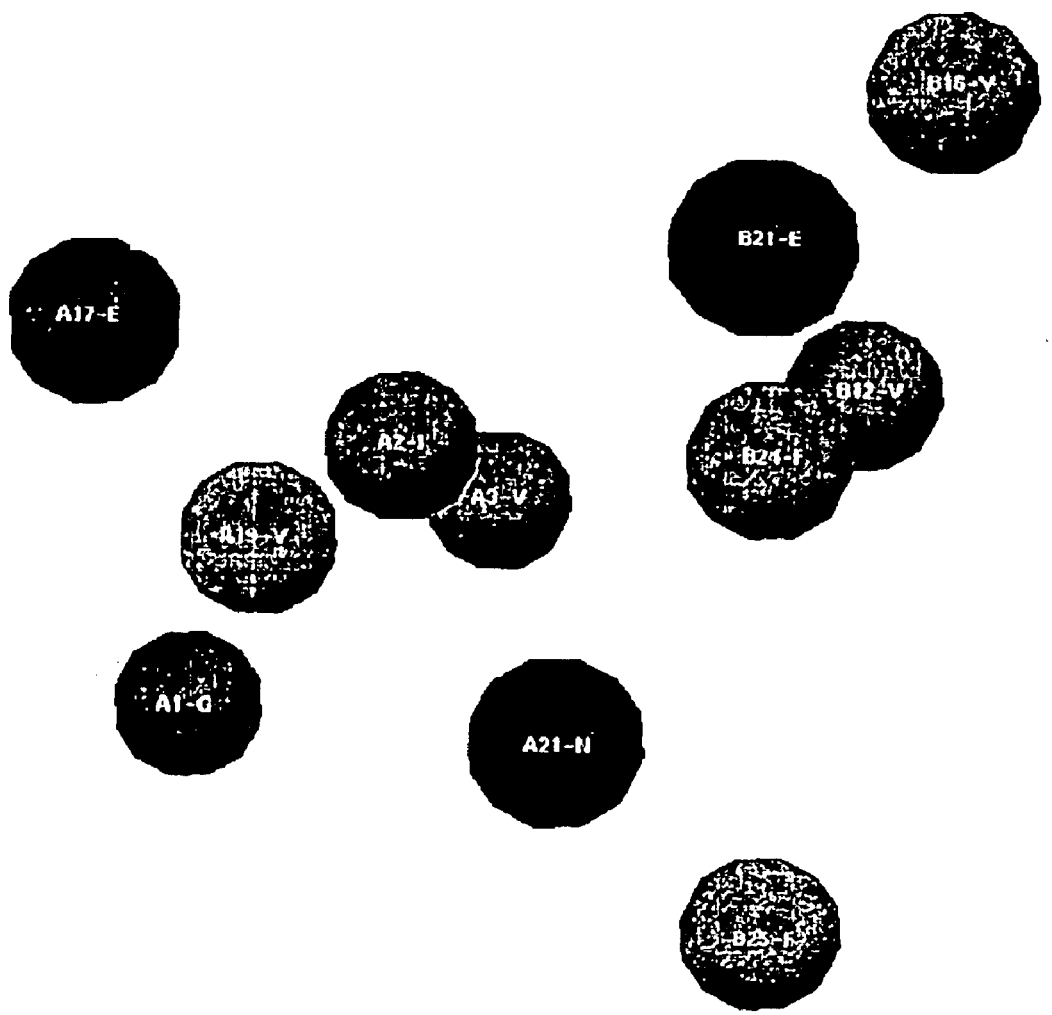
FIG. 1 shows a receptor binding pharmacophore of insulin.

The present invention relates to the use of at least a non-peptidyl compound as a biological modulator of insulin activity or insulin-related activity, which compound possesses ionic and hydrophobic chemical moieties spatially located so as to mimic at least an ionic and hydrophobic amino acid residue of insulin, which amino acids are associated with the binding of insulin to its receptor.

In a first embodiment, the invention resides in a method for treating a patient suffering from one or more insulin related ailments, which method comprises the step of: administering to a patient an therapeutically effective amount of a compound that is a biological modulator of insulin activity, which compound possesses ionic and hydrophobic chemical moieties spatially located so as to mimic at least an ionic and hydrophobic amino acid residue of insulin, which amino acids are associated with the binding of insulin to its receptor.

The phrase "biological modulator" as used herein refers to a compound that is capable of least varying insulin activity when introduced into a biological system (eg an in vitro or in vivo system). Such a compound may either be an antagonist or an agonist of biological activity. Most preferably the non-peptidyl compound used in either the first or second embodiment of the invention is an insulin agonist.

As used herein the term "patient" refers to any animal that may be suffering from one or more insulin related ailments. Most preferably the animal is a mammal. The term "mammal" as used herein refers to a class of vertebrates whose young feed upon milk from the mother's breast. Most species are more or less hairy, all have a diaphragm, and all (except the monotremes) are viviparous. The term will be understood to include for example human, farm animals (i.e., cattle, horses, goats, sheep and pigs), household pets (i.e., cats and dogs) and the like.

The phrase "therapeutically effective amount" as used herein refers to an amount of a non-peptidyl compound sufficient to modulate a biological activity associated with the interaction of insulin with its receptors.

Insulin related ailments include ailments which are related to decreased secretion of insulin, decreased responsiveness of cells to insulin, or increased secretion of insulin and may, for example, include ailments such as: diabetes mellitus (types 1 and 2), insulinomas, insulin and hypoglycaemic drug overdose, gastric dumping syndrome and congenital hyperinsulinism. Other ailments will be known to those of ordinary skill in the field. For example, insulin and glucose therapy leads to improved cognition in alzheimers disease patients.

Amino acids associated with the binding of insulin to its receptor include, by way of example: A21 Asn, B21 Glu, A17 Glu, B24 Phe, B25 Phe, A19 Tyr, B12 Val, B16 Tyr, A2 Ile, A3 Val and A1 Gly. As used herein the "A" or "B" nomenclature refers to either the A or B chain that forms insulin while the number identifies the amino acid number in either chain.

While the non-peptidyl compounds employed in the present invention may mimic any number of the amino acids associated with the binding of insulin to its receptor, preferably they mimic ionic and hydrophobic moieties associated with at least two of these amino acid. More preferably, the compounds mimic ionic and hydrophobic residues on at least 4 of the abovementioned amino acids, including at least one amino acid from the group comprising: A21 Asn, B21 Glu and A17 Glu. Even more preferably, the compounds mimic ionic and hydrophobic residues on at least 4 amino acids, including at least one amino acid selected from the group comprising A17 Glu, B21 Glu and A21 Asn, and at least one amino acid selected from the group comprising: B24 Phe, B25 Phe, A19 Tyr, B12 Val and B16 Tyr. Desirably, the non-peptidyl compound mimics ionic and hydrophobic residues associated with at least one of the following groups of amino acid residues:

1 A21 Asn, B21 Glu, A17 Glu, B24 Phe, B25 Phe;

2 A21 Asn, B21 Glu, B24 Phe, B25 Phe;

3 A21 Asn, B21 Glu, B24 Phe, B25 Phe, A1 Gly, A2 Ile, A3 Val;

4 A21 Asn, B21 Glu, A17 Glu, A19 Tyr, A1 Gly, A2 Ile, A3 Val;

5 A21 Asn, B21 Glu, A17 Glu, B12 Val, A1 Gly, A2 Ile, A3 Val;

6 A21 Asn, B21 Glu, B12 Val, A1 Gly, A2 Ile, A3 Val;

7 A21 Asn, B21 Glu, A17 Glu, B16 Tyr, A1 Gly, A2 Ile, A3 Val;

8 A21 Asn, B21 Glu, A17 Glu, A19 Tyr, B12 Val, B16 Tyr;

9 A21 Asn, B21 Glu, A19 Tyr, B12 Val, B16 Tyr;

10 A21 Asn, B21 Glu, A17 Glu, B24 Phe, B25 Phe, A19 Tyr, B12 Val, B16 Tyr;

11 A21 Asn, B21 Glu, B24 Phe, B25 Phe, A19 Tyr, B12 Val, B16 Tyr;

12 A21 Asn, B21 Glu, B24 Phe, B25 Phe, B12 Val, B16 Tyr,

13 A21 Asn, B21 Glu, A17 Glu, B24 Phe, B25 Phe, A19 Tyr;

14 A21 Asn, B21 Glu, B24 Phe, B25 Phe, A19 Tyr;

15 A21 Asn, A17 Glu, B24 Phe, B25 Phe, A19 Tyr;

16 B21 Glu, A17 Glu, B24 Phe, B25 Phe, A19 Tyr;

17 A21 Asn, B21 Glu, A17 Glu, B24 Phe, B25 Phe, B12 Val;

18 A21 Asn, B21 Glu, B24 Phe, B25 Phe, B12 Val;

19 A21 Asn, A17 Glu, B24 Phe, B25 Phe, B12 Val;

20 B21 Glu, A17 Glu, B24 Phe, B25 Phe, B12 Val;

21 A21 Asn, B21 Glu, A17 Glu, B24 Phe, B25 Phe, B16 Tyr;

22 A21 Asn, B21 Glu, B24 Phe, B25 Phe, B16 Tyr;

23 A21 Asn, A17 Glu, B24 Phe, B25 Phe, B16 Tyr;

24 B21 Glu, A17 Glu, B24 Phe, B25 Phe, B16 Tyr;

25 A21 Asn, B21 Glu, A17 Glu, B24 Phe, A19 Tyr, B12 Val, B16 Tyr;

26 A21 Asn, B21 Glu, B24 Phe, A19 Tyr, B12 Val, B16 Tyr;

27 A21 Asn, A17 Glu, B24 Phe, A19 Tyr, B12 Val, B16 Tyr;

28 B21 Glu, A17 Glu, B24 Phe, A19 Tyr, B12 Val, B16 Tyr;

29 A21 Asn, B21 Glu, A17 Glu, B25 Phe, A19 Tyr, B12 Val, B16 Tyr;

30 A21 Asn, B21 Glu, B25 Phe, A19 Tyr, B12 Val, B16 Tyr;

31 A21 Asn, A17 Glu, B25 Phe, A19 Tyr, B12 Val, B16 Tyr; or

32 B21 Glu, A17 Glu, B25 Phe, A19 Tyr, B12 Val.

Any compound capable of mimicking the spatial arrangements of the foregoing amino acids may be employed in the present invention. Preferably, the non-peptidyl compound has the following formula:

$$AXYXZ_n \qquad \text{(formula 1)}$$

where A is W or VXW;

V is $V_1$ or $V_2$;

V is substituted with up to two X groups;

$V_1$ is a phenyl or 6 membered heteroaromatic ring, optionally substituted with up to 5 $R_1$ groups;

$V_2$ is a 5 member ring system which may incorporate up to 4 hetero atoms which may be independently a nitrogen atom, a nitrogen atom optionally substituted with $R_2$, oxygen or sulfir, the ring system being optionally substituted with up to 4 $R_1$ groups;

W is $W_1$ or $W_2$ or $W_3$;

W is substituted with up to two X groups;

$W_1$ is $V_1$;

$W_2$ is a fused bicyclic ring system comprising rings of 5 or 6 atoms, which may incorporate up to 4 hetero atoms, which may be independently a nitrogen atom, a nitrogen atom optionally substituted with $R_2$, oxygen or sulfur, the system being optionally substituted with up to seven $R_1$ groups;

$W_3$ is —N($R_2$)R'$_2$;

$R_1$ is independently H, OH, alkyl, alkenyl, alkynyl, alkoxy, alkanol, hydroxyalkoxy, haloalkyl, haloalkoxy, halogen, SH, thioalkyl, cyano (—CN), N($R_2$)R'$_2$, phenyl phenyl optionally substituted with up to five alkyl groups of 1 to 3 carbon atoms or up to five halogen atoms, benzyl, phenethyl, nitro, —COR$_3$, —RCOR$_3$, —R$_5$SOR$_3$, —R$_5$SO$_2$R$_3$, —SO$_2$N($R_2$)R'$_2$, or azido;

$R_2$ and R'$_2$ are independently H, alkyl of 1 to 6 carbon atoms, alkenyl of 3 to 6 carbon atoms, alkynyl of 3 to 6 carbons, hydroxyalkyl of 2 to 6 carbons, alkoxy of 2 to 6 carbons, haloalkyl, haloalkenyl, haloalkoxy, benzyl, benzyl optionally substituted with up to four $R_1$ groups, phenylethyl, phenylethyl optionally substituted with up to four $R_1$ groups, arylalkyl, and where $R_2$ and R'$_2$ can also be joined to form cyclic structures;

$R_3$ is independently H, OH, alkyl, alkenyl, alkynyl alkoxy, alkanol, hydroxyalkoxy, —R$_4$N($R_2$)R'$_2$, mesyl, triflouromesyl, —NHSO$_2$CH$_3$ or —NHSO$_2$CF$_3$;

$R_4$ is independently a bond, alkyl, alkenyl or alkynyl;

X is independently, a bond, —R$_4$N($R_2$)R$_4$—, —R$_4$N=NR$_4$—, —R$_4$N($R_2$)—N($R_2$)R$_4$—, —R$_4$OR$_4$—, —R$_4$SR$_4$—, —R$_5$—, —R$_5$O—, —R$_5$S—, —R$_5$N($R_2$)—, —SO—, sulfonyl (—SO$_2$—), —CO—, —CONH—, —NHCONH—, —NHCO—, —CONHCO—, —CON($R_2$)—, —R$_5$COR$_5$—, —R$_5$COR$_5$N($R_2$)R$_5$—, —N($R_2$)CO— or —R$_4$N($R_2$)R$_4$COR$_4$—;

$R_5$ is independently alkyl, alkenyl, alkynyl, alkoxy, alkanol, hydroxyalkoxy;

Y is either $Y_1$, $Y_2$ or $Y_3$;

Y is substituted with at least two, but optionally up to four X linking groups;

$Y_1$ is a fused bicyclic ring system comprising rings of 5 or 6 atoms which may incorporate up to 4 hetero atoms, which may be independently a nitrogen atom, a nitrogen atom optionally substituted with $R_2$, oxygen or sulfur, the ring system optionally independently incorporating a sulfoxide (SO), sulfone (SO$_2$) or carbonyl (CO) group and optionally up to seven $R_1$ groups;

$Y_2$ is a 6:6:6 or a 6:5:6 fused tricyclic system which may incorporate up to 4 hetero atoms which may be independently a nitrogen atom, a nitrogen atom optionally substituted with $R_2$, oxygen or sulfur, the ring system optionally independently incorporating a sulfoxide (SO), sulfone (SO$_2$) or carbonyl (CO) group, and the ring system being substituted with at least two, but optionally up to four X linking groups and optionally up to seven $R_1$ groups;

$Y_3$ is $V_1$;

Z is independently —R$_6$COOH, —R$_6$SO$_3$H, —R$_6$NO$_2$, —R$_6$SO$_2$H, —R$_6$SO$_2$NHR$_2$; —R$_7$SO$_2$NHCOR$_4$—N-trifluoromesylsulfonamidate, —OH, -2-yl-hydoxyethanoic acid (—CH(OH)COOH), -3-yl-2-hydroxypropanoic acid (—CH$_2$CH(OH)COOH)-2-yl-2-hydroxypropanoic acid (—CH(CH$_3$)(OH)COOH), -3-yl-2,3-dihydroxypropanoic acid (—CH(OH)CH(OH)COOH), -2-yl-2,3-dihydroxypropanoic acid (—C(CH$_2$(OH))(OH)COOH), -3-yl-2-hydroxypropan-3-one-1-oic acid (—COCH(OH)COOH, 2-yl-2-hydroxypropandioic acid (—C(COOH)(OH)COOH), -2-yl-propandioic acid (—C(COOH)(H)COOH), -4-yl-2-hydroxybutan-4-one-1-oic acid (—COCH$_2$CH(OH)COOH, 2-yl-2-hydroxybutan-1,4-dioic acid (—C(OH)(COOH)CH$_2$COOH), 3-yl-2-hydroxybutan-1,4-dioic acid (—CH(CH(OH)COOH)COOH), 5-yl-tetrazole,

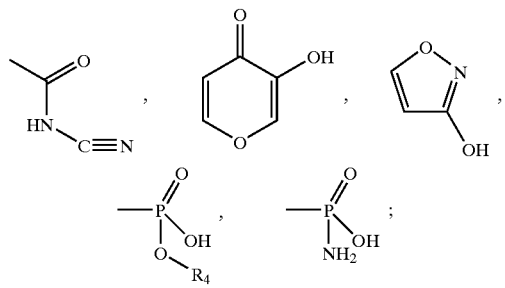

$R_1$ is independently a bond, alkyl, alkenyl, alkynyl, alkoxy, —CO(CH$_2$)$_n$—, where n is an integer between 0 and 4, alkanoic, alkenoic or alkynoic;

with the exception that where $W_1$ is an optionally substituted phenyl then $Y_3$ cannot be an optionally substituted phenyl.

The term "alkyl" as used herein refers to an alkane derived radical of between 1 and 6 carbon atoms unless otherwise defined, including straight, branched or cyclic alkane derived radicals, monovalent or bivalent alkane derived radicals in that it may be joined to one or two groups via any allowed bond to its carbon atoms. Preferably, the straight or branched alkyl groups are methyl, ethyl, propyl, isopropyl, butyl, i-butyl, t-butyl, pentyl, or hexyl and the cycloalkyl groups are cyclopentyl or cyclohexyl.

The term "alkenyl" as used herein refers to a hydrocarbon derived radical containing from 2 to 6 carbon atoms, unless otherwise defined and at least one carbon to carbon double bond, and includes straight, branched or cyclic hydrocarbon derived radicals, monovalent or bivalent hydrocarbon derived radicals in that such alkane derived radicals may be joined to one or two groups via any allowed bond to its carbon atoms. Preferably, the alkenyl groups are ethenyl, propenyl, butenyl, cyclopentenyl, or cyclobutenyl.

The term "alkynyl" as used herein refers to a hydrocarbon derived radical containing from 2 to 6 carbon atoms and at least one carbon to carbon triple bond and includes straight chained or branched hydrocarbon derived radicals, monovalent or bivalent hydrocarbon derived radicals in that such hydrocarbon derived radicals may be joined to one or two groups via any allowed bond to its carbon atoms. Preferably, the alkynyl groups are ethynyl, propynyl or butynyl.

The term "alkoxy" as used herein refers to an alkyl group of indicated carbon atoms, attached to other groups through an oxygen linkage (monovalent) or; to other groups through an oxygen linkage and a bond to any of its allowed carbon atoms (bivalent).

The term "hydroxyalkoxy" as used herein refers to an alkoxy group substituted at one or more carbon atoms, with one or more hydroxyl groups.

The term "haloalkoxy" as used herein refers to an alkoxy group substituted at one or more carbon atoms, with one or more halogen atoms. Preferably, the halogen substituents are fluorine, chlorine, bromine or iodine.

The term "alkanol" as used herein refers to an alkyl group substituted at one or more carbon atoms, with one or more hydroxyl groups.

The term "haloalkyl" as used herein refers to an alkyl group substituted at one or more carbon atoms, with one or more halogen atoms. Preferably, the halogen substituents are fluorine, chlorine, bromine or iodine.

The term "thioalkyl" as used herein refers to an alkyl group of indicated carbon atoms, attached to other groups through a sulfur linkage.

The term "alkanoic" as used herein refers to an alkyl group of indicated carbon atoms, substituted at one carbon atom with a carboxylic acid group (—COOH).

The term "alkenoic" as used herein refers to an alkenyl group of indicated carbon atoms, substituted at one carbon atom with a carboxylic acid group (—COOH).

The term "alkynoic" as used herein refers to an alkynyl group of indicated carbon atoms, substituted at one carbon atom with a carboxylic acid group (—COOH).

More preferably, when the non-peptidyl compound employed in the invention has the structure of formula 1 above and V is $V_1$ or $V_2$, then:

$V_1$ is selected from the group consisting of, benzene, pyridine, pyridazine, pyrimidine, pyrazine or triazine and is optionally substituted with up to 5 $R_1$ groups; and $V_2$ is selected from the group consisting of, cyclopenta-1,3-diene, pyrrole, furan, thiophene, oxazole, isoxazole, pyrazole, imidazole, thiazole, isothiazole or triazole and is optionally substituted with up to 4 $R_1$ groups;

and W is $W_2$ then $W_2$ is selected from the group consisting of naphthalene, quinoline, isoquinoline, phthalazine, naphthyridine, quinoxaline, quinazoline, cinnoline, pteridine, indole, benzothiophene, benzofuran, benzimidazole, indazole, benzoxazole, benzisooxazole, benzthiazole, benzisothiazole, purine, indoline or isoindoline and is optionally substituted with up to seven $R_1$ groups;

and Y is either $Y_1$ or $Y_2$ then $Y_1$ is selected from the group consisting of croman, isochroman, benzofuran, cromene, 1,2,3,4-tetrahydronaphthalene, 1,4-dihydronaphthalene, indan, indene, benzopiperidine, indoline, isoindoline, quinoline, isoquinoline, phthalazine, naphthyridine, quinoxaline, quinazoline, cinnoline or pteridine, coumarin or 2,3-dihydrocoumarin and is optionally substituted with up to seven $R_1$ groups; and $Y_2$ is selected from the group consisting of 9H-xanthone, 9H-xanthene, phenoxathiin, phenoxathiin-10-oxide, phenoxathiin-10-dioxide, acridine, phenazine, phenothiazine, phenoxazine, phenothiazine-5-oxide, phenothiazine-5-dioxide, thiathrene-5-dioxide, thiathrene-5-oxide, carbazole, dibenzo[b,d]furan or dibenzo[b,d]thiophene and is optionally substituted with up to seven $R_1$ groups.

Desirably, when the non-peptidyl compound employed in the invention has the structure of formula 1 above and A is W or VXW then:

V is phenyl or pyrazole, optionally substituted with up to 5 $R_1$ groups;

and W is $W_1$, $W_2$ or $W_3$ then $W_1$ is phenyl optionally substituted with up to 5 $R_1$ groups;

$W_2$ is naphthalene or quinoline optionally substituted with up to seven $R_1$ groups wherein $R_1$ is independently H, OH, methyl, ethyl, propyl, nitro, methoxy, ethoxy, 2-hydroxyethoxy, chloro, fluoro or acetyl;

$W_3$ is —N($R_2$)$R_2$ wherein $R_2$ is propyl;

X is independently, a bond, methoxy (—OCH$_2$—), oxypropoxy (—O(CH$_2$)$_3$O—), hexenyloxy (—O-(CH$_2$)$_4$CH=CH—), sulfonyloxy (—SO$_2$O—), methyl (—CH$_2$—), amidyl (—CONH—) or —NHCONH—;

and Y is either $Y_1$ or $Y_2$ then $Y_1$ is croman, 4-H-chromen-4-one or napthalene optionally substituted with up to seven $R_1$ groups wherein $R_1$ is independently H, OH, methyl, ethyl, propyl, nitro, methoxy, ethoxy, 2-hydroxyethoxy, chloro, fluoro or acetyl;

$Y_2$ is 9H-xanthone optionally substituted with up to seven $R_1$ groups wherein $R_1$ is independently H, OH, methyl, ethyl, propyl, nitro, methoxy, ethoxy, 2-hydroxyethoxy, chloro, fluoro or acetyl;

$Y_3$ is phenyl optionally substituted with up to 5 $R_1$ groups wherein $R_1$ is independently H, OH, methyl, ethyl, propyl, nitro, methoxy, ethoxy, 2-hydroxyethoxy, chloro, fluoro or acetyl; and Z is independently —$R_6$COOH, —$R_6$SO$_3$H or —N-trifluoromesylsulfonamidate wherein $R_6$ is independently a bond or propyl.

By way of example, the non-peptidyl compound(s) are selected from the group:

1. 4,4'-Methylenebis[3-hydroxy-2-naphthalenecarboxylic acid]
   (herein referred to as IM 025);
2. 7-[3-(4-acetyl-2-ethyl-5-hydroxyphenoxy)propoxy]-3,4-dihydro-8-propyl-2H-1-benzopyran-2-carboxylic acid
   (herein referred to as IM 071);
3. 2,4-dichloro-6-(N-(trifluoromethanesulfonyl)) sulfamoylphenyl 3,5-dichloro-2-hydroxybenzenesulfonate
   (herein referred to as IM 103);
4. 7-[(4-acetyl-3-hydroxy-2-propylphenyl)methoxy]-4-oxo-8-propyl-4H-1-benzopyran-2-carboxylic acid.
   (herein referred to as IM 127);

5. 7-[3-(4-acetyl-3-methoxy-2-propylphenoxy)propoxy]-3,4-dihydro-8-propyl-2H-1-benzopyran-2-carboxylic acid
   (herein referred to as IM 129);
6. 3,4-dihydro-8-propyl-7-[[3-[2-ethyl-5-hydroxy-4-(1H-pyrazol-3-yl)phenoxy]propyl]oxy]-2H-1-benzopyran-2-carboxylic acid
   (herein referred to as IM 132);
7. 3,4-dihydro-8-propyl-7-[[3-[2-ethyl-5-hydroxy-4-ethoxyphenoxy]propyl]oxy]-2H-1-benzopyran-2-carboxylic acid
   (herein referred to as IM 134);
8. 3-[4-[7-carboxy-9-oxo-3-[3-[2-ethyl-4-(4-fluorophenyl)-5-hydroxyphenoxy]propoxy]-9H-xanthene]]propanoic acid
   (herein referred to as IM 140);
9. 8-propyl-7-(quinol-2'-ylmethoxy)-3,4-dihydro-2H-1-benzopyran-2-carboxylic acid
   (herein referred to as IM 143);
10. 7-(naphth-2'-ylmethoxy)-8-propyl-3,4-dihydro-2H-1-benzopyran-2-carboxylic acid
    (herein referred to as IM 144);
11. N-(trifluoromethanesulfonyl)-3,5-dinitro-4-(N',N'-dipropylamino)benzenesulfonamide
    (herein referred to as IM 145);
12. 8-propyl-7-[3-[4-(4-fluorophenyl)-2-ethyl-5-hydroxyphenoxy]propoxy]-3,4-dihydro-2H-1-benzopyran-2-carboxylic acid
    (herein referred to as IM 171);
13. 3,4-dihydro-7-[[6-(4-methoxyphenyl)hexenyl]oxy]-8-propyl-2H-1-benzopyran-2-carboxylic acid
    (herein referred to as IM 172); or
14. 8,8'-[Carbonylbis[imino-3,1-phenylenecarbonylimino(4-methyl-3,1-phenylene)carbonylimino]]bis-1,3,5-naphthalenetrisulfonic acid
    (herein referred to as IM 175).

The non-peptidyl compounds described herein may also be prepared as dimers or heterodimers of compounds of the above mentioned formula $AXYXZ_n$ where such compounds are joined through a X linking group by way of their V or W groups.

It will be understood by those of ordinary skill in the field that the compounds of the present invention may also be prepared as dimers and/or heterodimers. Furthermore analogues and precursors of the abovementioned compounds may also be prepared for use in the invention.

The compounds of the present invention include chemical derivatives that may be converted to the above mentioned compounds in vivo, such derivatives including but not being limited to esters and amides.

The present invention also contemplates pharmaceutical composition comprising at least a chemical compound capable of modulating the biological activity of insulin and a pharmaceutically acceptable carrier and/or diluent.

The compounds selected for use in the invention are desirably prepared in a purified form suitable for administration to a patient. Purification of such compounds may be achieved by any means known in the art, such as distillation, chromatographic means etc.

Once purified the compounds may be formulated into therapeutics as neutral or salt forms. Pharmaceutically acceptable salts include, for example, the acid addition salts (formed with any free amino groups of the compounds) and which are formed with inorganic acid such as hydrochloric or phosphoric acids, or such organic acids as acetic, oxalic, tartaric, maleic and the like. Salts formed with free acidic groups may also be derived from inorganic bases such as, for example, sodium, potassium, ammonium, calcium, or iron (III) hydroxides, and such organic bases as isopropylamine, trimethylamine, 2-ethylamino ethanol, histidine, procaine and the like. The composition may further comprise excipients that are pharmaceutically acceptable and compatible with the active ingredient. Examples of excipients which may be used in such a formulation include water, saline, ethanol, dextrose, glycerol or the like, or combinations thereof. If desired, the composition may also contain minor amounts of auxiliary substances such as wetting agents, pH buffering agents, or emulsifying agents which enhance the compounds.

Pharmaceutical compositions may be administered by injection, or prepared for oral, pulmonary, nasal or for any other form of administration. Preferably the pharmaceutically acceptable composition(s) are administered, for example, intravenously, subcutaneously, intramuscularly, intraorbitally, ophthalmically, intraventricularly, intracranially, intracapsularly, intraspinally, intracisternally, intraperitoneally, buccal, rectally, vaginally, intranasally or by aerosol administration.

The mode of administration must, however, be at least suitable for the form in which the composition has been prepared. The mode of administration for the most effective response may need to be determined empirically and the means of administration described below are given as examples, and do not limit the method of delivery of the composition of the present invention in any way. All the above formulations are commonly used in the pharmaceutical industry and are commonly known to suitably qualified practitioners.

The compounds provided herein can be formulated into pharmaceutical compositions by admixture with pharmaceutically acceptable nontoxic excipients and carriers and administered by any parenteral techniques such as subcutaneous, intravenous and intraperitoneal injections. In addition the formulations may optionally contain one or more adjuvants.

The pharmaceutical forms suitable for injectable use include sterile aqueous solutions (where water-soluble) or dispersions and sterile powders for the extemporaneous preparation of sterile injectable solutions or dispersion. Alternatively, the compounds of the invention may be encapsulated in liposomes and delivered in injectable solutions to assist their transport across cell membrane. Alternatively or in addition such preparations may contain constituents of self-assembling pore structures to facilitate transport across the cellular membrane.

The carrier may be a solvent or dispersion medium containing, for example, water, ethanol, polyol (for example, glycerol, propylene glycol and liquid polyethylene glycol, and the like), suitable mixtures thereof, and vegetable oils. Proper fluidity may be maintained, for example, by the use of a coating such as licithin, by the maintenance of the required particle size in the case of dispersion and by the use of superfactants. Prolonged absorption of the injectable compositions can be brought about by the use in the compositions of agents delaying absorption, for example, aluminum monostearate and gelatin.

Sterile injectable solutions may be prepared by incorporating the active compounds in the required amount in an appropriate solvent with various of the other ingredients enumerated above, as required, followed by filtered sterilisation. Generally, dispersions are prepared by incorporating the various sterilised active ingredient into a sterile vehicle that contains the basic dispersion medium and the required other ingredients from those enumerated above. In the case of sterile powders for the preparation of sterile injectable solutions, the preferred methods of preparation are vacuum drying and freeze-drying techniques that yield a powder of the active ingredient plus any additional desired ingredient from previously sterile-filtered solution thereof.

Oral Delivery

Contemplated for use herein are oral solid dosage forms, which are described generally in *Martin, Remington's Pharmaceutical Sciences*, 18th Ed. (1990 Mack Publishing Co. Easton Pa. 18042) at Chapter 89, which is herein incorporated by reference. Solid dosage forms include tablets, capsules, pills, troches or lozenges, cachets or pellets. Also, liposomal or proteinoid encapsulation may be used to formulate the present compositions (as, for example, proteinoid microspheres reported in U.S. Pat. No. 4,925,673). Liposomal encapsulation may be used and the liposomes may be derivatised with various polymers (E.g., U.S. Pat. No. 5,013,556). A description of possible solid dosage forms for the therapeutic is given by Marshall, in *Modem Pharmaceutics*, Chapter 10, Banker and Rhodes ed., (1979), herein incorporated by reference. In general, the formulation will include the compounds described as part of the invention (or a chemically modified form thereof), and inert ingredients which allow for protection against the stomach environment, and release of the biologically active material in the intestine.

For the compounds described as part of the invention the location of release may be the stomach, the small intestine (the duodenum, the jejunem, or the ileum), or the large intestine. One skilled in the art has available formulations that will not dissolve in the stomach, yet will release the material in the duodenum or elsewhere in the intestine. Preferably, the release will avoid the deleterious effects of the stomach environment, either by protection of the composition or by release of the compounds beyond the stomach environment, such as in the intestine.

To ensure full gastric resistance, a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films.

A coating or mixture of coatings can also be used on tablets, which are not intended for protection against the stomach. This can include sugar coatings, or coatings that make the tablet easier to swallow. Capsules may consist of a hard shell (such as gelatin) for delivery of dry therapeutic i.e. powder; for liquid forms, a soft gelatin shell may be used. The shell material of cachets could be thick starch or other edible paper. For pills, lozenges, molded tablets or tablet triturates, moist massing techniques can be used.

The therapeutic can be included in the formulation as fine multiparticulates in the form of granules or pellets of particle size about 1 mm. The formulation of the material for capsule administration could also be as a powder, lightly compressed plugs or even as tablets. The therapeutic could be prepared by compression.

Colourants and flavoring agents may all be included. For example, compounds may be formulated (such as by liposome or microsphere encapsulation) and then further contained within an edible product, such as a refrigerated beverage containing colorants and flavoring agents.

One may dilute or increase the volume of the therapeutic with an inert material. These diluents could include carbohydrates, especially mannitol, alpha-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrants include but are not limited to starch including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic compounds together to form a hard tablet and include materials from natural products such as acacia, tragacanth, starch and gelatin. Others include methylcellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An antifrictional agent may be included in the formulation of the therapeutic to prevent sticking during the formulation process. Lubricants may be used as a layer between the therapeutic and the die wall, and these can include but are not limited to: stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, and Carbowax 4000 and 6000.

Glidants that might improve the flow properties of the compound during formulation and to aid rearrangement during compression might be added. The glidants may include starch, talc, pyrogenic silica and hydrated silicoaluminate.

To aid dissolution of the therapeutic into the aqueous environment, a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethomium chloride. The list of potential nonionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the compounds either alone or as a mixture in different ratios.

Additives which potentially enhance uptake of the compounds are for instance the fatty acids oleic acid, linoleic acid and linolenic acid.

Controlled release formulation may be desirable. The compounds could be incorporated into an inert matrix that permits release by either diffusion or leaching mechanisms i.e., gums. Slowly degenerating matrices may also be incorporated into the formulation. Another form of a controlled release of this therapeutic is by a method based on the Oros therapeutic system (Alza Corp.), i.e. the drug is enclosed in a semipermeable membrane which allows water to enter and push drug out through a single small opening due to osmotic effects. Some enteric coatings also have a delayed release effect.

A mix of materials might be used to provide the optimum film coating. Film coating may be carried out in a pan coater or in a fluidized bed or by compression coating.

Pulmonary Delivery

Also contemplated herein is pulmonary delivery of the compounds. The compounds may be delivered to the lungs of a mammal while inhaling and traverses across the lung epithelial lining to the blood stream.

Contemplated for use in the practice of this invention are a wide range of mechanical devices designed for pulmonary delivery of therapeutic products, including but not limited to nebulizers, metered-dose inhalers, and powder inhalers, all of which are familiar to those skilled in the art.

Some specific examples of commercially available devices suitable for the practice of this invention are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, N.C.; and the Spinhaler powder inhaler, manufactured by Fisons Corp., Bedford, Mass.

All such devices require the use of formulations suitable for the dispensing of the compounds. Typically, each formulation is specific to the type of device employed and may involve the use of an appropriate propellant material, in addition to the usual diluents, adjuvants and/or carriers useful in therapy. Also, the use of liposomes, microcapsules or microspheres, inclusion complexes, or other types of carriers is contemplated.

Formulations suitable for use with a nebulizer, either jet or ultrasonic, will typically comprise the compounds suspended in water. The formulation may also include a buffer and a simple sugar (e.g., for protein stabilization and regulation of osmotic pressure). The nebulizer formulation may also contain a surfactant, to reduce or prevent surface induced aggregation of the compounds caused by atomization of the solution in forming the aerosol.

Formulations for use with a metered-dose inhaler device will generally comprise a finely divided powder containing the compounds suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing the compound and may also include a bulking agent, such as lactose, sorbitol, sucrose, or mannitol in amounts which facilitate dispersal of the powder from the device, e.g., 50 to 90% by weight of the formulation. The compounds (or derivative) should most advantageously be prepared in particulate form with an average particle size of less than 10 microns, most preferably 0.5 to 5 microns, for most effective delivery to the distal lung.

Nasal delivery of the compounds is also contemplated. Nasal delivery allows the passage of the protein to the blood stream directly after administering the therapeutic product to the nose, without the necessity for deposition of the product in the lung. Formulations for nasal delivery include those with dextran or cyclodextran.

Compounds of the present invention should be administered in dosage unit form that is prophylactically and/or therapeutically effective. Dosage unit form as used herein refers to physically discrete units suited as unitary dosages for the subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment sought. Thus the quantity of active compound to be administered will be largely dependent on, the toxicity and specific activity of compound, the subject to be treated and the degree of treatment required. Precise amounts of compound required to be administered may depend on the judgement of the practitioner and may be peculiar to each subject.

It will be appreciated that the composition may be given as a single dose schedule, or preferably, in a multiple dose schedule. A multiple dose schedule is one in which a primary course of delivery may be with 1 to 10 separate doses, followed by other doses given at subsequent time intervals required to maintain or reinforce the treatment. The dosage regimen will also, at least in part, be determined by the need of the individual and the judgement of the practitioner.

In addition, the composition of the present invention containing the non-peptidyl compounds may be administered in conjunction with other agents and compounds, for example, immunoglobulins, sulfonylureas, biguanides, α-glucosidase inhibitors, thiazolidinediones, diazoxide, octreotide, insulin secretogogues as appropriate.

According to a second embodiment, there is provided a method for identifying a non-peptidyl compound possessing ionic and hydrophobic chemical moieties spatially located so as to mimic particular ionic and hydrophobic amino acid residues of insulin which are associated with the binding of insulin to its receptor, said method comprising the steps of: (1) comparing the three dimensional structure of the non-peptidyl compound with a three dimensional pharmacophore of an active site of insulin; and (2) selecting a non-peptidyl compound with ionic and hydrophobic chemical moieties spatially located so as to mimic said site.

Preferably, the active site comprises at least four amino acid residues selected from the group A21 Asn, B21 Glu, A17 Glu, B24 Phe, B25 Phe, A19 Tyr, B12 Val, B16 Tyr, A2 Ile, A3 Val and A1 Gly, with at least one amino acid residue being selected from the group A21 Asn, B21 Glu and A17 Glu. Desirably, the active site comprises one of the following groups of amino acid residues:

1 A21 Asn, B21 Glu, A17 Glu, B24 Phe, B25 Phe;
2 A21 Asn, B21 Glu, B24 Phe, B25 Phe;
3 A21 Asn, B21 Glu, B24 Phe, B25 Phe, A1 Gly, A2 Ile, A3 Val;
4 A21 Asn, B21 Glu, A17 Glu, A19 Tyr, A1 Gly, A2 Ile, A3 Val;
5 A21 Asn, B21 Glu, A17 Glu, B12 Val, A1 Gly, A2 Ile, A3 Val;
6 A21 Asn, B21 Glu, B12 Val, A1 Gly, A2 Ile, A3 Val;
7 A21 Asn, B21 Glu, A17 Glu, B16 Tyr, A1 Gly, A2 Ile, A3 Val;
8 A21 Asn, B21 Glu, A17 Glu, A19 Tyr, B12 Val, B16 Tyr;
9 A21 Asn, B21 Glu, A19 Tyr, B12 Val, B16 Tyr;
10 A21 Asn, B21 Glu, A17 Glu, B24 Phe, B25 Phe, A19 Tyr, B12 Val, B16 Tyr;

11 A21 Asn, B21 Glu, B24 Phe, B25 Phe, A19Tyr, B12 Val, B16 Tyr;

12 A21 Asn, B21 Glu, B24 Phe, B25 Phe, B12 Val, B16 Tyr;

13 A21 Asn, B21 Glu, A17 Glu, B24 Phe, B25 Phe, A19 Tyr;

14 A21 Asn, B21 Glu, B24 Phe, B25 Phe, A19 Tyr;

15 A21 Asn, A17 Glu, B24 Phe, B25 Phe, A19 Tyr;

16 B21 Glu, A17 Glu, B24 Phe, B25 Phe, A19 Tyr;

17 A21 Asn, B21 Glu, A17 Glu, B24 Phe, B25 Phe, B12 Val;

18 A21 Asn, B21 Glu, B24 Phe, B25 Phe, B12 Val;

19 A21 Asn, A17 Glu, B24 Phe, B25 Phe, B12 Val;

20 B21 Glu, A17 Glu, B24 Phe, B25 Phe, B12 Val;

21 A21 Asn, B21 Glu, A17 Glu, B24 Phe, B25 Phe, B16 Tyr;

22 A21 Asn, B21 Glu, B24 Phe, B25 Phe, B16 Tyr;

23 A21 Asn, A17 Glu, B24 Phe, B25 Phe, B16 Tyr;

24 B21 Glu, A17 Glu, B24 Phe, B25 Phe, B16 Tyr;

25 A21 Asn, B21 Glu, A17 Glu, B24 Phe, A19 Tyr, B12 Val, B16 Tyr;

26 A21 Asn, B21 Glu, B24 Phe, A19 Tyr, B12 Val, B16 Tyr;

27 A21 Asn, A17 Glu, B24 Phe, A19 Tyr, B12 Val, B16 Tyr;

28 B21 Glu, A17 Glu, B24 Phe, A19 Tyr, B12 Val, B16 Tyr;

29 A21 Asn, B21 Glu, A17 Glu, B25 Phe, A19 Tyr, B12 Val, B 16 Tyr;

30 A21 Asn, B21 Glu, B25 Phe, A19 Tyr, B12 Val, B16 Tyr;

31 A21 Asn, A17 Glu, B25 Phe, A19 Tyr, B12 Val, B16 Tyr; or

32 B21 Glu, A17 Glu, B25 Phe, A19 Tyr, B12 Val.

Comparison of the three dimensional structure of the non-peptidyl compound with the three dimensional pharmacophore may involve comparison of a minimum energy structure of the non-peptidyl compound with a three dimensional pharmacophore of the active site of insulin, the position of the amino acid residues comprising the active site being determined with reference to crystal and/or NMR solution structures of insulin and its analogues. The three dimensional pharmacophore may incorporate tolerance spheres about the positions of the respective amino acids to reflect the conformational flexibility of insulin.

The positions of the amino acid residues of the active site are defined relative to one another by the following three dimensional coordinates (in hundredths of Angstroms) within tolerance spheres of between 1.5 and 5 Å: B12 Val (343.9, 157.2, −242.6); B25 Phe (113, −5.3, 780.8); B24 Phe (92.9, 569.7, 43.2); B16 Tyr (361.8, 1068, −467.5); B21 Glu (−84.9, 1711.2, 99.6); A17 Glu (−1079.2, 1005.6, −67.9); A19 Tyr (−763.8, 49.2, −4.1); A21 Asn (−344.2, 908, 677.9); A1 Gly (−870.2, −574.9, 127.9); A2 Ile (−489.8, −30, −218.1); and A3 Val (−237.6, −703.3, −348.4).

In a more specific embodiment of the present invention, the tolerance spheres for each residue are as follows: 5 Å for residues B24 Phe, B25 Phe, A17 Glu, B21 Glu, A21 Glu, A1 Gly, A2 Ile; 3.6 Å for residues A19 Tyr, B16 Tyr, B12 Val and 3 Å for A3 Val.

An efficient means to select a non-peptidyl insulin mimetic compound from a potentially large number of non-peptidyl compounds involves comparing non-peptidyl compounds against a three dimensional pharmacophore of insulin using a computer program, for example Catalyst (MSI), to screen one or more computerised databases of three dimensional chemical structures of non-peptidyl compounds.

If, for example, the Catalyst program is used, the amino acids in the active site are preferably represented by the following Catalyst defined features: B12 Val—hydrophobic; B25 Phe—hydrophobic; B24 Phe—hydrophobic; B16 Tyr—hydrophobic; B21 Glu—negative ionisable; A17 Glu—negative ionisable; A19 Tyr—hydrophobic; A21 Asn—negative ionisable; A1 Gly—positive ionisable; A2 Ile—hydrophobic; and A3 Val—hydrophobic.

Preferably still, the amino acid residues represented within Catalyst as hydrophobic may be further specified as: B12 Val—aliphatic; B25 Phe—aromatic; B24 Phe—aromatic; B16 Tyr—aromatic; A19 Tyr—aromatic; A2 Ile—aliphatic; and A3 Val—aliphatic.

According to a third embodiment, there is provided a method for determining whether a non-peptidyl compound identified by the third embodiment of the invention is an agonist or an antagonist, said method comprising the step of: exposing the compound to an insulin or insulin like receptor and measuring the change in biological activity following exposure of the compound to the receptor.

Best Method of Performing the Invention

Further features of the present invention will be more fully described in the following Examples. It is to be understood, however, that this detailed description is included solely for the purposes of exemplifying the invention, and should not be understood in any way as a restriction on the broad description as set out above.

Pharmacophore Construction and Use for Database Searching

Models of Insulin used for Pharmacophore Construction

Many crystal and NMR-solution structures of insulin and its analogues have been published. The NMR solution structure pdblhiu.ent was chosen from the Brookhaven protein database to allow for flexibility of the insulin molecule in solution. Additionally, because the insulin crystal structure is reported to be an inactive "closed" conformation and that an "open" conformation, represented by glycine [B24] insulin, is active, the NMR solution structure, pdb1hit, of Gly[B24]insulin was also chosen for pharmacophore construction. The pdb1hiu.ent file contained a collection of eleven models (MODEL 1 through MODEL 11) while the glycine mutant contained nine models (MODEL 0 through MODEL 8). Each structure represented a possible solution conformation of the molecule that satisfies the NMR distance data.

Model Analysis

The eleven native insulin models (HIU 1–11) were overlaid with each other and an average structure was determined. This structure was processed by fixing the alpha carbons and subjecting it to 100 steps of Steepest Descent minimisation (using CHARM force field) to normalise the slightly distorted coordinates of the rest of the molecule. This same procedure could not be used with the glycine analog due to the larger variation among the structures; therefore each model was extracted as a separate molecular structure file. Since the pharmacophore is based upon the native structure of insulin, each glycine model was re-mutated back to Phenylalanine at position B24 using QUANTA's Protein Design facility. The conformation of the phenylalanine side chain was adjusted to minimise bad contacts and the side chain rotamer most likely to be found by Karplus rules was assigned. The structures were then analysed for their degree of "openness" by measuring the distance between a pseudo atom (placed between residues A2 and A3) and residue B25. The average native insulin structure and two glycine mutant structures HIT3 and HIT4 were chosen to represent a range of "openness' in insulin conformations.

In QUANTA, the following residues from each model structure were selected: A21 Asn, B21 Glu, A17 Glu, B24 Phe, B25 Phe, A19 Tyr, B12 Val, B16 Tyr, A2 Ile, A3 Val and A1 Gly. The remainder of the molecule was removed and residues were connected with virtual "bonds". The coordinates of these pseudo structures were then imported into the Catalyst (MSI) software program and pharmacophore construction was conducted by mapping features (negative ionisable, positive ionisable, hydrophobic) onto the residues. Original structures were then overlayed onto the hypothesis to estimate tolerance spheres about each feature. The pharmacophore is shown in FIG. 1. The pharmacophore was then used to create subsets of features (Hypotheses) that were used to screen databases. FIG. 2 shows the thirteen working hypotheses generated—including variations used for database searching. A maximum 5 Å tolerance was assigned where the variation of side chains about a feature was large. The tolerances about each feature are shown in FIG. 3. Smaller 3 Å tolerance spheres were used for all HIT3 and HIT4 models. In subsequent searches all features were given identical tolerance spheres and the size of these were adjusted from a maximum of 5 Å to a minimum of 1.5 Å to limit the number and quality of compounds identified.

These hypotheses were then used to rapidly screen chemical databases—that contained representative three-dimensional structures of each compounds likely minimum energy conformations, for those compounds that contained specific functional groups that could be positioned in the tolerance spheres of each hypothesis.

Results

Hypotheses 2 and 7a, with the tolerances about each of the features of the hypotheses (negative ionisable, positive ionisable and hydrophobic) as listed in FIG. 3 identified the following compounds:

| Compound | Ref. used herein |
|---|---|
| 4,4'-Methylenebis[3-hydroxy-2-naphthalenecarboxylic acid] | IM 025 |
| 7-[3-(4-acetyl-2-ethyl-5-hydroxyphenoxy)propoxy]-3,4-dihydro-8-propyl-2H-1-benzopyran-2-carboxylic acid | IM 071 |
| 2,4-dichloro-6-(N-(trifluoromethanesulfonyl))sulfamoylphenyl 3,5-dichloro-2-hydroxybenzenesulfonate | IM 103 |
| 7-[(4-acetyl-3-hydroxy-2-propylphenyl)methoxy]-4-oxo-8-propyl-4H-1-benzopyran-2-carboxylic acid. | IM 127 |
| 7-[3-(4-acetyl-3-methoxy-2-propylphenoxy)propoxy]-3,4-dihydro-8-propyl-2H-1-benzopyran-2-carboxylic acid | IM 129 |
| 3,4-dihydro-8-propyl-7-[[3-[2-ethyl-5-hydroxy-4-(1H-pyrazol-3-yl)phenoxy]propyl]oxy]-2H-1-benzopyran-2-carboxylic acid | IM 132 |
| 3,4-dihydro-8-propyl-7-[[3-[2-ethyl-5-hydroxy-4-ethoxyphenoxy]propyl]oxy]-2H-1-benzopyran-2-carboxylic acid | IM 134 |
| 3-[4-[7-carboxy-9-oxo-3-[3-[2-ethyl-4-(4-fluorophenyl)-5-hydroxyphenoxy]propoxy]-9H-xanthene]]propanoic acid | IM 140 |
| 8-propyl-7-(quinol-2'-ylmethoxy)-3,4-dihydro-2H-1-benzopyran-2-carboxylic acid | IM 143 |
| 7-(naphth-2'-ylmethoxy)-8-propyl-3,4-dihydro-2H-1-benzopyran-2-carboxylic acid | IM 144 |
| N-(trifluoromethanesulfonyl)-3,5-dinitro-4-(N',N'-dipropylamino)benzenesulfonamide | IM 145 |

-continued

| Compound | Ref. used herein |
|---|---|
| 8-propyl-7-[3-[4-(4-fluorophenyl)-2-ethyl-5-hydroxyphenoxy]propoxy]-3,4-dihydro-2H-1-benzopyran-2-carboxylic acid | IM 171 |
| 3,4-dihydro-7-[[6-(4-methoxyphenyl)hexenyl]oxy]-8-propyl-2H-1-benzopyran-2-carboxylic acid | IM 172 |
| 8,8'-[Carbonylbis[imino-3,1-phenylenecarbonylimino(4-methyl-3,1-phenylene)carbonylimino]]bis-1,3,5-naphthalenetrisulfonic acid | IM 175 |

IM 175 was identified by a number of hypotheses. The number of hypotheses that identified IM 175 depended upon the tolerances of features within each hypothesis. FIG. 4 shows the multiple hypotheses that identified compound IM 175 and the tolerances of features in each hypothesis.

For each of the identified compounds, tests were undertaken to demonstrate their ability to compete for insulin binding in a variety of insulin receptor preparations.

Further tests were undertaken to ascertain their ability to stimulate the insulin receptor second messenger system and their ability to effect insulin's stimulation of its second messenger system. This was determined in three assays: the compounds ability to stimulate: insulin receptor autophosphorylation; phosphorylation of a synthetic peptide that is a substrate of the insulin receptor β-subunit associated tyrosine kinase activity and glucose transport in 3T3L1 adipocyte cells. Furthermore, in vivo tests were undertaken to ascertain their ability to lower blood glucose levels in experimentally induced diabetic mice.

Solubility of Compounds

Compounds were solubilised in a minimal volume of DMSO before diluting into the relevant assay buffer. Final assay concentrations of DMSO were kept to less than 1% (volume/volume) and assays were controlled for any effect of the residual DMSO.

For in vivo studies compounds were dissolved in a sterile solution of 1.6% glycerin, 0.25% m-cresol, pH 6.75.

Insulin Binding Assay

The Hepes buffer system used to dilute the compound depended on the source of insulin receptor preparation used for each assay:

Human Placental Plasma Membranes—50 mM Hepes, pH 7.8 @ 4 C containing 100 U/mL Bacitracin; CHO cells transfected with human insulin receptor (CHO.T11)—Hams media supplemented with 25 mM Hepes, pH 7.8 @ 4° C. and 0.1% BSA; Wheat germ agglutinin affinity purified insulin receptors, insulin affigel affinity purified receptors— 50 mM Hepes, pH 7.8 @4° C. containing 100 U/mL Bacitracin and 0.02% Triton-X 100.

Where possible, compounds were prepared in the absence of DMSO because DSMO concentrations greater than 0.05% DMSO effects insulin binding to its receptors.

One hundred microlitres of compound was mixed on ice with 50 μL of assay buffer containing 5 fmole of $^{125}$I insulin ($7 \times 10^7$ MBq·mmol$^{-1}$) and 50 μL of insulin receptor solution. Tubes were mixed and incubated for 16 h at 4° C. After the incubation, the tubes were placed on ice and 300 μL of a 1:5 suspension of 0.4% bovine-γ-globulin in 20% polyethyleneglycol 6000 (BDH chemicals) was added to each tube, mixed thoroughly and left to incubate for 30 min on ice. The tubes were then centrifuged (3,000 g) for 30 min at 4° C., the supernatant was aspirated off and the pellet counted for radioactivity. The ability of each compound to compete for $^{125}$I insulin binding to each of the receptor sources was compared to unlabelled human insulin. Inhibition constants were estimated by graphical analysis of displacement plots or calculated using the curve fitting programs EBDA and/or LIGAND.

Activation of Insulin Receptor Second Messenger System

The activity of each of the compounds was evaluated in three assays of insulin action: 1) Insulin receptor autophosphorylation; 2) Phosphorylation of a synthetic substrate specific for insulin receptor (PTK assay) and 3) glucose uptake by 3T3L1 adipocyte cells.

Insulin Receptor Phosphorylation

Insulin receptor phosphorylation was assessed using a modification of the method described by Li et al. (21). Insulin receptors prepared from CHO cells stably expressing full-length insulin receptors (CHO.T11) (15 µL) were pre-incubated at room temperature for 20 minutes with 7.5 µL of 50 mM HEPES, pH 7.4 containing 150 mM NaCl, 0.1 mM phenylmethylsulfonylfluoride, 10 mM MgCl2, 2 mM MnCl2 and 0.1% Triton X-100 and varying concentrations of human insulin or putative insulin mimetic compound. After this preincubation, 2.5 µL of 1 mM ATP, 100 mM sodium orthovanadate and 5 µCi of [$\gamma$-$^{32}$P]ATP were added and incubated at room temperature for 25 minutes. The reaction was terminated by the addition of 1.5 µL of 0.5 M EDTA and 3.5 µL of 1.5 M NaCl. The solution was then either solubilised and resolved by SDS-PAGE or immunoprecipitated using anti-insulin R$\beta$ (29B4) mouse monoclonal IgG or anti-phosphotyrosine (PY20) mouse monoclonal IgG (Santa Cruz Biotechnology Inc., USA), solubilised and then resolved by SDS-PAGE. Immunoprecipitation was performed by incubating one microgram of antibody with the reaction mixture over night at 4° C. Following this incubation, 40 µL of protein A Sepharose CL-4B (Pharmacia Biotech AB, Sweden) in a 75%:25%(v/v) slurry with 50 mM Tris, pH 7.5 containing 150 mM NaCl (TBS) was added to the receptor-antibody mix and incubated for a further 90 minutes at 4° C. with continuous stirring. The receptor-antibody-Sepharose complex was separated from the supernatant by centrifugation at 7,500 g for 5 minutes. The pellet was washed three times in TBS containing 0.1% Triton X-100 and 10 µL of 0.1 M glycine, pH 3.3 was added. The solution was then solubilised by incubation for 5 minutes at 100° C. in 10 µL of 80 mM Tris-HCl, pH 6.8 containing 0.45 M DTT, 56 mM EDTA, 30% sucrose and 6% SDS. Following centrifugation for 5 minutes at 7,500 g, the supernatant was resolved on a 7.5% SDS polyacrylamide gel. The gel was dried under vacuum and exposed to X-ray film. In some instances, gel bands corresponding to 90 kDa were excised and the associated radioactivity was measured by suspending the gel band in 2.5 mL of Scintillation fluid (Beckman) using a Beckman $\beta$-counter.

Protein Tyrosine Kinase (PTK) Assay

Protein tyrosine kinase activity was determined using a modification of the method of N. Konstantopoulos (22). The assay involved measuring the effect of compounds on the insulin receptor mediated incorporation of $^{32}$P into a specific synthetic peptide substrate (RRDIFETDYFRK), (FYF peptide).

The assay was commenced by adding 5 µL of an insulin receptor solution in 50 mM Hepes, pH 7.5 to: 5 µL of the test compound in 50 mM Hepes, pH 7.5; 5 µL of FYF peptide in 40 mM imidazole pH 7.3 containing 40 mM $\beta$-glycerophosphate, 1 mM EGTA, 100 mM MgCl$_{2, 5}$ mM MnCl$_2$ and 0.05% BSA; 5 µL of phosphorylation mixture containing 0.1 mM ATP, 0.5 mM sodium vanadate and 0.5 µCi of [$\gamma$-$^{32}$P]-ATP and; 5 µL of a 50 mM Hepes, pH 7.5 solution alone or containing 2 µM insulin. The reaction was allowed to proceed for 20 minutes at 30° C. before it was terminated by the addition of 12.5 µL of 7.5 M guanidine hydrochloride. An aliquot (10 µL) of the reaction mixture was then spotted onto a Whatman 81 phosphocellulose paper (15 mm×15 mm), washed three times (2 min per wash) in about 50 mL of 30% acetic acid, 0.05% orthophosphoric acid then finally, with one wash in about 200 mL of water. The papers were then rinsed briefly (15 sec) in 95% ethanol, dried, suspended in 2.5 mL of scintillation fluid (Beckman) and counted for radioactivity in a Beckman $\beta$-counter.

Glucose Transport in 3T3-L1 Cells

Glucose transport was determined using a modification of the method of S. J. Isakoff et at. (23). The assay involved measuring the effect of compounds on the uptake of $^3$H-deoxyglucose into 3T3L1 adipocyte cells.

Growth and Differentiation of 3T3-L1 Cells

The cell line, 3T3-L1, derived from mouse embryo fibroblasts, was grown in 250 mL tissue culture flasks containing 15 mL medium made up of DMEM (Dulbecco's modified Eagle's medium containing glutamine, 2 mM; sodium bicarbonate, 30 mM; penicillin 71.5 mg/litre; streptomycin, 152.5 mg/litre) supplemented with 10% foetal calf serum (FCS), pH 7.4. Cells were maintained in a humidified incubator at 37° C. in a 5% CO$_2$ environment. The medium was changed every 3 days and the cells were split when they were about 70–80% confluent.

3T3-L1 fibroblast cells from one tissue culture flask were suspended in 50 mL of DMEM media containing 10% FCS and 0.5 mL of this suspension were seeded into each well of two 48-well tissue culture plates. The differentiation of the cells was initiated when the fibroblast cells were fully confluent. Routinely, differentiation was induced on cells that had been growing in tissue culture plates for 4–5 days. Cells were exposed to 0.5 mL of DMEM medium containing 10% FCS, 2 µg/mL insulin, 0.1 µg/mL dexamethasone, 0.5 mM isobutylmethylxanthine and 1 µg/mL biotin for three days. Cells were then incubated a further three days in 1 mL of post differentiation DMEM medium containing 10% FCS and 2 µg/mL insulin. The cells were subsequently maintained with DMEM medium containing 10% FCS. The differentiated cells were examined microscopically between 11 and 13 days after differentiation to ensure they displayed the adipocyte phenotype.

Glucose Transport Assay

One day prior to the glucose transport assay, cell medium was replaced with DMEM containing 10% charcoal-treated foetal calf serum (CTFCS). On the day of the assay, the medium was aspirated and each well was washed with 1 mL of 25 mM Hepes, pH 7.4 containing 0.9% NaCl (NaCl-HEPES). One hundred microlitres of NaCl-HEPES buffer in the absence and presence of 2 nM insulin and/or test compound was then added to wells and left to incubate for 20 min at 37° C. Ten microlitres of NaCl-HEPES containing 3 mM 2-deoxy-D-glucose and 0.1 µCi 2-deoxy-D-[1-$^3$H] glucose were then added. Following a 10 min incubation at 37° C., the medium was aspirated off and the wells rapidly washed three times with 1 mL of ice-cold 50 mM phosphate, pH 7.5 containing 150 mM NaCl (PBS) and 10 mM glucose. Two hundred microlitres of 3% Triton X-100 was then added to each well and left to incubate for a minimum of 10 minutes. One hundred microlitres of the solubilised cells was then added to 2.5 mL of liquid scintillation fluid and counted for radioactivity in a Beckman $\beta$-counter.

Figure 5:
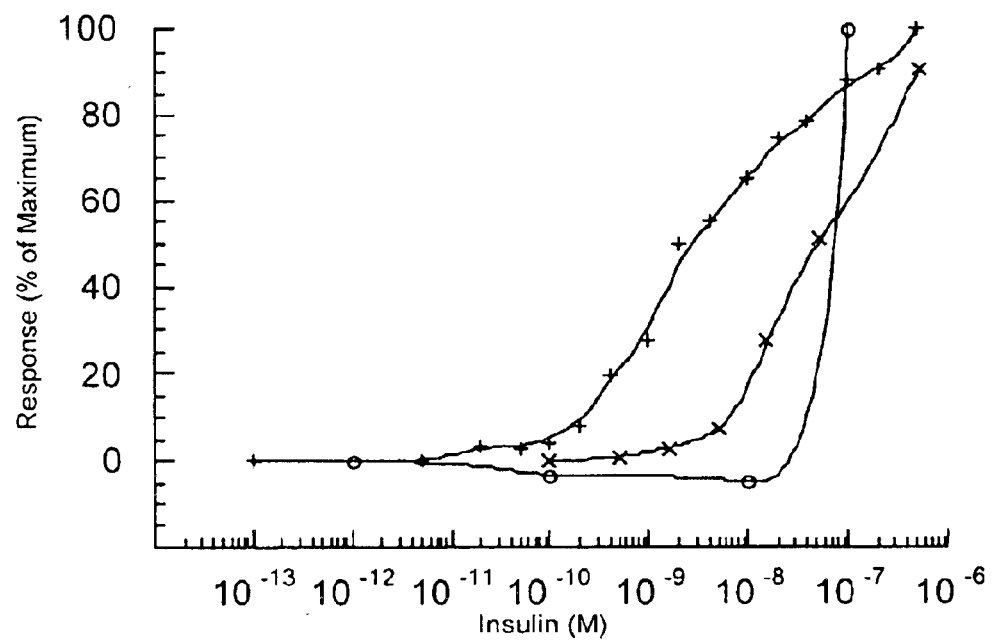
FIG. 5 illustrates dose response of assays versus insulin concentration, showing typical dose response curves of Glucose transport (+), PTK assay (x) and Autophosphorylation experiments (○), which are expressed as a percent of maximal assay activation over a range of insulin concentrations.

FIG. 5 illustrates that dose response curves of insulin are clearly different in each of the three assays used to classify compounds. These differences have been reported previously in assays that measure the signalling and metabolic actions of insulin. For example, M. A. Soos et al. (24) showed that the half maximal insulin concentration for stimulation of $^3$H-deoxyglucose was 0.1 nM in NIH 3T3 HIR3.5 cells which is 30 fold lower than that reported for receptor phosphorylation. They also studied a number of insulin mimetic monoclonal anti-insulin receptor antibodies and showed differential stimulation of 2-deoxyglucose uptake in NIH 3T3 HIR3.5 cells (100%), [$^3$H]thymidine incorporation (30%) and $^{32}$P incorporation into insulin receptor β-subunit (0%). However, a later publication showed that in using a more sensitive assay for receptor autophosphorylation, the same antibodies stimulate phosphorylation of the insulin receptor β-subunit (25). The differences between assays is not clearly understood but may be due in part to differences in temperature and incubation times of the experiments (24). However, it is also recognised that there are substantial differences between whole cell and broken cell preparations (25). For these reasons it is necessary to characterise each compound in a number of assays.

In vivo Studies

Induction of Experimental Diabetes

Six week old male CD-1 mice were injected intra peritoneally with a sterile solution of streptozotocin prepared in 100 mM citrate buffer, pH 4.65 at a dose of 200 mg/kg and an injection volume of 16.7 mL/kg. Mice were housed in a 12 h light/dark cycle and fed a normal chow diet ad libitum. Drinking water was supplemented with 5% sucrose for the first two days following streptozotocin injection before being replaced with tap water thereafter. After 4 days, blood was taken from the saphenous vein of the mice using the method of Hem, A et al. (26). Random non-fasting blood glucose levels were determined on venous blood using an esprit glucometer (Bayer). Mice with blood glucose levels of greater than 15 mmol/L were characterised as diabetic.

Blood Glucose Level Measurement

Blood glucose levels of mice were determined, followed by an intra peritoneal dose of IM compound dissolved in diluent (1.6% glycerin, 0. 25% m-cresol, pH 6.75). Mice were then bled periodically and whole blood glucose levels were determine using a one-touch esprit glucometer (Bayer). The ability of compounds to lower blood glucose levels was compared at each time point to mice injected with diluent alone (negative control) and those injected with a 2 U/kg intra peritoneal dose of human insulin (positive control).

Antagonist Compounds

The following compounds have been classified as antagonists of insulin action: IM 025, IM 071, IM 127, IM 129, IM 132, IM 134, IM 143, IM 144, IM 145, IM 171 and IM 172). Some of these compounds show synergism with insulin, which is detailed in individual cases below.

IM 129 shows experimental data characteristic of the other IM compounds listed above. These characteristics are detailed below. All other IM antagonist compounds are included thereafter with minimum discussion, unless explanation of an extraordinary result is required.

EXAMPLE 1

7-[3-(4-Acetyl-3-methoxy-2-propylphenoxy) propoxy]-3,4-dihydro-8-propyl-2H-1-benzopyran-2-carboxylic acid sodium salt hydrate (IM 129)

This compound may be synthesised by the method described by S. W. Djuric et al. (27), incorporated herein by reference.

Effect on Insulin Binding

Figure 6:
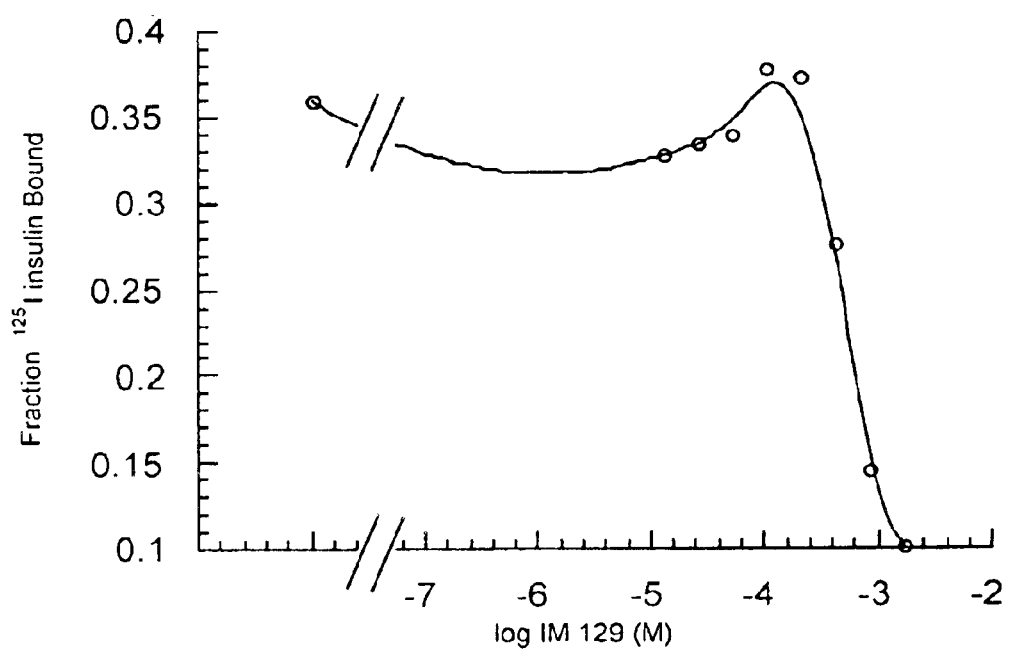
FIG. 6 summarises the effect of IM 129 on $^{125}$I insulin bound to human placental plasma membranes (○) that is expressed as a fraction of total $^{125}$I insulin added, and where each data point is the mean of a triplicate determination.
Figure 7:
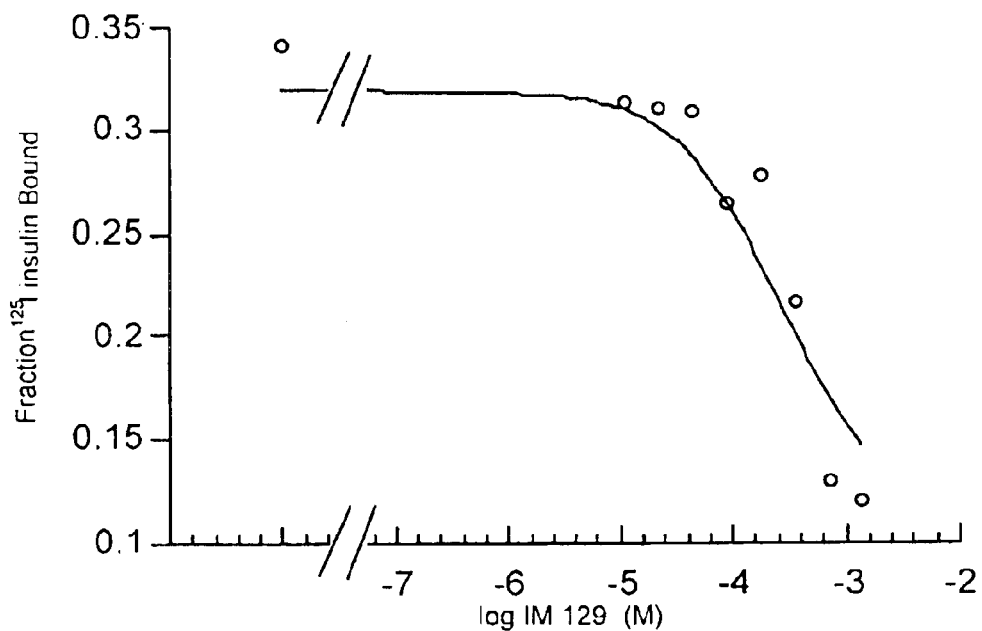
FIG. 7 demonstrates the effect of IM 129 on $^{125}$I insulin bound to WGA.IR (○) which is expressed as a fraction of total $^{125}$I insulin added and overlayed with a 1-site fit to the data (solid line), and where each data point is the mean of a triplicate determination.

IM 129 competes with insulin for binding to a number of receptor sources. Displacement plots from competition studies conducted using membrane-bound receptor preparations display a characteristic skewed bell-shaped isotherm with a peak in $^{125}$I insulin binding at about 100 to 200 μM. At higher concentrations, IM 129 inhibits insulin binding with an apparent Ki between 320 μM and 550 μM. A typical displacement plot from four separate experiments can be seen in FIG. 6. In contrast, purified receptor preparations yield a less complicated displacement plot with an estimated Ki of 189 μM (LIGAND, 1-site fit), as can be seen in FIG. 7, which is consistent with observed differences in insulin binding to membrane-associated and soluble receptor preparations described in the background art.

Effect on Biological Activity

Figure 8:
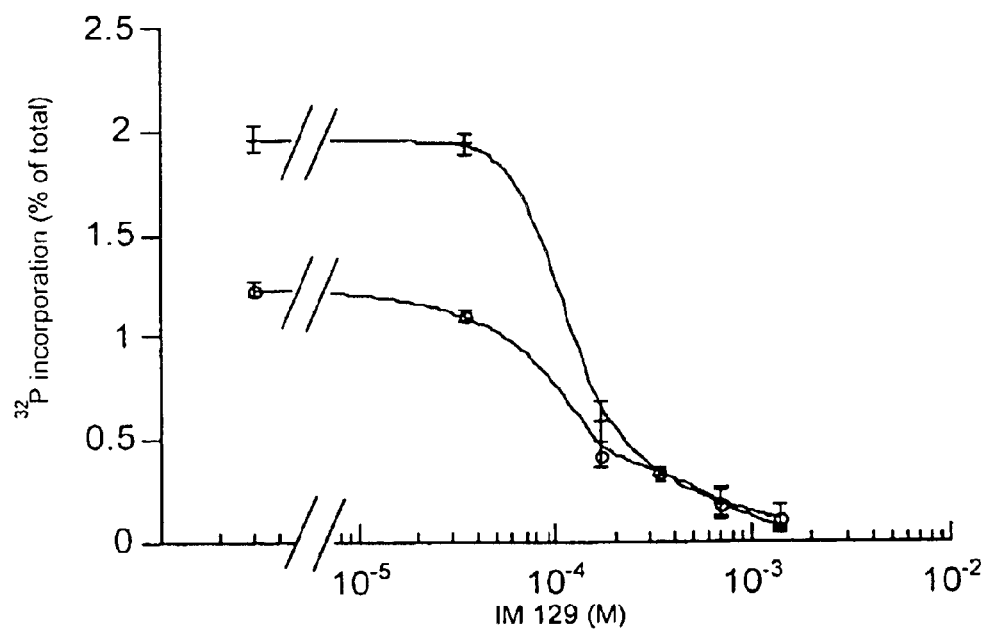
FIG. 8 illustrates the effect of IM 129 on total (in the presence of 50 nM insulin) (+) and basal (absence of insulin) (○) $^{32}$P incorporation into FYF peptide expressed as a percentage of total $^{32}$P-γ-ATP added to reactions, where each data point is the mean of a duplicate determination±one standard deviation.
Figure 9:
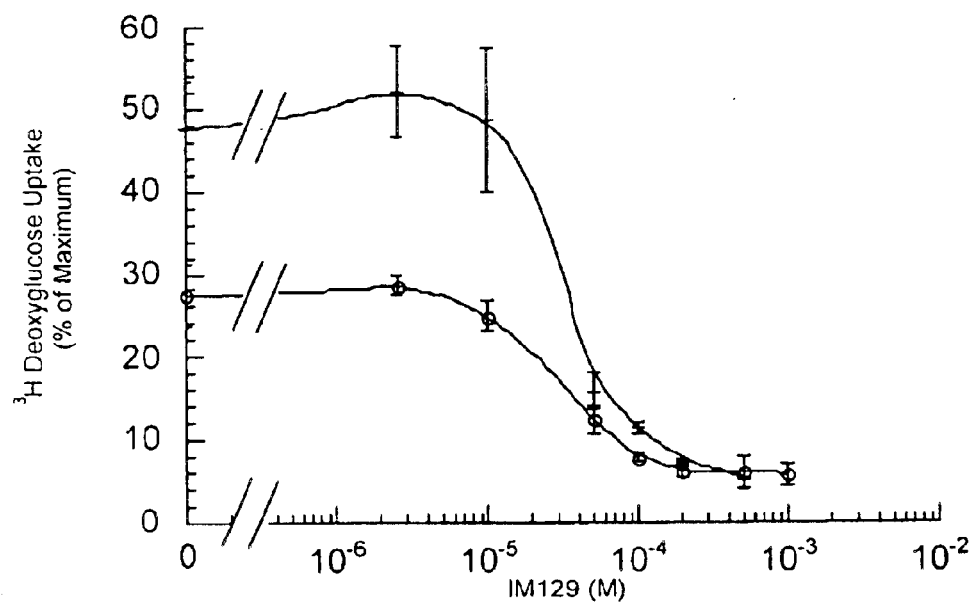
FIG. 9 shows the effect of IM 129 on total (presence of 2 nM insulin) (+) and basal (no insulin) (○) $^3$H-deoxyglucose uptake by 3T3L1 cells, where glucose transport is expressed as a percentage of a maximal 100 nM dose of insulin, and where each point is the mean of a triplicate determination±one standard deviation.

The dose response curves of IM 129 in several biological assays indicate that it is an antagonist of insulin action with an apparent IC$_{50}$ between 30 and 200 μM, as illustrated by FIGS. 8 and 9.

Figure 10:
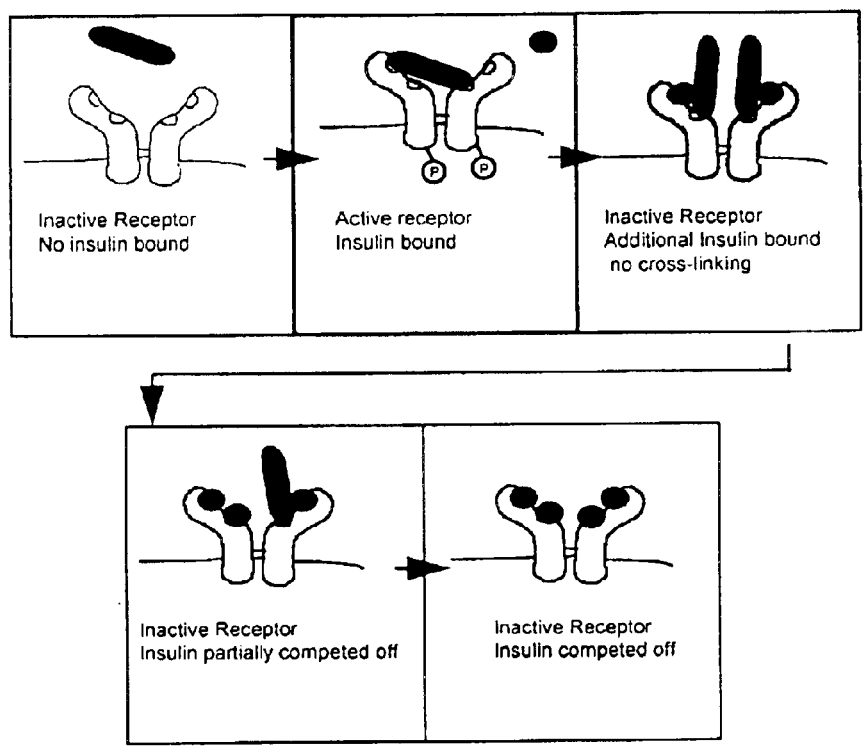
FIG. 10 represents a proposed model of antagonist competition with insulin for binding to insulin receptors, in which two alpha-beta halves of the insulin receptor joined by disulfide bonds are illustrated, activated receptors are phosphorylated on their β-subunits, insulin is illustrated by oblong shaped objects and in which antagonist molecules are illustrated by black circular objects.

The difference between the apparent Ki estimated from insulin binding and biological assays appears to be an artefact of the skewed bell-shaped displacement plots obtained in binding experiments. Mechanistically, this is likely to be caused by a complex competition between the compound and insulin for the multiple binding sites on the insulin receptor. FIG. 10 shows a possible model for receptor activation that is consistent with P. De Meyts (14) and L. Schaffer (15) models, where insulin receptors are activated through cross-linking of two sites on each α-subunit as discussed earlier. Receptor deactivation occurs when cross-linking is disturbed by the antagonist, the inhibition constant of which is measured in biological assays. However, the inhibition constant measured in biological assays correlates with an increase in bound tracer insulin in binding experiments (Bell-shaped curve), which indicates that an additional insulin molecule is accommodated in the binding site. This may occur because the receptor binding site is no longer obstructed by a cross-linked insulin molecule or a compound induced conformational change occurs. In fact, insulin itself induces just such a change at its binding site, accommodating one molecule at physiological concentrations, a second at greater than 100 nM and even a third molecule at supra physiological concentrations of insulin. As a result of the additional tracer insulin bound, higher concentrations of compound are then required to compete off the bound insulin, leading to a higher apparent inhibition constant observed in insulin binding assays compared with biological assays.

Specificity

Figure 11:
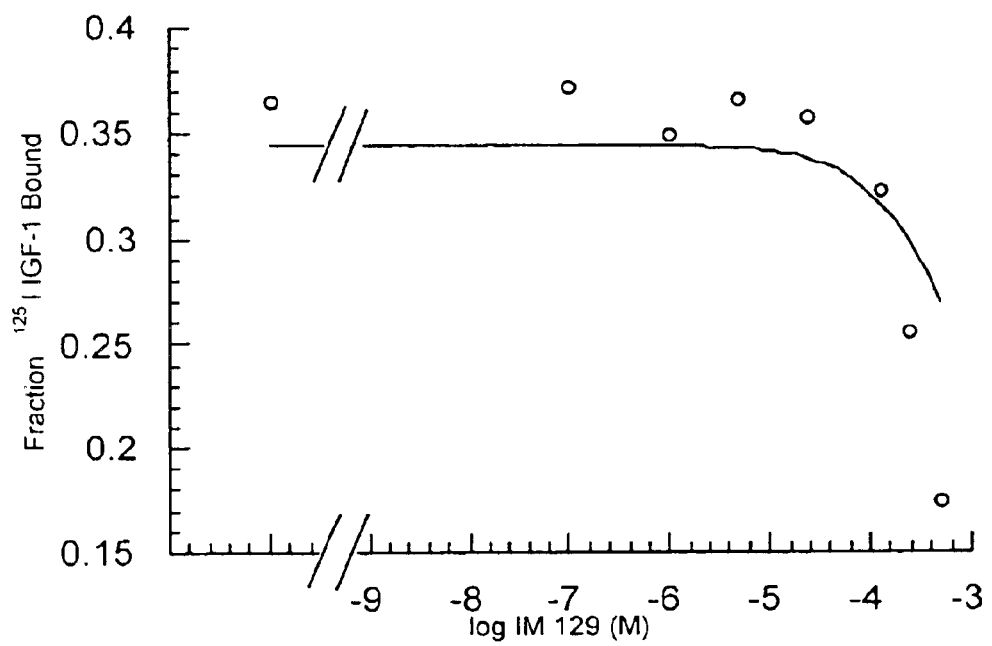
FIG. 11 shows the effect of IM 129 on $^{125}$I IGF-1 bound to human placental plasma membranes (○) which is expressed as a fraction of total $^{125}$I IGF-1 added and is overlayed with a 1-site fit to the data (solid line) and where each data point is the mean of a triplicate determination.

IM 129 displaces $^{125}$I IGF-1 binding from human placental plasma membranes (HPPM) in a dose dependent manner with an apparent Ki of 0.8–1.3 mM, as illustrated by FIG. 11. This is approximately two fold higher than the apparent Ki for $^{125}$I insulin binding for the same source of receptors. Therefore, IM 129 has different specificity for the two receptors and is a less potent inhibitor of $^{125}$I IGF-1 binding than it is for $^{125}$I insulin binding.

EXAMPLE 2

4,4'-Methylenebis[3-hydroxy-2-naphthalenecarboxylic acid] (IM 025)

4,4'-Methylenebis[3-hydroxy-2-naphthalenecarboxylic acid] is commercially available from the Sigma Chemical Company.

Effect on Insulin Binding

Figure 12:
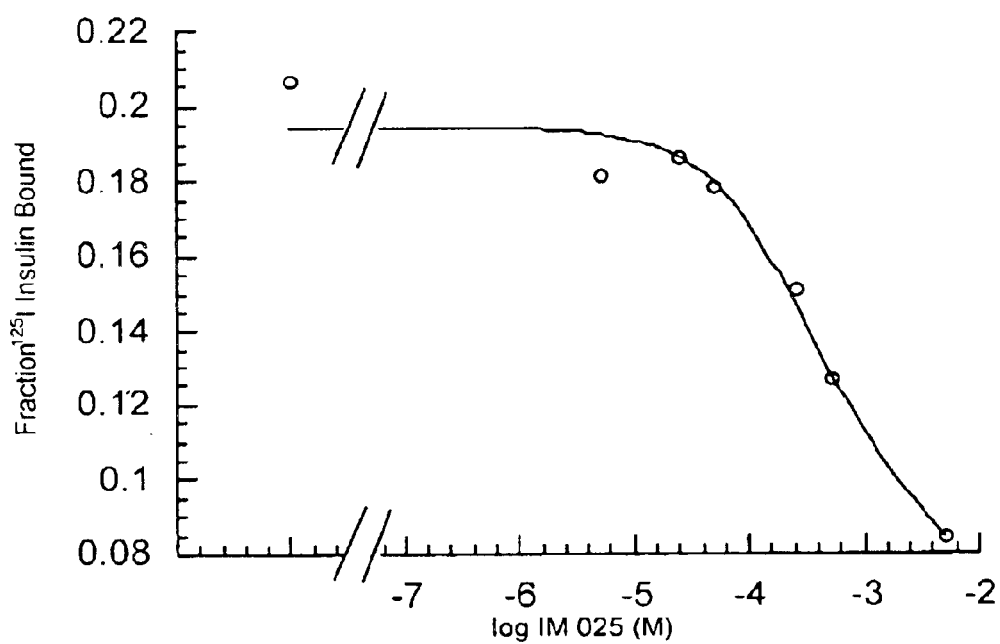
FIG. 12 illustrates the effect of IM 025 on $^{125}$I insulin bound to human placental plasma membranes (○) which is expressed as a fraction of total $^{125}$I insulin added, and where each data point is the mean of a triplicate determination.
Figure 13:
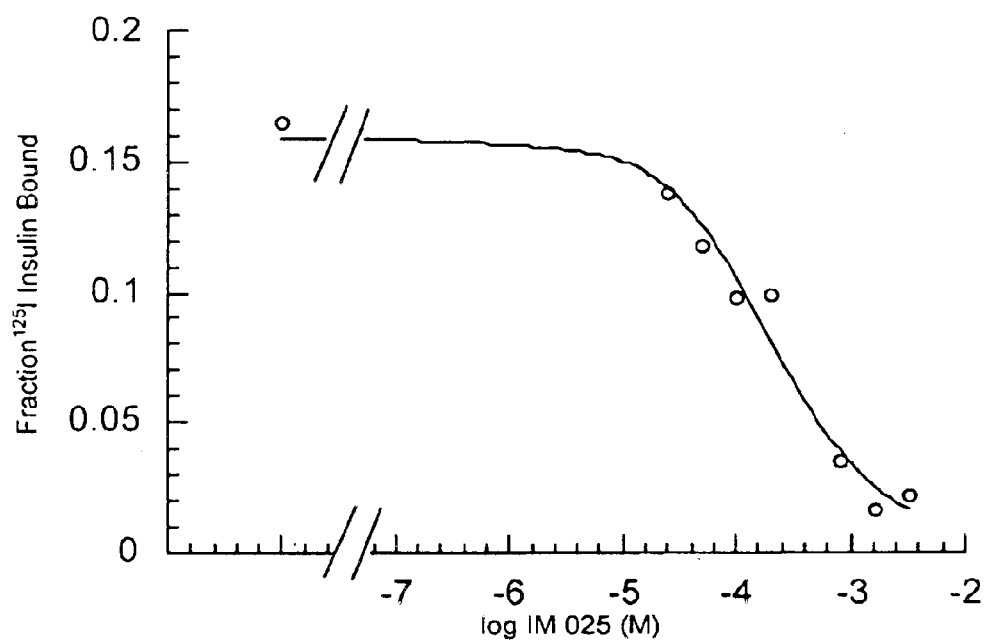
FIG. 13 summarises the effect of IM 025 on $^{125}$I insulin bound to CHO.T11 cells (○) which is expressed as a fraction of total $^{125}$I insulin added and overlayed with a 1-site fit to the data (solid line), and where each data point is the mean of a triplicate determination.
Figure 14:
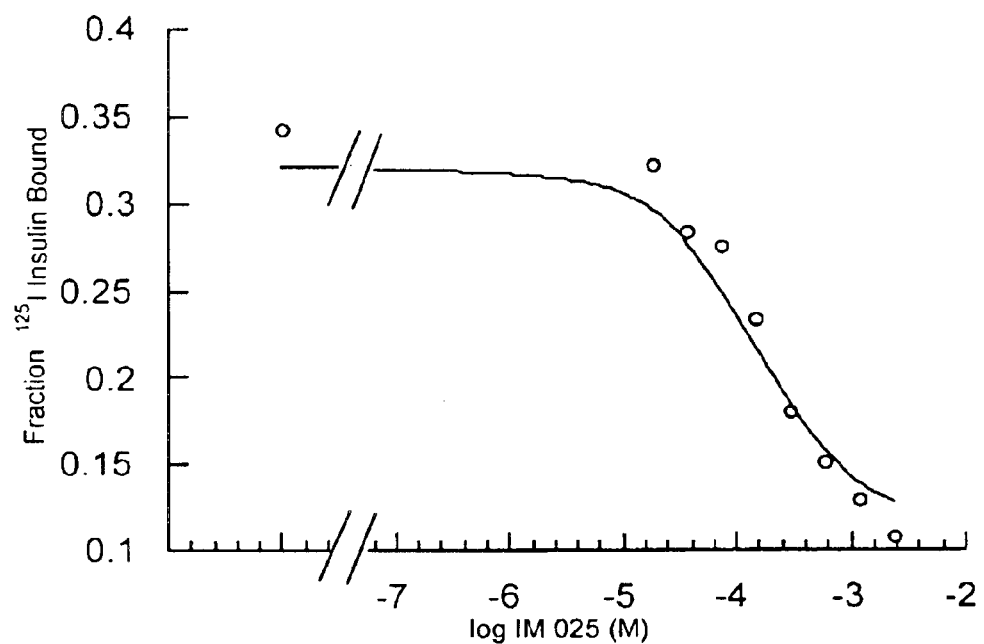
FIG. 14 illustrates the effect of IM 025 on $^{125}$I insulin bound to WGA.IR (○) which is expressed as a fraction of total $^{125}$I insulin added and overlayed with a 1-site fit to the data (solid line), and where each data point is the mean of a triplicate determination.

IM 025 competes with insulin binding to insulin receptors from a number of sources with an estimated Ki of 100–400 µM, as seen in FIGS. 12 to 14. FIG. 12 shows a typical competition experiment of IM 025 on $^{125}$I insulin binding to human placental plasma membranes. The calculated Ki over 5 experiments is 335 µM±34 µM. FIG. 13 shows a typical competition experiment of IM 025 on $^{125}$I insulin binding to CHO.T11 cells. The estimated Ki is 137–337 µM (LIGAND, 1-site fit) over two experiments. FIG. 14 shows a typical competition experiment of IM 025 on $^{125}$I insulin binding to WGA.IR. The estimated Ki is 108±32 µM (LIGAND, 1-site fit).

Effect on Biological Activity

Figure 15:
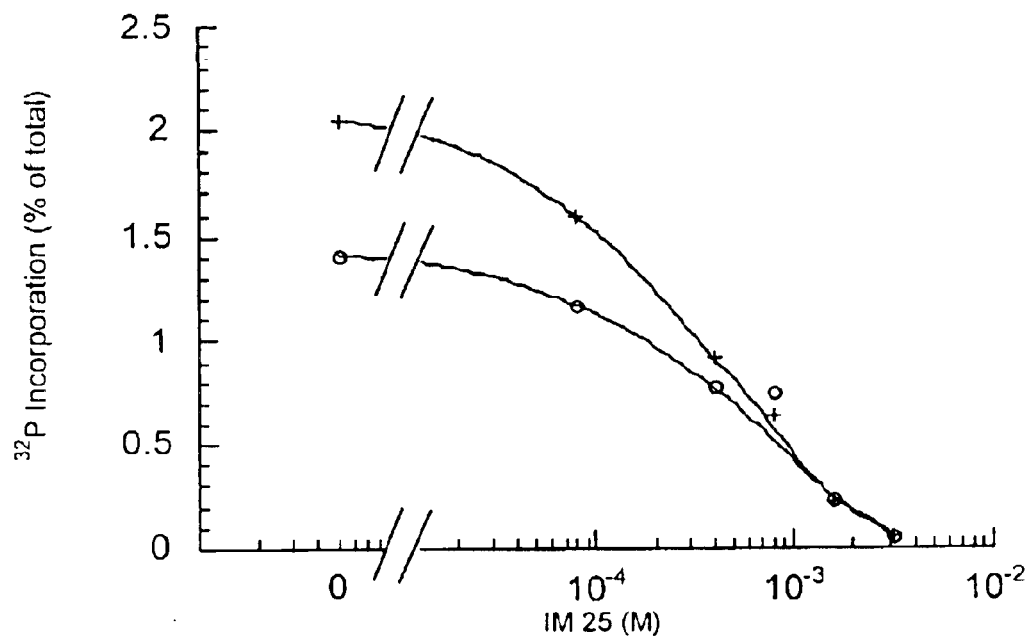
FIG. 15 demonstrates $^{32}$P incorporation into FYF peptide where the effect of IM 025 on total (+) and basal (○) $^{32}$P incorporation into FYF peptide is expressed as a percentage of total $^{32}$P-γ-ATP added to reactions, and where each data point is the mean of a duplicate determination.
Figure 16:
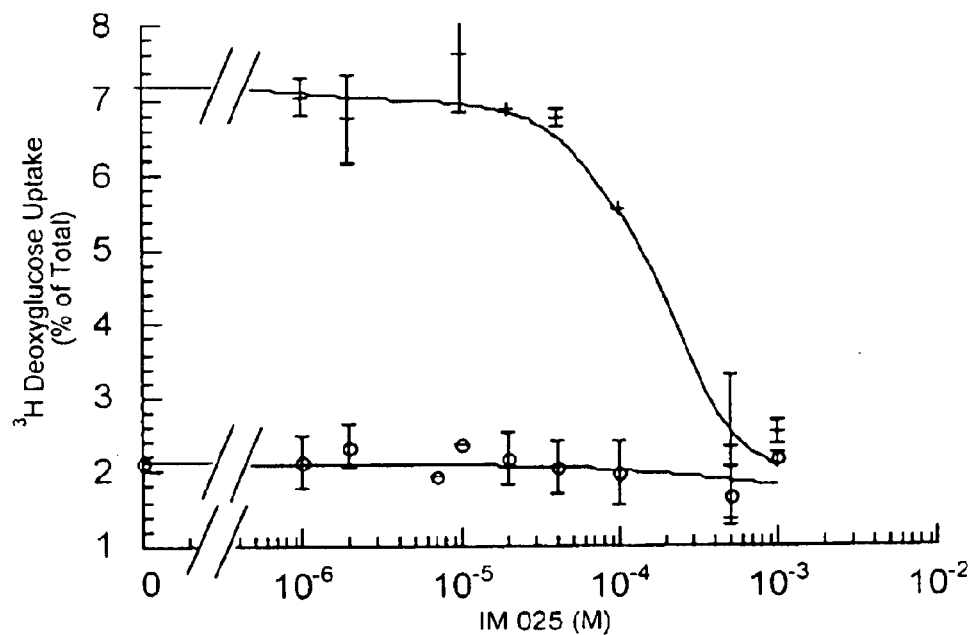
FIG. 16 represents the effect of IM 025 on total (presence of 2 nM insulin) (+) and basal (no insulin) (○) $^{3}$H-deoxyglucose uptake by 3T3L1 cells expressed as a percentage of total $^{3}$H-deoxyglucose added to cells, where each point is the mean of a triplicate determination±one standard deviation.
Figure 17:
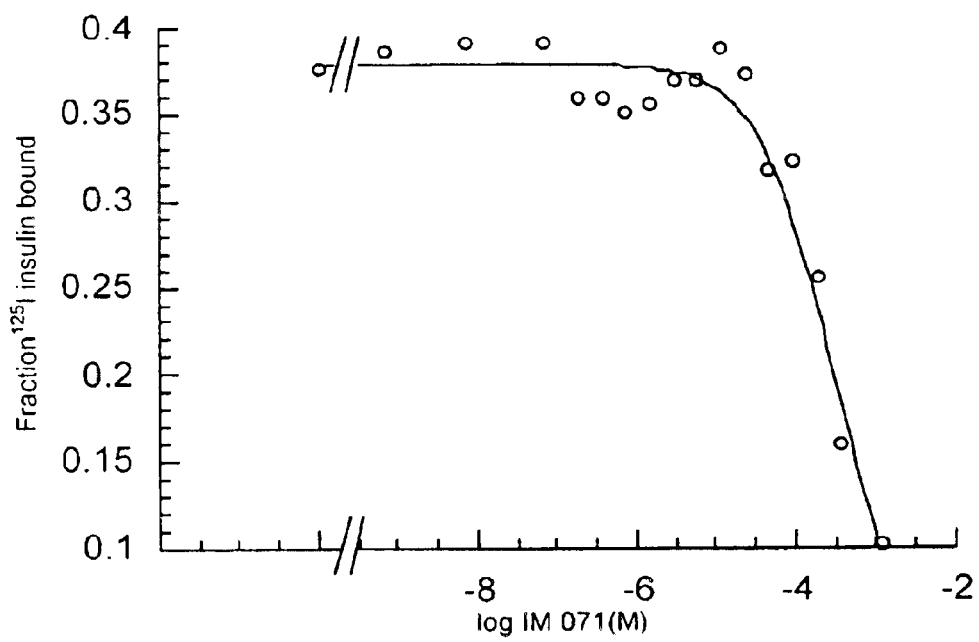
FIG. 17 shows the effect of IM 071 on $^{125}$I insulin bound to human placental plasma membranes (○) expressed as a fraction of total $^{125}$I insulin added where each data point is the mean of a triplicate determination.

As can be seen in FIGS. 16 and 17, IM 025 is an antagonist of insulin action. IM 025 causes a dose dependent decrease in the incorporation of $^{32}$P into FYF peptide in control (no insulin) and insulin stimulated tubes, as illustrated by FIG. 15. FIG. 16 shows that IM 025 also inhibits glucose transport in 3T3L1 cells. The estimated IC50 of IM 025 in these two assays is 150 µM and 170 µM respectively.

EXAMPLE 3

7-[3-(4-acetyl-2-ethyl-5-hydroxyphenoxy)propoxy]-3,4-dihydro-8-propyl-2H-1-benzopyran-2-carboxylic acid sodium salt (IM 071)

Effect on Insulin Binding

FIG. 17 shows that IM 071 competes for insulin binding to HPPM in a dose dependent manner, with an inhibition constant (calculated for two experiments) of 186 µM±33 µM. IM 071 is structurally related to IM 129 and is likely to have similar antagonistic effects of insulin in biological assays.

EXAMPLE 4

7-[(4-Acetyl-3-hydroxy-2-propylphenyl)methoxy]-4-oxo-8-propyl-4H-1-benzopyran-2-carboxylic acid (IM 127)

7-[(4-Acetyl-3-hydroxy-2-propylphenyl)methoxy]-4-oxo-8-propyl-4H-1-benzopyran-2-carboxylic acid can be obtained by the method described in European Patent Application EP 132, 366 incorporated herein by reference.

Effect on Insulin Binding

Figure 18:
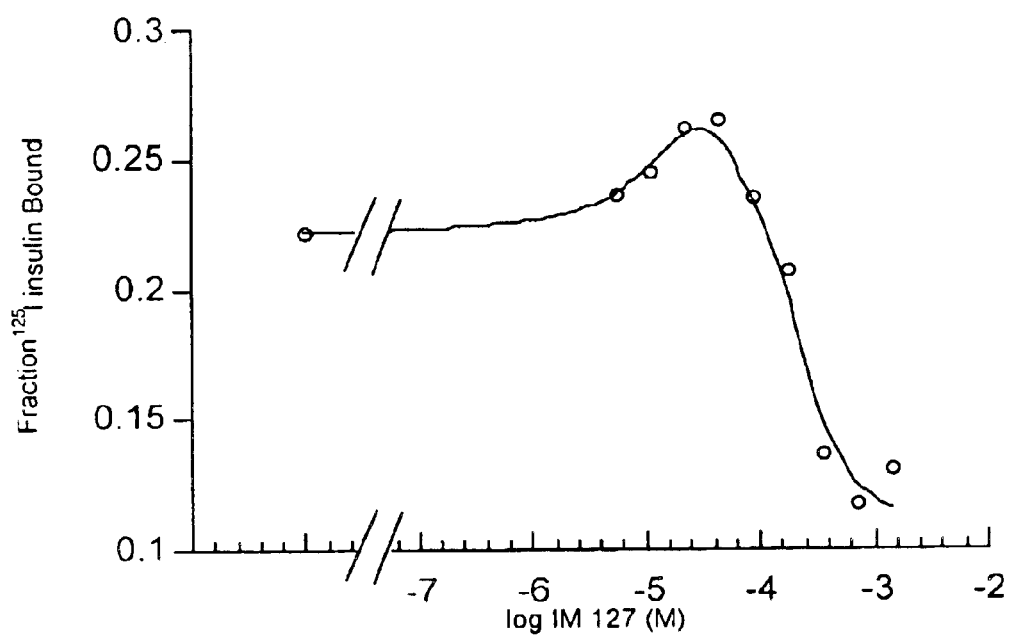
FIG. 18 summarises the effect of IM 127 on $^{125}$I insulin bound to human placental plasma membranes (+) expressed as a fraction of total $^{125}$I insulin added, where each data point is the mean of a triplicate determination.
Figure 19:
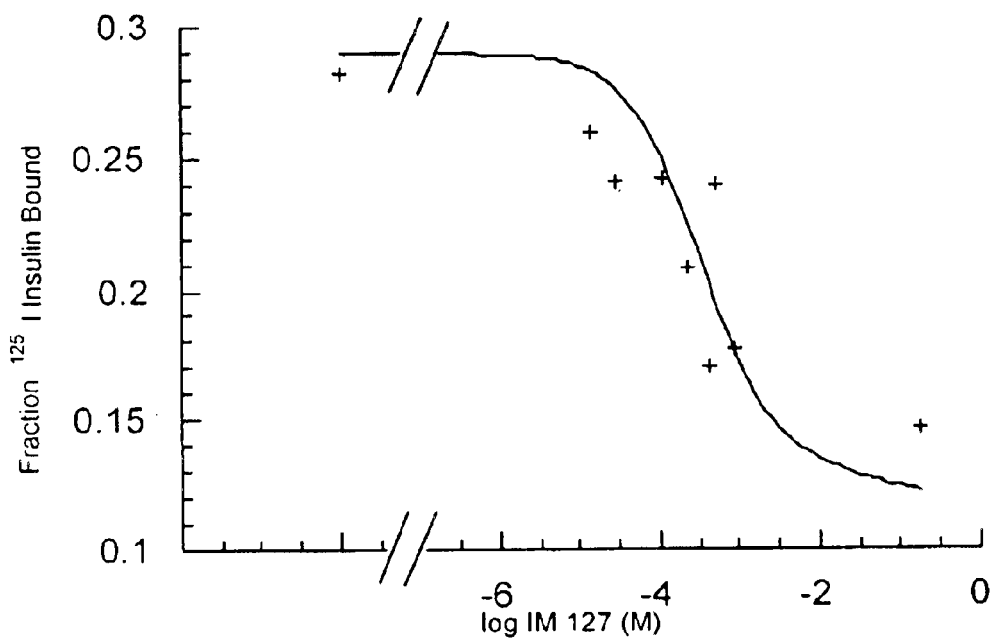
FIG. 19 shows the effect of IM 127 on $^{125}$I insulin bound to WGA.IR (+) expressed as a fraction of total $^{125}$I insulin added and overlayed with a 1-site fit to the data (solid line), where each data point is the mean of a triplicate determination.

IM 127 displays a skewed bell-shaped displacement plot of $^{125}$I insulin binding to HPPM with a peak in binding between 10 and 100 µM and competes for insulin binding with an apparent Ki of 140–320 µM, as can be seen in FIG. 18. FIG. 19 shows that IM 127 competes for $^{125}$I insulin binding to WGA.IR in a less complex manner with an apparent Ki of 295 µM (LIGAND, 1-site fit).

Effect on Biological Activity

Figure 20:
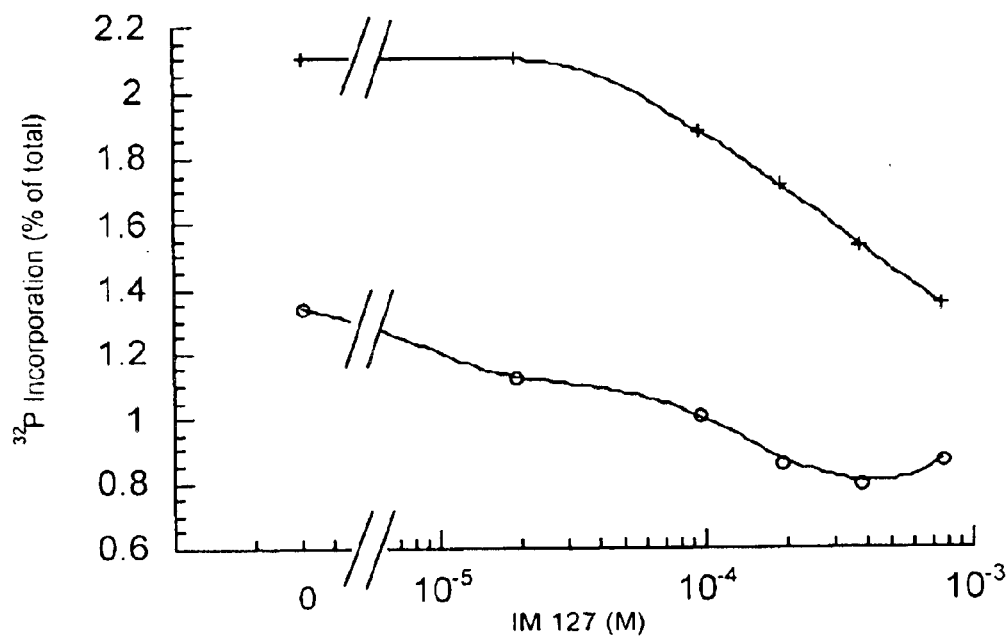
FIG. 20 illustrates $^{32}$P incorporation into FYF peptide in the presence of IM 127, where the effect of IM 127 on total (in the presence of 50 nM insulin) (+) and basal (absence of insulin) (○) $^{32}$P incorporation into FYF peptide is expressed as a percentage of total $^{32}$P-γ-ATP added to reactions, and where each data point is the mean of a duplicate determination.
Figure 21:
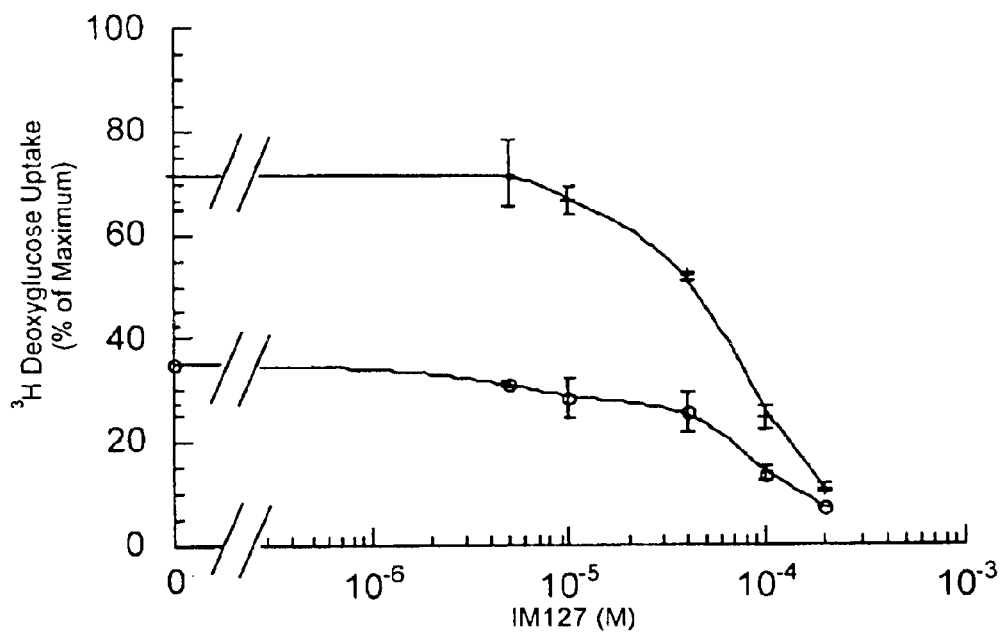
FIG. 21 demonstrates the effect of IM 127 on total (presence of 2 nM insulin) (+) and basal (no insulin) (○) $^{3}$H-deoxyglucose uptake by 3T3L1 cells, where glucose transport in is expressed as a percentage of a maximal 100 nM dose of insulin and where each point is the mean of a triplicate determination±one standard deviation.

IM 127 displays insulin antagonistic activity in a number of assays, summarised in FIGS. 20 and 21. FIG. 21 specifically shows that the estimated Ki is 60 µM in the glucose transport assay.

EXAMPLE 5

3,4-Dihydro-8-propyl-7-[[3-[2-ethyl-5-hydroxy-4-(1H-pyrazol-3-yl)phenoxy]propyl]oxy]-2H-1-benzopyran-2-carboxylic acid (IM 132)

3,4-Dihydro-8-propyl-7-[[3-[2-ethyl-5-hydroxy-4-(1 H-pyrazol-3-yl)phenoxy]propyl]oxy]-2H-1-benzopyran-2-carboxylic acid can be synthesised by the method described by R. W. Harper et al. (28), incorporated herein by reference.

Effect on Insulin Binding

Figure 22:
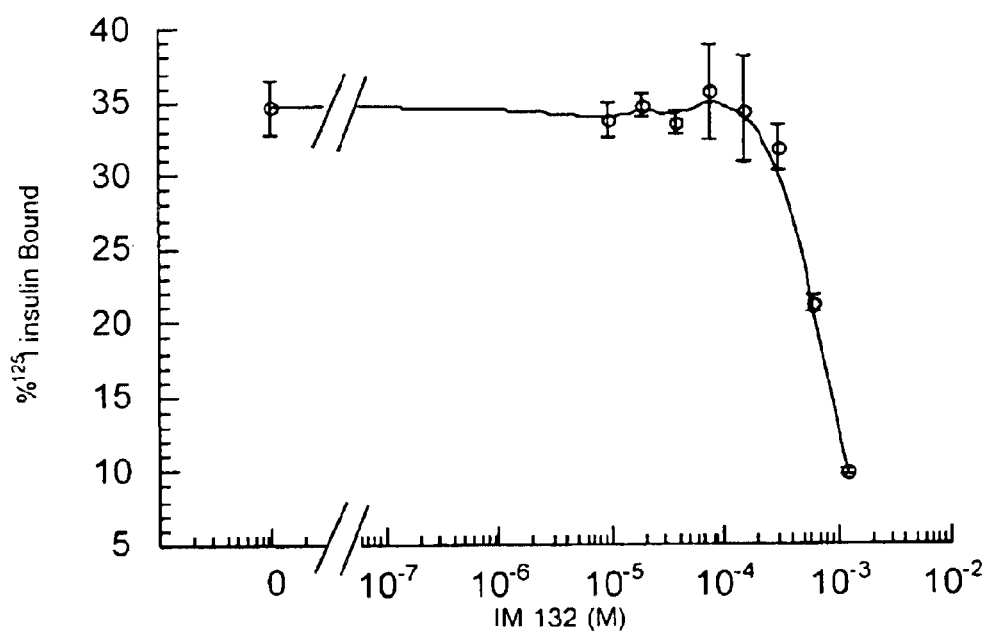
FIG. 22 represents the effect of IM 132 on $^{125}$I insulin bound to human placental plasma membranes (○), expressed as a percentage of total $^{125}$I insulin added, where each data point is the mean of a triplicate determination±one standard deviation.
Figure 23:
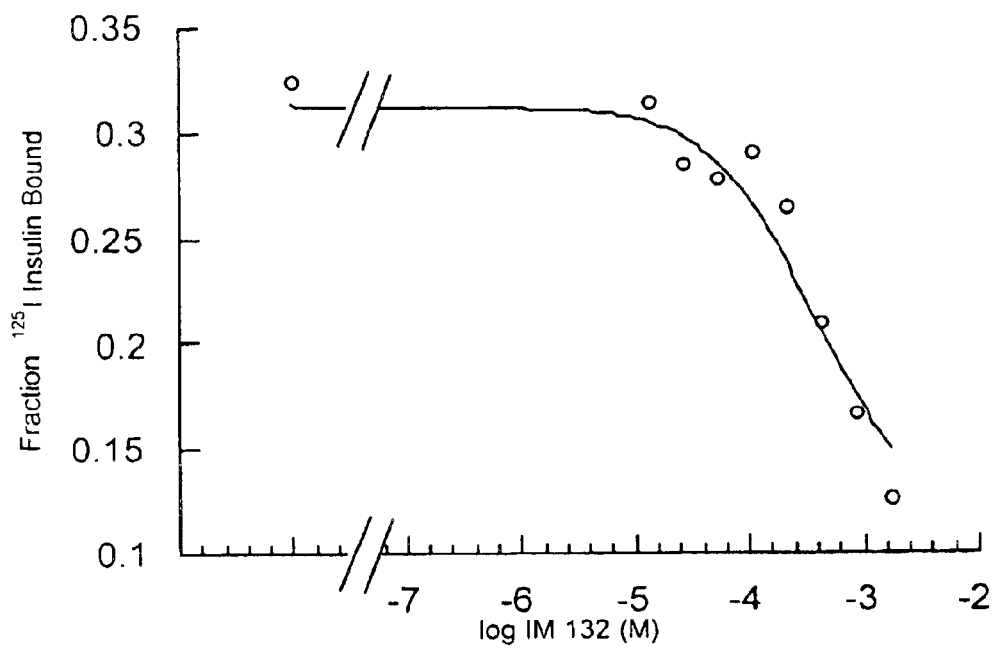
FIG. 23 shows the effect of IM 132 on $^{125}$I insulin bound to WGA.IR (○), expressed as a fraction of total $^{125}$I insulin added and overlayed with a 1-site fit to the data (solid line), where each data point is the mean of a triplicate determination.

FIGS. 22 and 23 illustrate that IM 132 effects insulin binding with an apparent inhibition constant of 200 to 450 µM, which is dependent upon receptor source.

Effect on Bioloqical Activity

Figure 24:
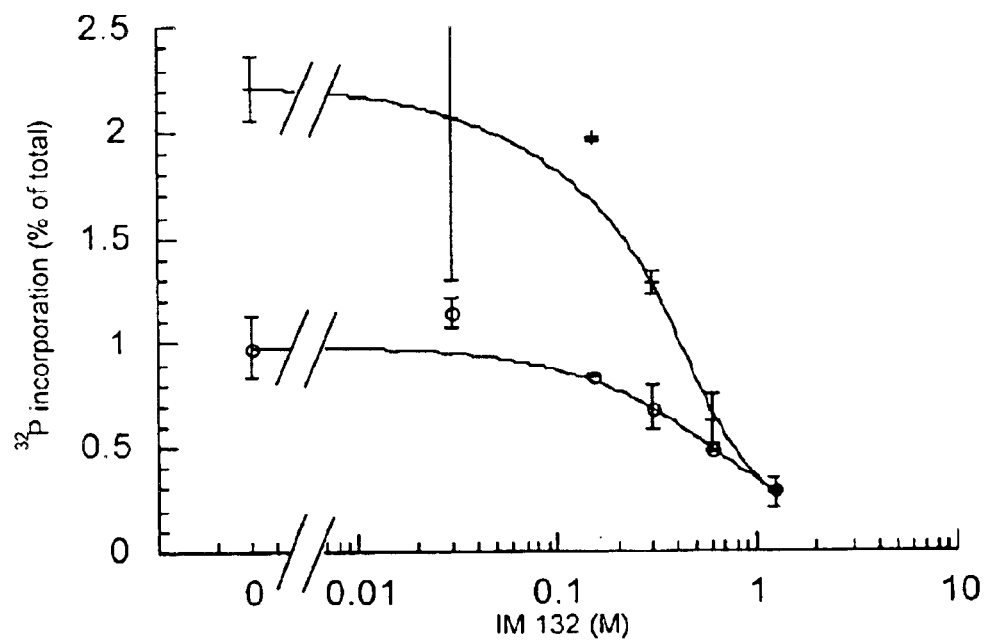
FIG. 24 represents the effect of IM 132 on total (in the presence of 50 nM insulin) (+) and basal (absence of insulin) (○) $^{32}$P incorporation into FYF peptide, expressed as a percentage of total $^{32}$P-γ-ATP added to reactions, where each data point is the mean of a duplicate determination±one standard deviation.
Figure 25:
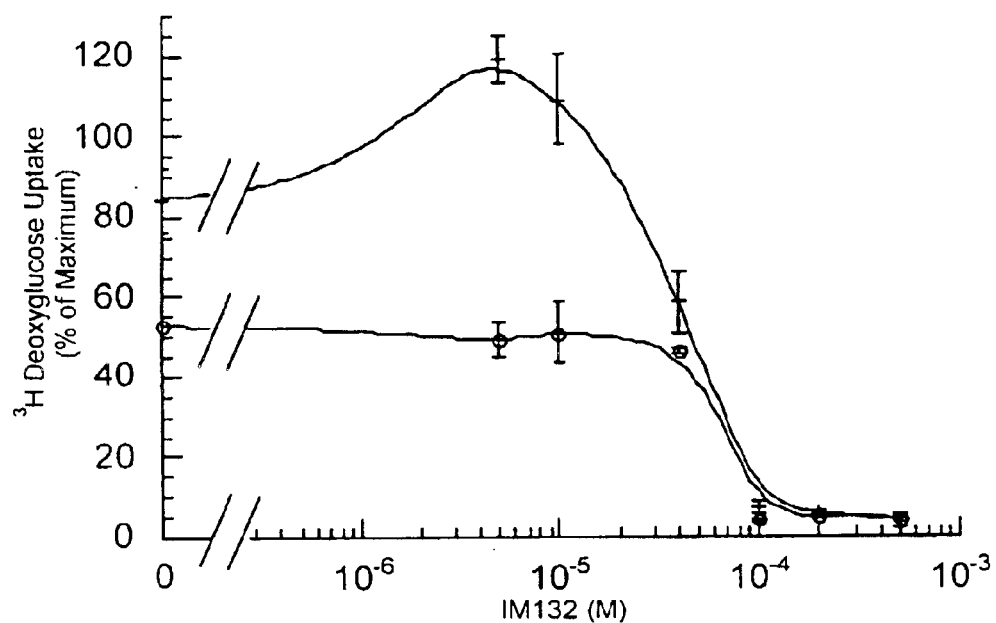
FIG. 25 shows the effect of IM 132 on total (presence of 2 nM insulin) (+) and basal (no insulin) (○) $^{3}$H-deoxyglucose uptake by 3T3L1 cells, where glucose transport in is expressed as a percentage of a maximal 100 nM dose of insulin, and where each point is the mean of a triplicate determination±one standard deviation.

IM 132 is an antagonist of insulin action because it does not increase $^{32}$P incorporation into FYF peptide or activate glucose transport. FIGS. 24 and 25 illustrate that it also inhibits the insulin stimulation of these assays. The estimated inhibition constant of the compound in the PTK and glucose transport assays is 360 µM and 64 µM respectively. However, in the presence of insulin, IM 132 shows significant synergism with insulin in the glucose transport assay, increasing the effect of a submaximal dose of insulin (2 nM) to levels above those attained by 100 nM insulin. This indicates that IM 132 may be interacting with the insulin receptor at the insulin binding site in a more complex manner than IM 129.

EXAMPLE 6

3,4-di hydro-8-propyl-7-[[3-[2-ethyl-5-hyd roxy-4-ethoxyphenoxy]propyl]oxy]-2H-1-benzopyran-2-carboxylic acid (IM 134)

3,4-dihydro-8-propyl-7-[[3-[2-ethyl-5-hydroxy-4-ethoxyphenoxy]propyl]oxy]-2H-1-benzopyran-2-carboxylic acid can be obtained by the method described in International Application WO 95 17, 183, incorporated herein by reference.

Effect on Insulin Binding

Figure 26:
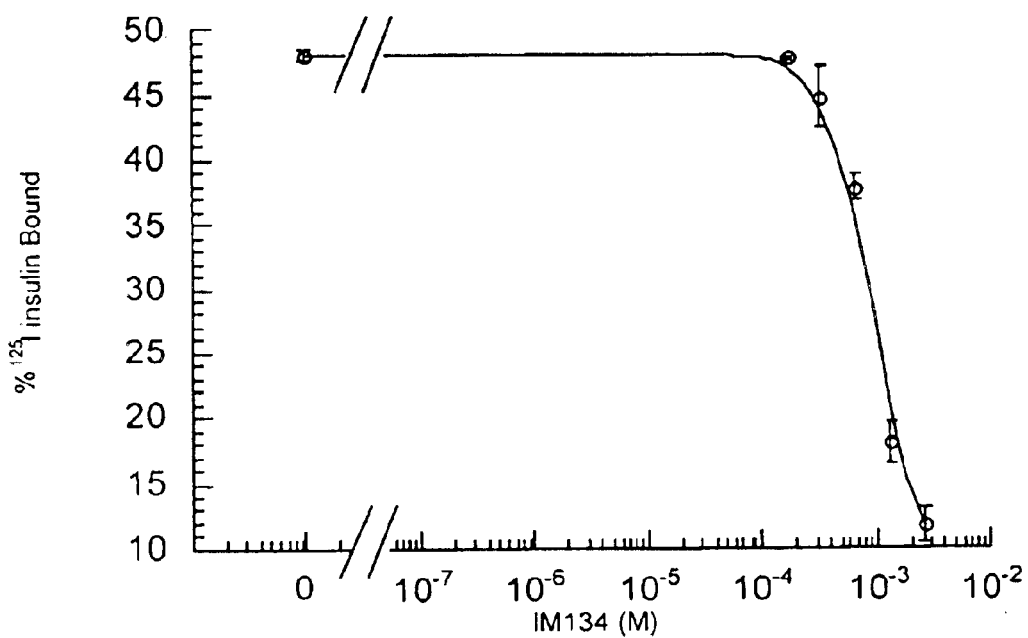
FIG. 26 shows the effect of IM 134 on $^{125}$I insulin bound to human placental plasma membranes (○), expressed as a percentage of total $^{125}$I insulin added and where each point is the mean of a triplicate determination±one standard deviation.

FIG. 26 shows that IM 134 competes with $^{125}$I insulin binding to HPPM with an apparent Ki of 900 µM.

Effect on Biological Activity

Figure 27:
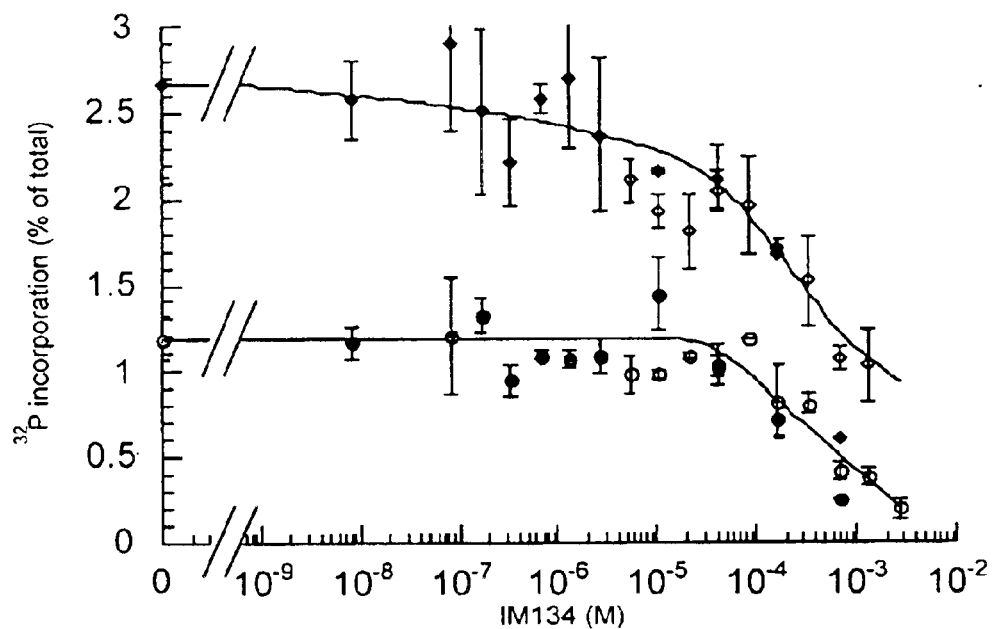
FIG. 27 demonstrates the effect of IM 134 on total (in the presence of 400 nM insulin) (◇) and basal (absence of insulin) (○) $^{32}$P incorporation into FYF peptide, expressed as a percentage of total $^{32}$P-γ-ATP added to reactions, where two separate experiments are shown by open and solid symbols, and where each data point is the mean of a duplicate determination±one standard deviation.
Figure 28:
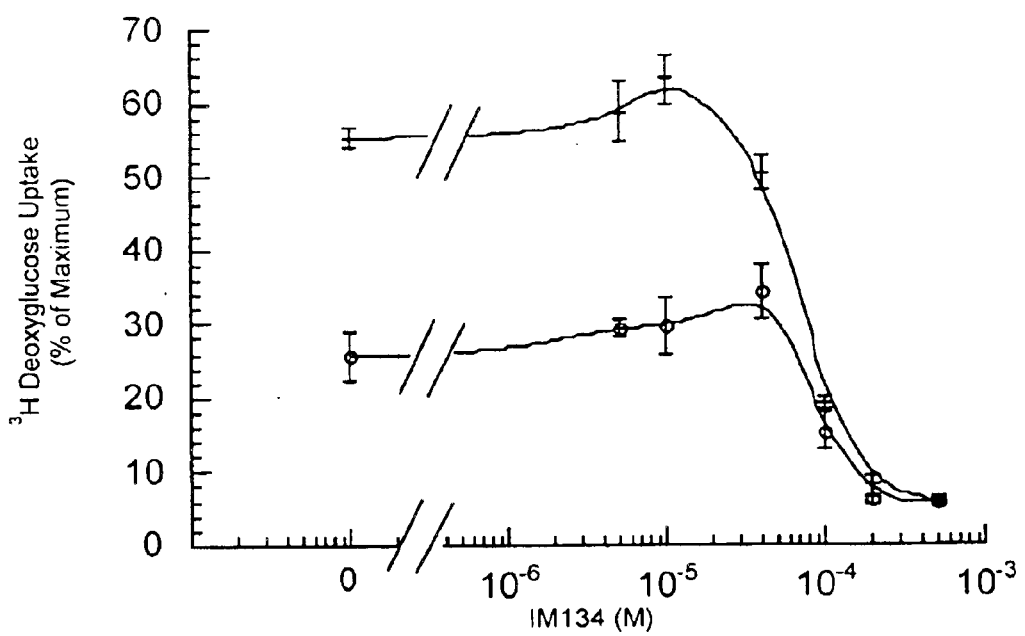
FIG. 28 shows the effect of IM 134 on $^{3}$H-deoxyglucose uptake in the presence (+) and absence (○) of 2 nM insulin by 3T3L1 adipocyte cells, where glucose transport in is expressed as a percentage of a maximal 100 nM dose of insulin, and each point is the mean of a triplicate determination±one standard deviation.

IM 134 is an antagonist of insulin action because it does not increase $^{32}$P incorporation into FYF peptide or glucose transport and inhibits the insulin stimulation of these assays, as can be seen in FIGS. 27 and 28. The estimated inhibition constants of the compound in these assays are 300–400 µM and 60–110 µM respectively.

EXAMPLE 7

8-propyl-7-(quinol-2'-ylmethoxy)-3,4-dihydro-2H-1-benzopyran-2-carboxylic acid (IM 143)

Effect on Insulin Binding

Figure 29:
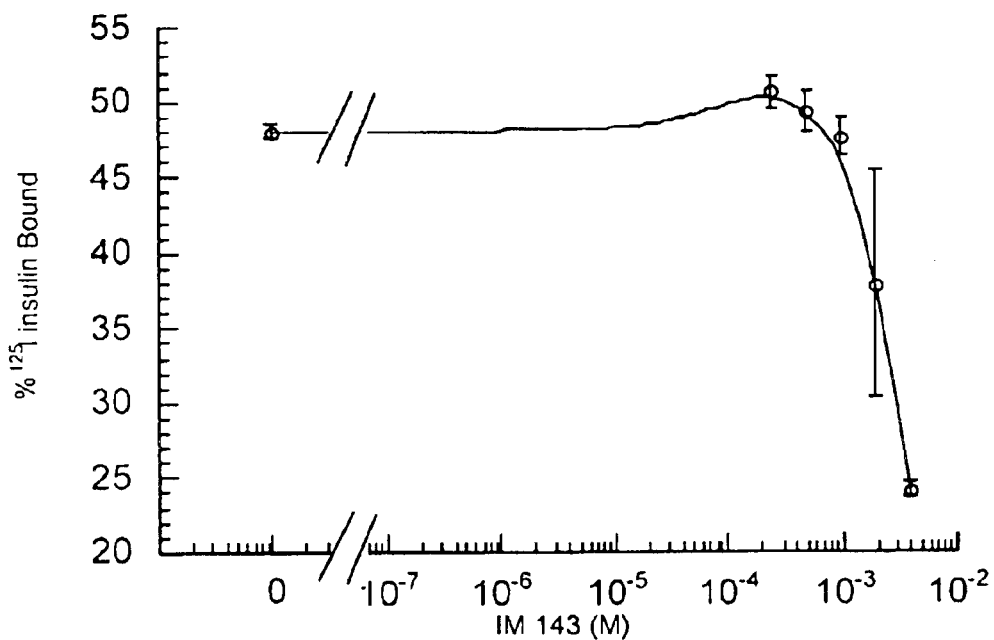
FIG. 29 illustrates the effect of IM 143 on $^{125}$I insulin bound to human placental plasma membranes (○), expressed as a percentage of total $^{125}$I insulin added and where each point is the mean of a triplicate determination±one standard deviation.

As FIG. 29 shows, IM 143 competes with $^{125}$I insulin binding to HPPM with an apparent Ki of about 2 mM.

Effect on Biological Activity

Figure 30:
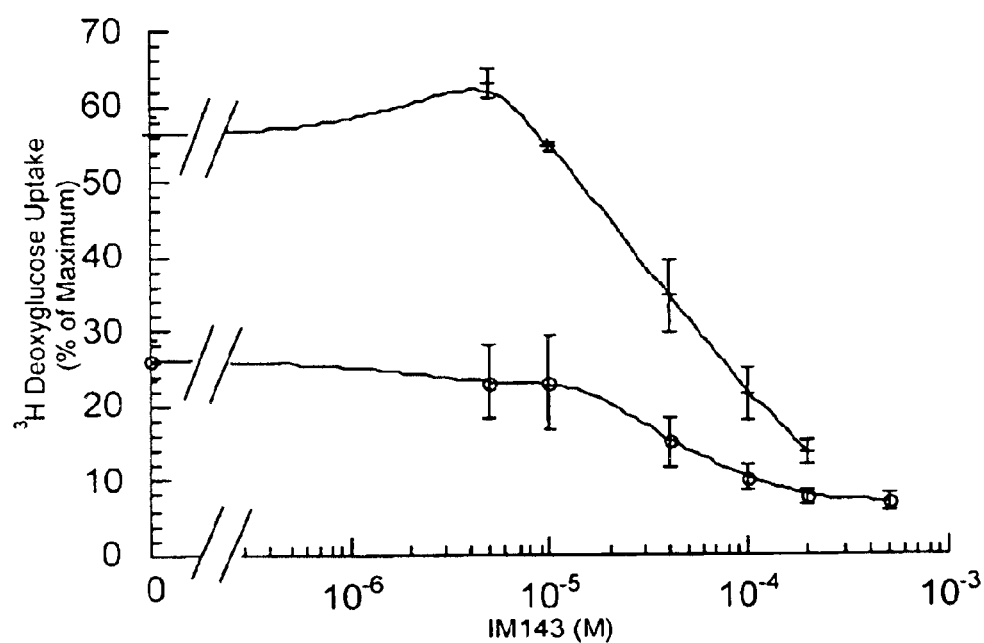
FIG. 30 represents the effect of IM 143 on total (presence of 2 nM insulin) (+) and basal (no insulin) (○) $^{3}$H-deoxyglucose uptake by 3T3L1 cells, where glucose transport is expressed as a percentage of a maximal 100 nM dose of insulin, and where each point is the mean of a triplicate determination±one standard deviation.

IM 143 is an antagonist of insulin action because it does not stimulate glucose transport activity and inhibits a stimulating (2 nM) dose of insulin with an estimated inhibition constant of 40 µM as illustrated in FIG. 30.

EXAMPLE 8

7-(naphth-2'-ylmethoxy)-8-propyl-3,4-dihydro-2H-1-benzopyran-2-carboxylic acid (IM 144)

Effect on Insulin Binding

Figure 31:
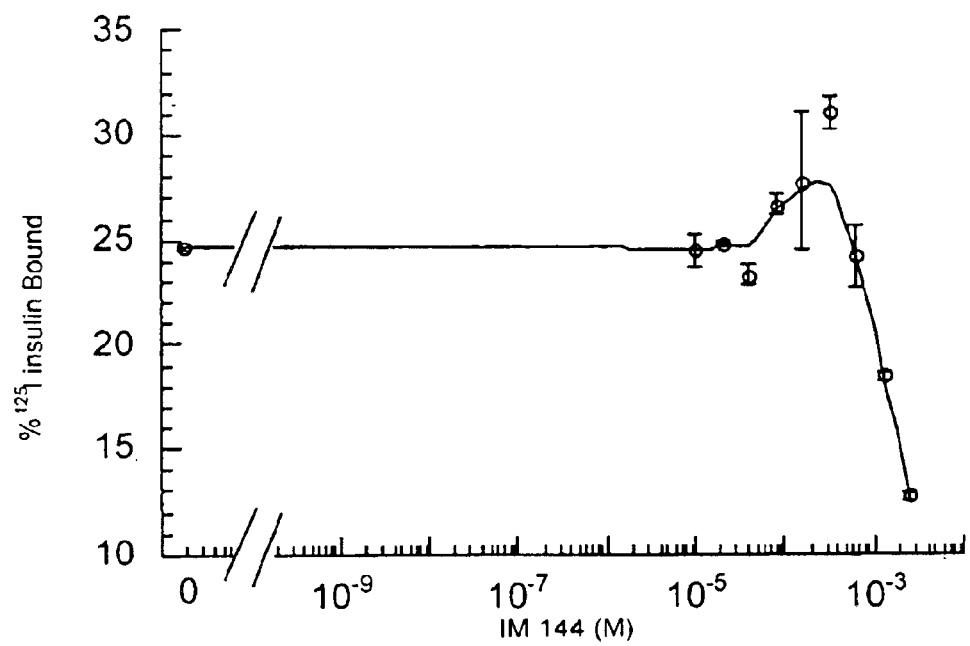
FIG. 31 shows the effect of IM 144 on $^{125}$I insulin bound to human placental plasma membranes (○), expressed as a percentage of total $^{125}$I insulin added and where each point is the mean of a triplicate determination±one standard deviation.
Figure 32:
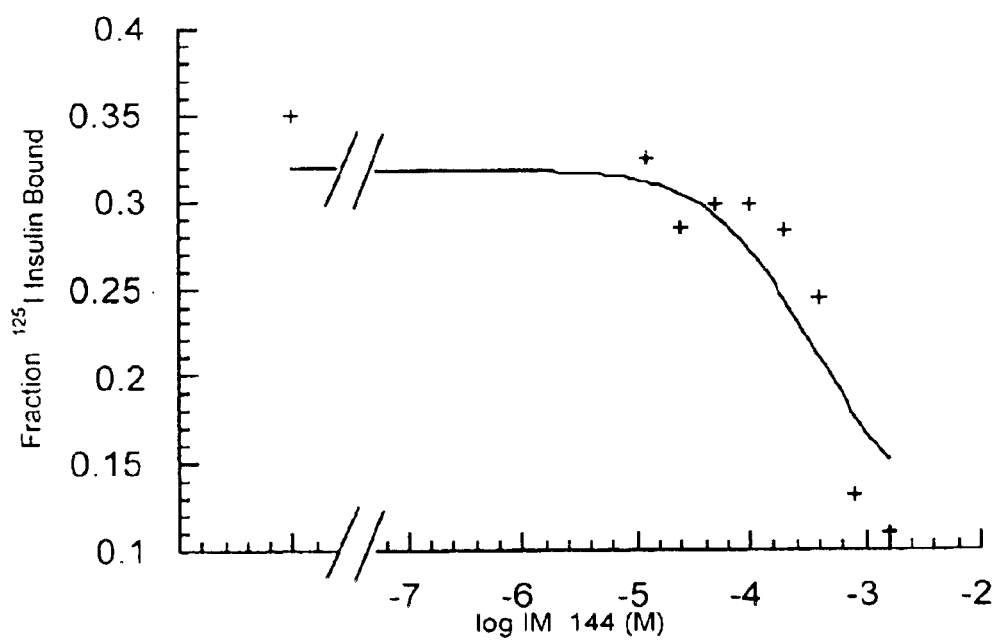
FIG. 32 illustrates the effect of IM 144 on 125$^{125}$I insulin bound to WGA.IR (○), expressed as a fraction of total $^{125}$I insulin added and overlayed with a 1-site fit to the data (solid line), in which each data point is the mean of a triplicate determination.

IM 144 effects insulin binding in a range of receptor sources, evident from FIGS. 31 and 32. IM 144 causes a skewed bell-shaped displacement plot of $^{125}$I insulin binding to HPPM with an apparent Ki of 900 µM.

Effect on Bioloqical Activity

Figure 33:
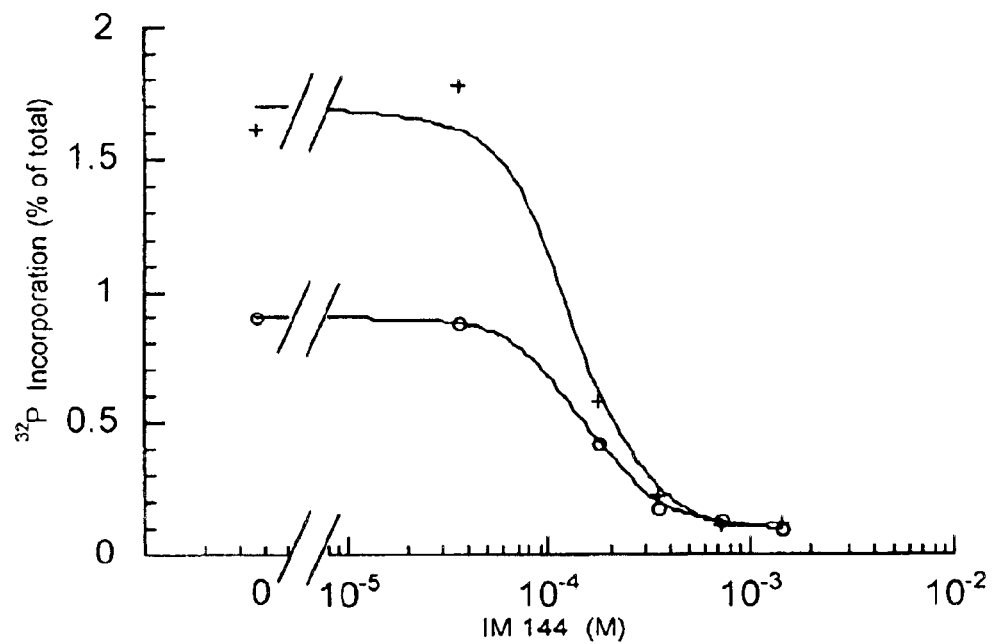
FIG. 33 represents the effect of IM 144 on total (in the presence of 50 nM insulin) (+) and basal (absence of insulin) (○) $^{32}$P incorporation into FYF peptide, expressed as a percentage of total $^{32}$P-γ-ATP added to reactions, where each data point is the mean of a duplicate determination.
Figure 34:
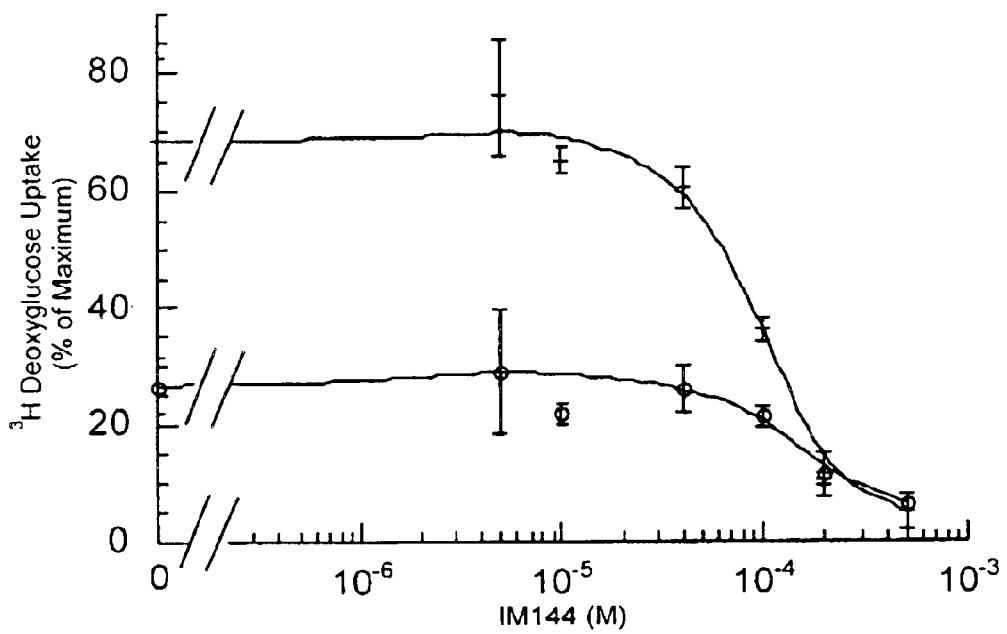
FIG. 34 shows the effect of IM 144 on total (presence of 2 nM insulin) (+) and basal (no insulin) (○) $^{3}$H-deoxyglucose uptake by 3T3L1 cells, in which glucose transport in is expressed as a percentage of a maximal 100 nM dose of insulin, and where each point is the mean of a triplicate determination±one standard deviation.

IM 144 is an antagonist of insulin action because it does not increase $^{32}$P incorporation into FYF peptide or activate glucose transport and inhibits the insulin stimulation of these assays, as shown in FIGS. 33 and 34. The estimated inhibition constant of the compound in the PTK and glucose transport assays is 130 μM and 125 μM respectively.

EXAMPLE 9

N-(trifluoromethanesulfonyl)-3,5-dinitro-4-(N',N'-dipropylamino)benzenesulfonamide (IM 145)

Effect on Insulin Binding

Figure 35:
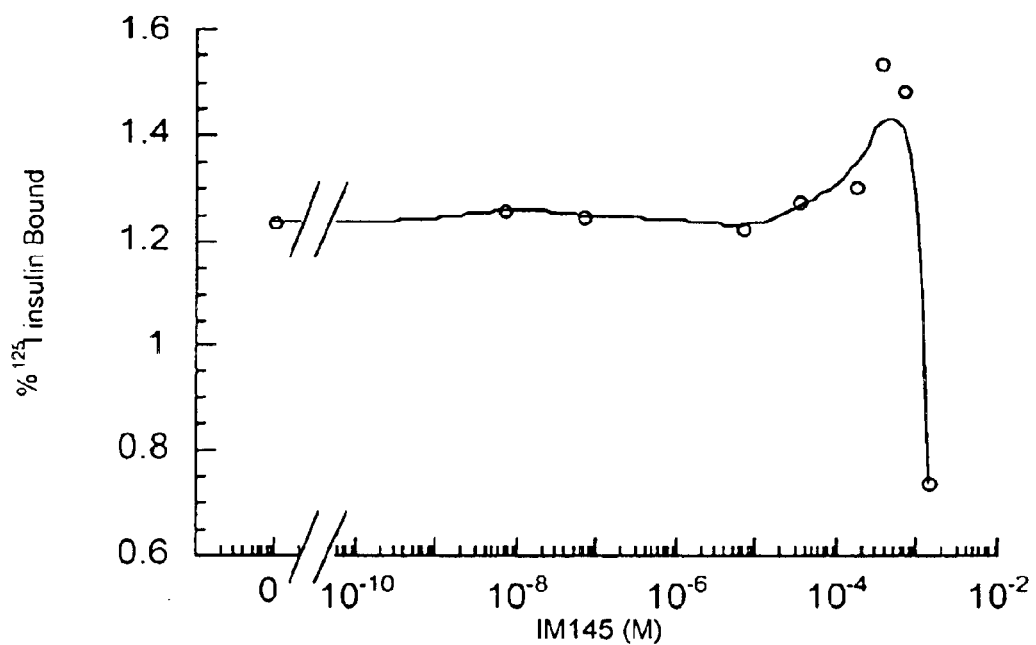
FIG. 35 illustrates the effect of IM 145 on $^{125}$I insulin bound to human placental plasma membranes (○), expressed as a percentage of total $^{125}$I insulin added and where each point is the mean of a triplicate determination.

IM 145 competes for $^{125}$I insulin binding to HPPM with an apparent Ki of about 1000 μM as shown in FIG. 35.

Effect on Biological Activity

Figure 36:
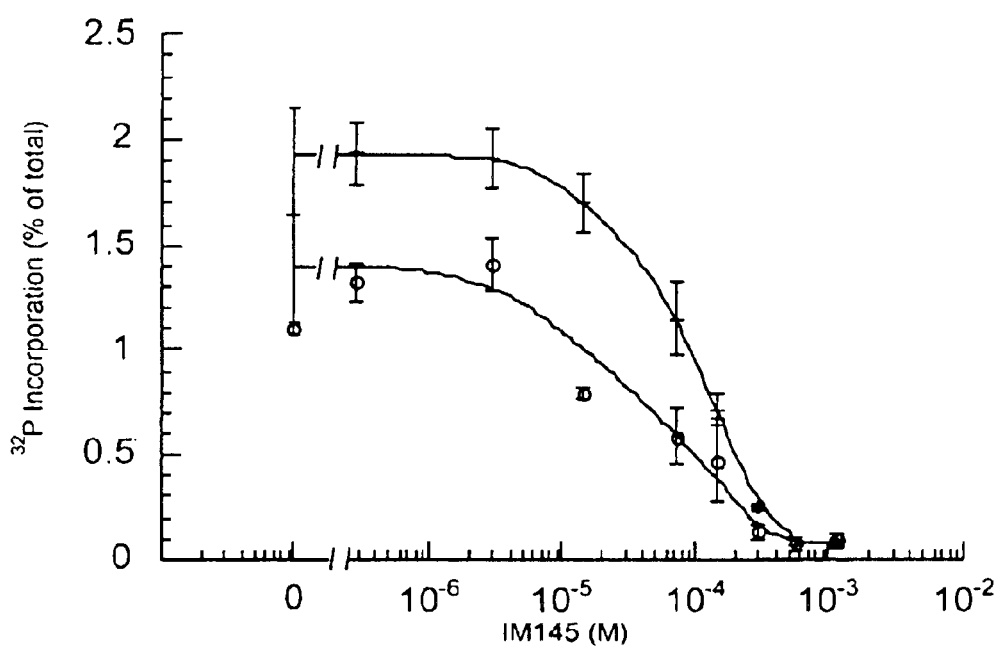
FIG. 36 shows the effect of IM 145 on total (in the presence of 50 nM insulin) (+) and basal (absence of insulin) (○) $^{32}$P incorporation into FYF peptide, expressed as a percentage of total $^{32}$P-γ-ATP added to reactions, in which each data point is the mean of a duplicate determination±one standard deviation.
Figure 37:
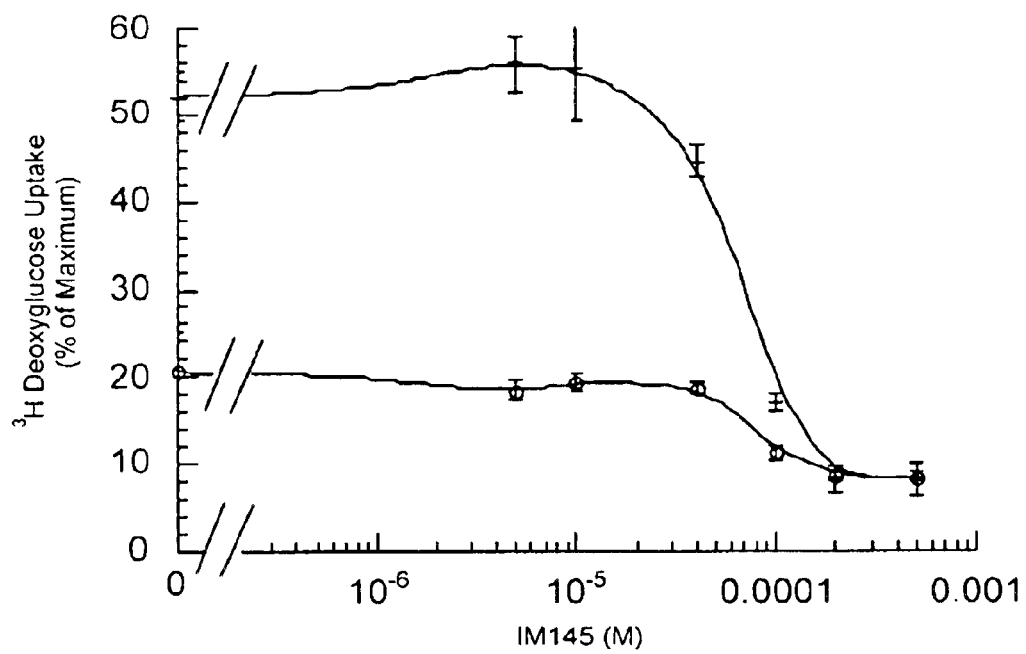
FIG. 37 demonstrates the effect of IM 145 on total (presence of 2 nM insulin) (+) and basal (no insulin) (○) $^{3}$H-deoxyglucose uptake by 3T3L1 cells, where glucose transport is expressed as a percentage of a maximal 100 nM dose of insulin, and each point is the mean of a triplicate determination±one standard deviation.

FIGS. 36 and 37 show that IM 145 is an antagonist of insulin action because it does not stimulate PTK or glucose transport activity and inhibits a stimulating dose of insulin (400 nM and 2 nM respectively) in each assay with an estimated IC50 of 90 and 60 μM respectively.

EXAMPLE 10

8-Propyl-7-[3-[4-(4-fluorophenyl)-2-ethyl-5-hydroxyphenoxy]propoxy]-3,4-dihydro-2H-1-benzopyran-2-carboxylic acid (IM 171)

8-Propyl-7-[3-[4-(4-fl uorophenyl)-2-ethyl-5-hydroxyphenoxy]propoxy]-3,4-dihydro-2H-1-benzopyran-2-carboxylic acid can be obtained by the method described in International Application WO 95/17183 (Eli Lilly and Co) incorporated herein by reference.

Effect on Insulin Binding

Figure 38:
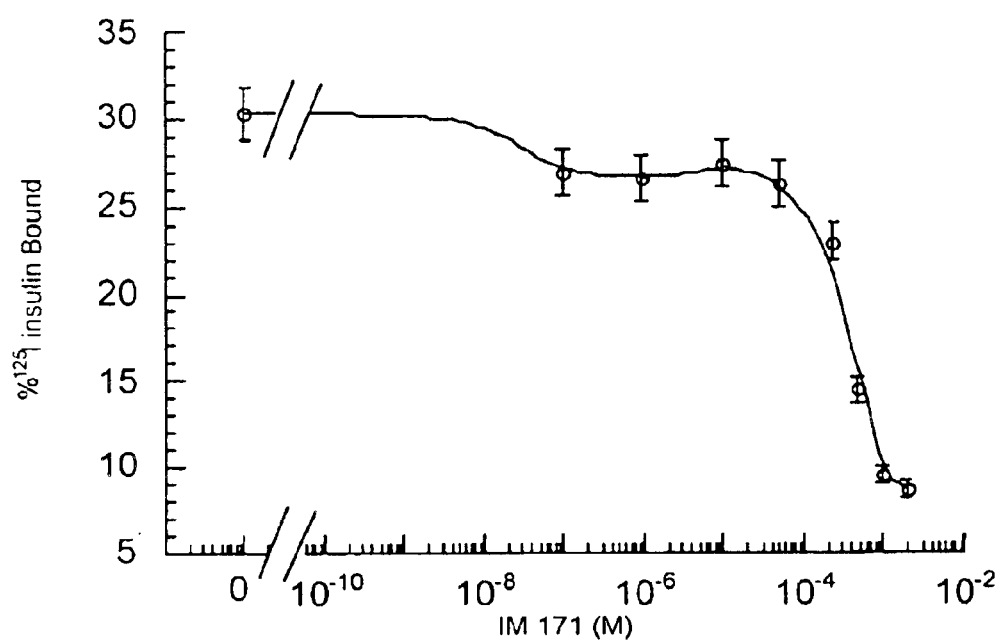
FIG. 38 represents the effect of IM 171 on $^{125}$I insulin bound to human placental plasma membranes (○), expressed as a percentage of total $^{125}$I insulin added and where each point is the mean of a triplicate determination±one standard deviation.

FIG. 38 shows that IM 171 competes for $^{125}$I insulin binding to HPPM with an apparent Ki of 370 μM.

Effect on Biological Activity

Figure 39:
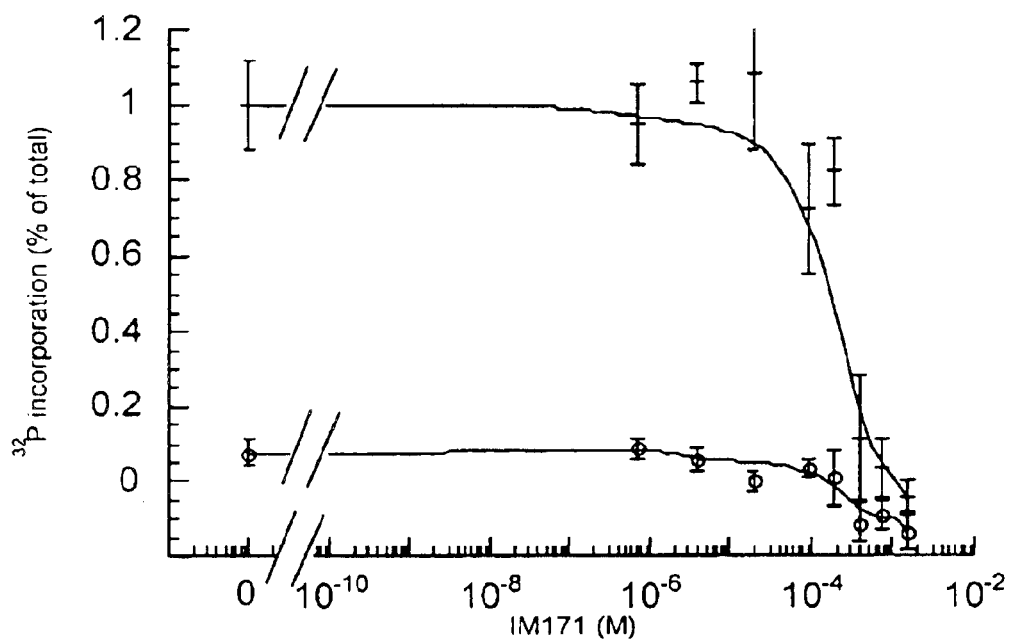
FIG. 39 shows the effect of IM 171 on total (in the presence of 400 nM insulin) (+) and basal (absence of insulin) (○) $^{32}$P incorporation into FYF peptide, expressed as a percentage of total $^{32}$P-γ-ATP added to reactions, where each data point is the mean of a duplicate determination±one standard deviation.
Figure 40:
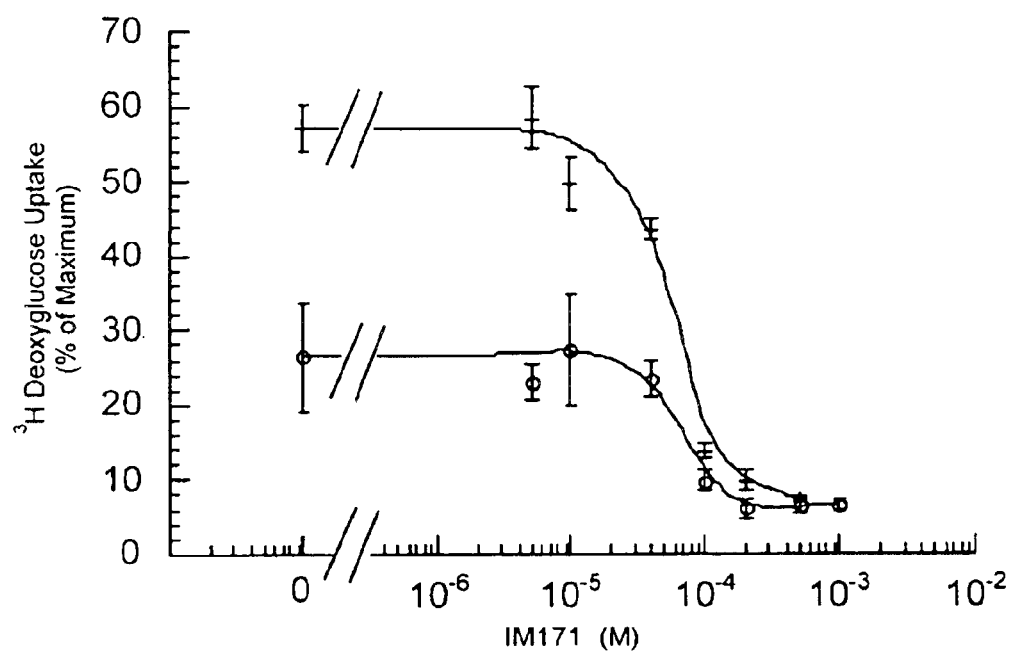
FIG. 40 illustrates the effect of IM 171 on total (presence of 2 nM insulin) (+) and basal (no insulin) (○) $^3$H-deoxyglucose uptake by 3T3L1 cells, where glucose transport is expressed as a percentage of a maximal 100 nM dose of insulin, and where each point is the mean of a triplicate determination±one standard deviation.

IM 171 is an antagonist of insulin action. It does not increase $^{32}$P incorporation into FYF peptide or activate glucose transport and inhibits insulin stimulation of each of these assays, as is evident from FIGS. 39 and 40. The estimated IC50 in the PTK and glucose transport assays are 250 μM and 80 μM respectively.

EXAMPLE 11

3,4-dihydro-7-[[6-(4-methoxyphenyl)hexenyl]oxy]-8-propyl-2H-1-benzopyran-2-carboxylic acid
(IM 172)

Effect on Insulin Binding

Figure 41:
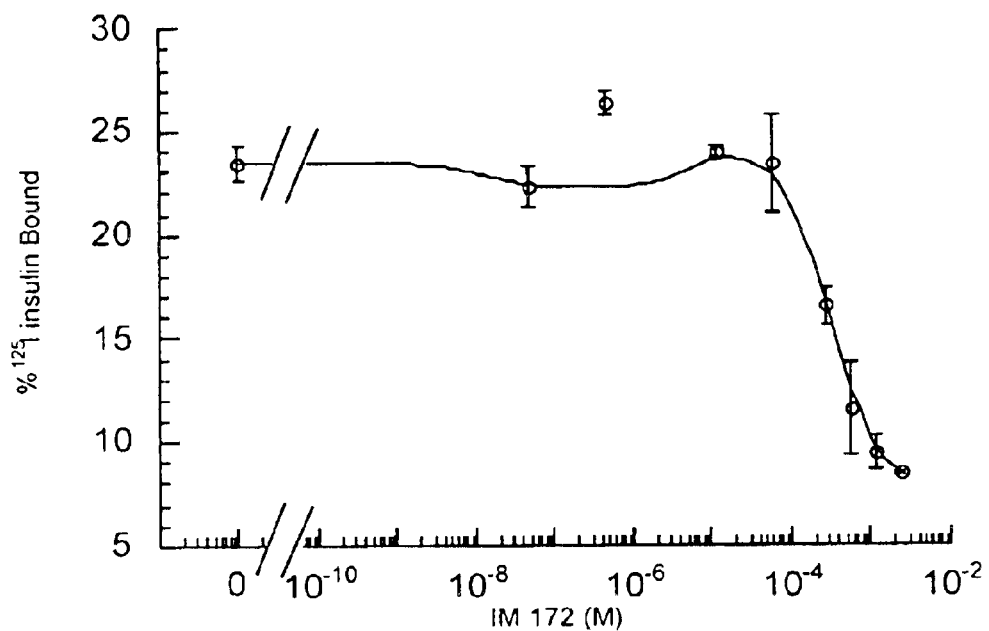
FIG. 41 shows the effect of IM 172 on $^{125}$I insulin bound to human placental plasma membranes (○), expressed as a percentage of total $^{125}$I insulin added and where each point is the mean of a triplicate determination±one standard deviation.

IM 172 competes for $^{125}$I insulin binding to HPPM with an apparent Ki of 218 μM, as FIG. 41 illustrates.

Effect on Biological Activity

Figure 42:
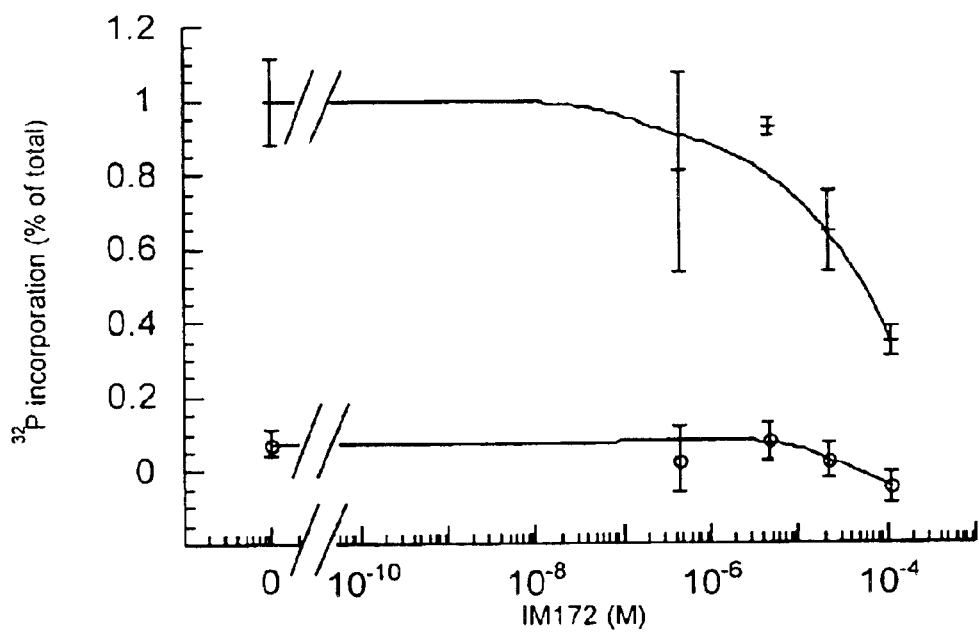
FIG. 42 shows the effect of IM 172 on total (in the presence of 400 nM insulin) (+) and basal (absence of insulin) (○) $^{32}$P incorporation into FYF peptide, expressed as a percentage of total $^{32}$P-γ-ATP added to reactions, where each data point is the mean of a duplicate determination±one standard deviation.
Figure 43:
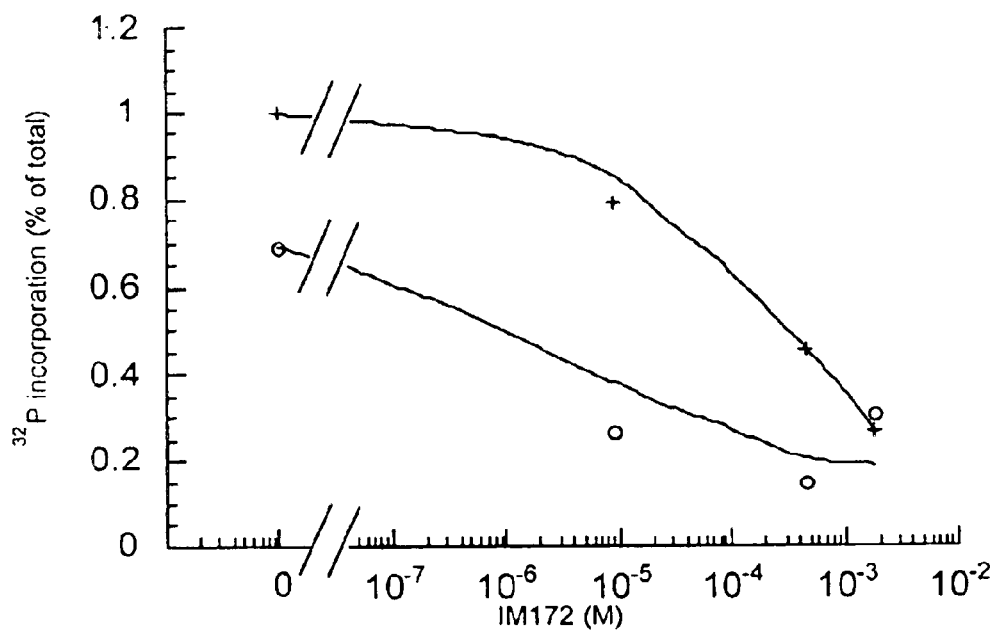
FIG. 43 illustrates the effect of IM 172 on total (in the presence of 400 nM insulin) (+) and basal (absence of insulin) (○) $^{32}$P incorporation into WGA.IR 90 kDa protein band, expressed as a percentage of total $^{32}$P-γ-ATP added to reactions.
Figure 44:
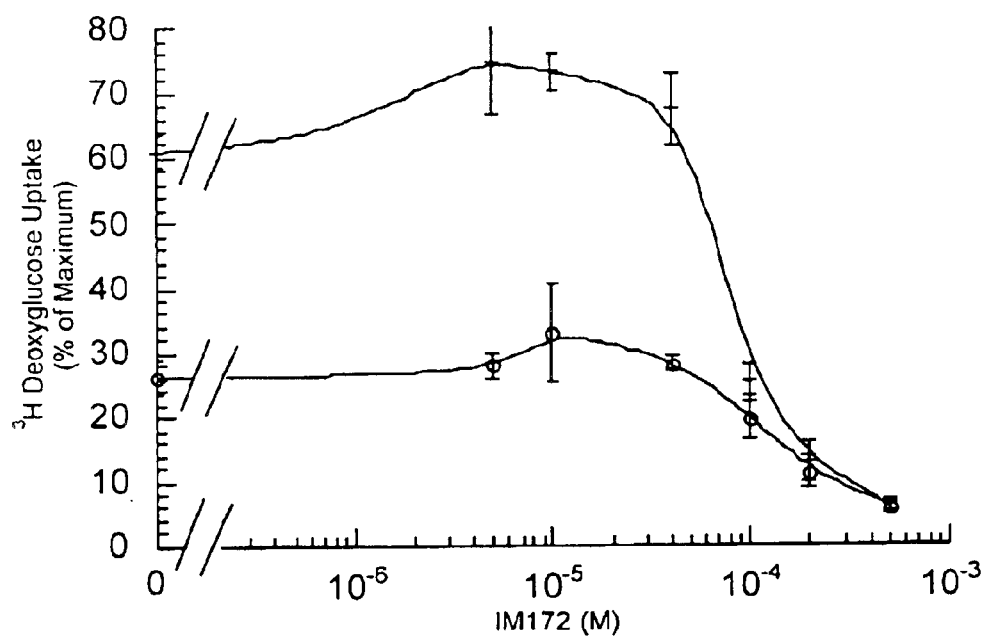
FIG. 44 shows the effect of IM 172 on total (presence of 2 nM insulin) (+) and basal (no insulin) (○) $^3$H-deoxyglucose uptake by 3T3L1 cells, in which glucose transport in is expressed as a percentage of a maximal 100 nM dose of insulin, and where each point is the mean of a triplicate determination±one standard deviation.

IM 172 is an antagonist of insulin action. It does not increase $^{32}$P incorporation into FYF peptide or the insulin receptor β-subunit and does not activate glucose transport in 3T3L1 cells. As FIGS. 42 to 44 demonstrate, it also inhibits the insulin stimulation of each of these assays. The estimated inhibition constant of the compound is 80 μM in the both the PTK and glucose transport assays.

Agonist Compounds

IM 140, IM 175, IM 103 have been classified as agonists of insulin action.

EXAMPLE 12

3-[4-[7-carboxy-9-oxo-3-[3-[2-ethyl-4-(4-fluorophenyl)-5-hydroxyphenoxy]propoxy]-9H-xanthene]]propanoic acid disodium trihydrate
(IM 140)

3-[4-[7-Carboxy-9-oxo-3-[3-[2-ethyl-4-(4-fluorophenyl)-5-hydroxyphenoxy]propoxy]-9H-xanthene]]propanoic acid disodium trihydrate can be synthesised by the method described by J. S. Sawyer et al. (29), incorporated herein by reference.

Effect on Insulin Binding

Figure 45:
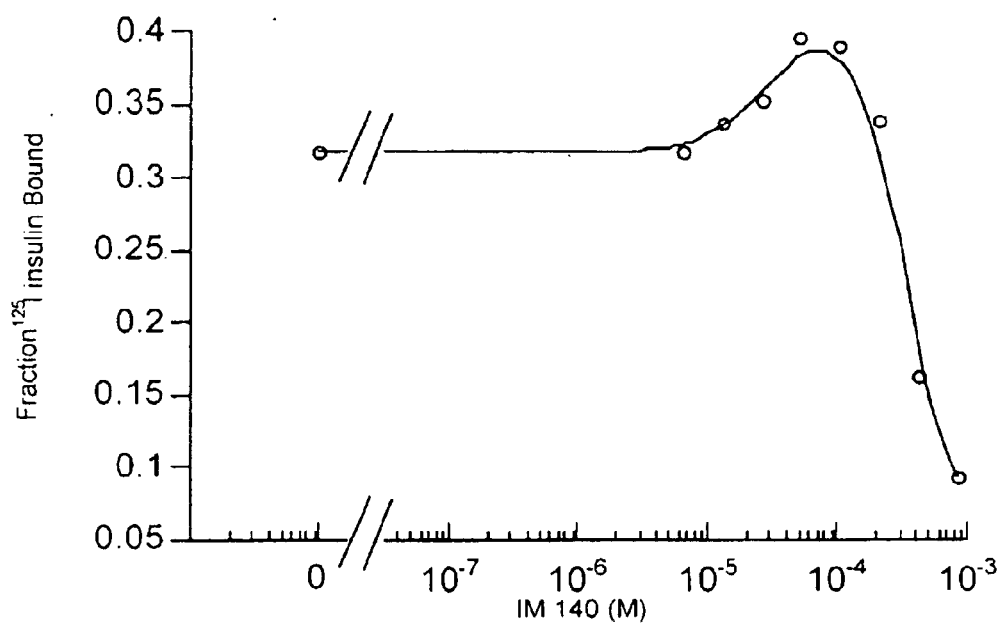
FIG. 45 demonstrates the effect of IM 140 on $^{125}$I insulin bound to human placental plasma membranes (○), expressed as a fraction of total $^{125}$I insulin added, where each data point is the mean of a triplicate determination.
Figure 46:
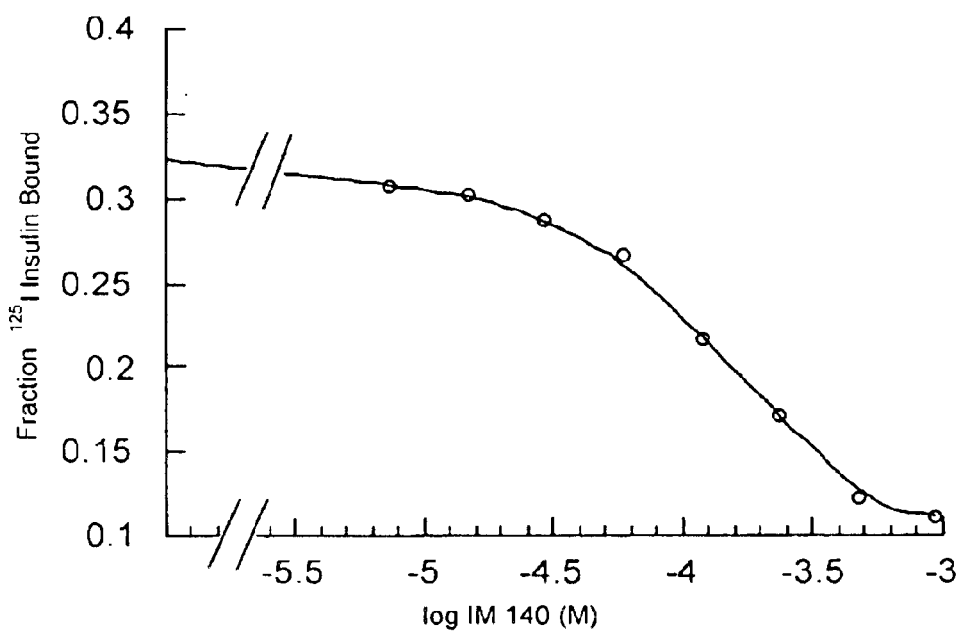
FIG. 46 represents the effect of IM 140 on $^{125}$I insulin bound to WGA.IR (○), expressed as a fraction of total $^{125}$I insulin added, where each data point is the mean of a triplicate determination.

The effect of IM 140 on $^{125}$I insulin binding to insulin receptors prepared from a number of sources is complex, as is evident from FIGS. 45 and 46. At low micromolar concentrations, IM 140 causes an increase in $^{125}$I insulin binding with an apparent EC50 of 10–20 μM. Maximal $^{125}$I insulin binding occurs at concentrations of about 80–100 μM. FIG. 45 clearly shows that concentrations above 100 μM cause a dose dependent inhibition of $^{125}$I insulin binding with an apparent Ki of between 250 and 570 μM.

The complicated nature of the $^{125}$I insulin binding isotherm can be explained by a similar mechanism as described for IM 129. However, IM 140 is likely to cross-link the α1 and α2 sites of adjacent α-subunits, because it activates the insulin receptor. In fact, as described below, IM 140 is also synergistic with insulin, indicating that both insulin and IM 140 interact with the receptor in a similar manner. However, the initial increase in $^{125}$I insulin that corresponds to the activation of receptors, indicates that IM 140 must also cause a change in the receptor that allows additional molecules of tracer insulin to bind. This change may be analogous in mechanism to that described earlier for IM 129 and insulin.

Effect on Biological Activity

Figure 47:
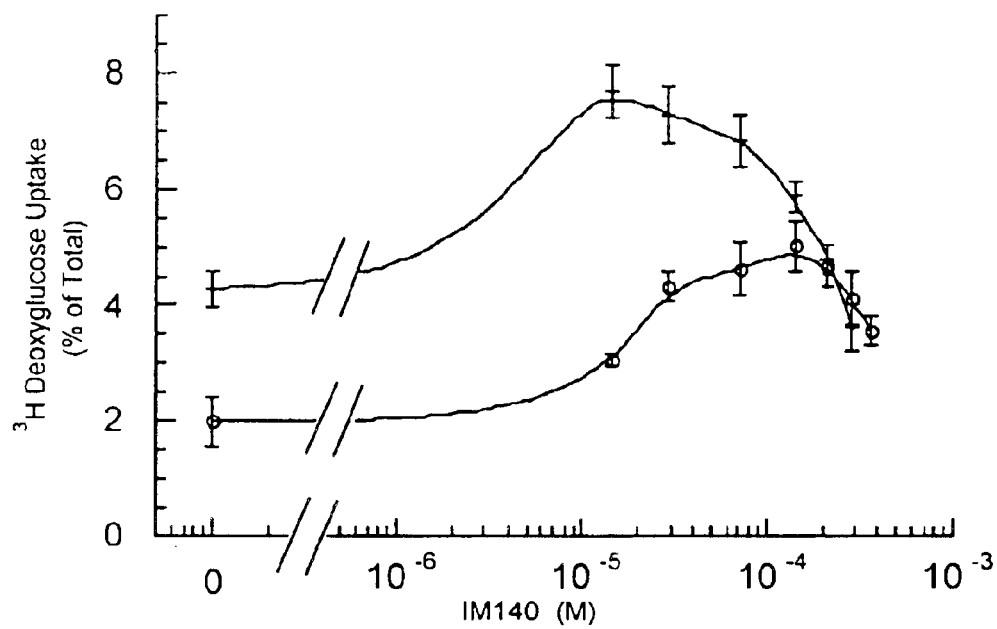
FIG. 47 shows the effect of IM 140 on total (presence of 2 nM insulin) (+) and basal (no insulin) (○) $^3$H-deoxyglucose uptake by 3T3L1 cells expressed as a percentage of total $^3$H-deoxyglucose added to cells, where each point is the mean of a triplicate determination±one standard deviation.
Figure 48:
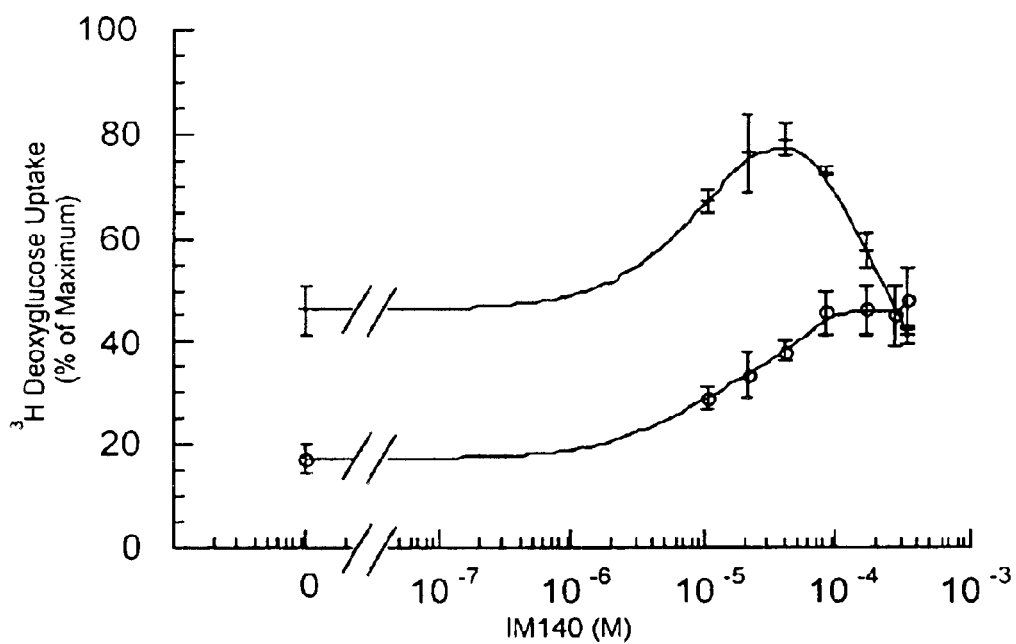
FIG. 48 shows the effect of IM 140 on total (presence of 2 nM insulin) (+) and basal (no insulin) (○) $^3$H-deoxyglucose uptake by 3T3L1 cells, where glucose transport is expressed as a percentage of a maximal 100 nM dose of insulin, and where each point is the mean of a triplicate determination±one standard deviation.
Figure 49:
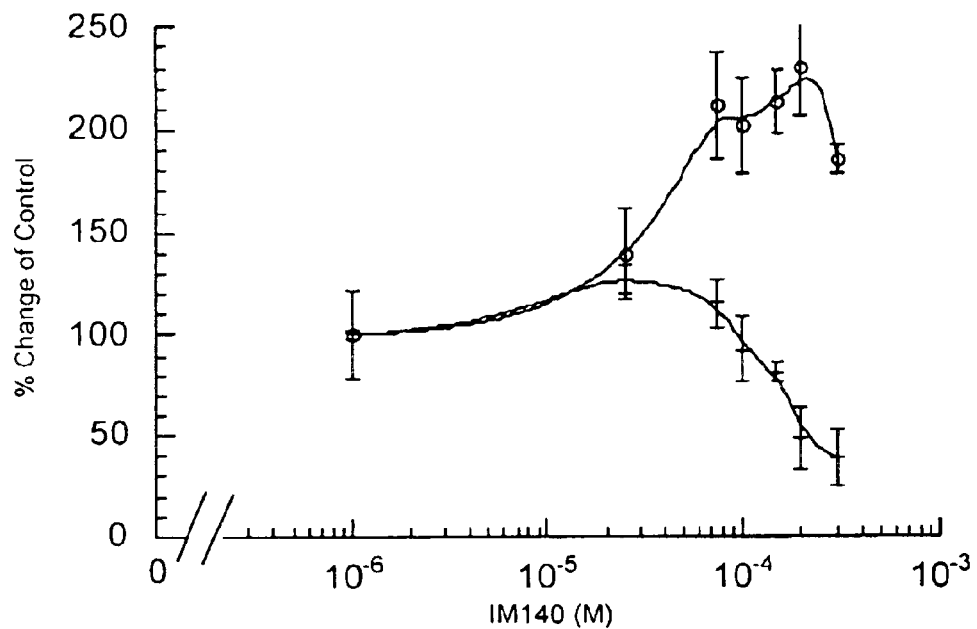
FIG. 49 illustrates the effect of IM 140 on $^{125}$I insulin binding (+) and $^3$H-deoxyglucose (○) in 3T3L1 adipocyte cells, where each isotherm is expressed as a percentage of buffer control and each point is the mean of a triplicate determination±one standard deviation.
Figure 51:
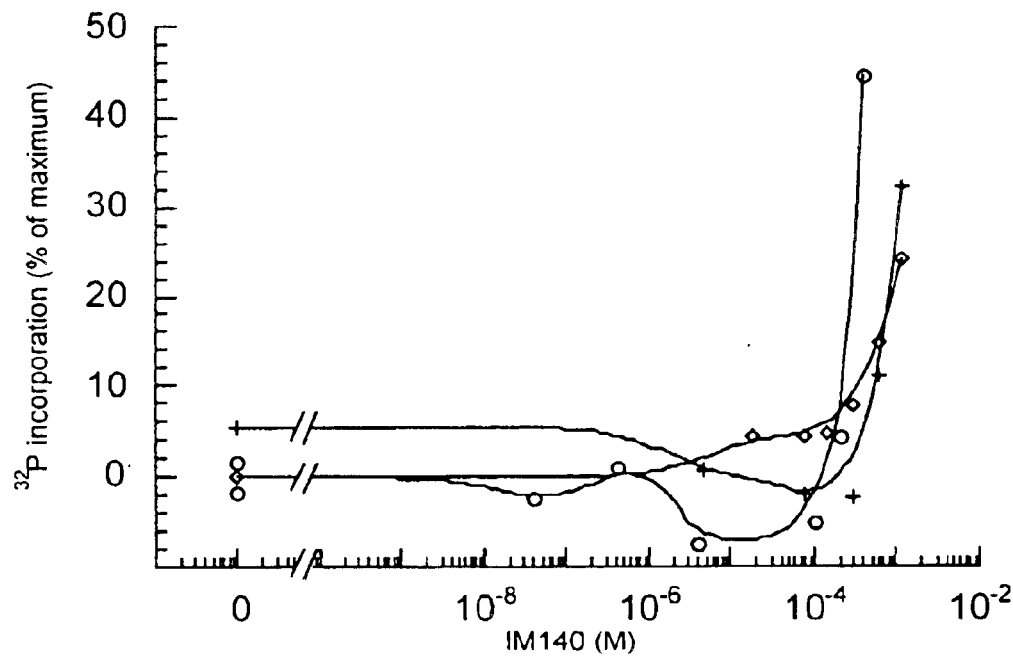
FIG. 51 demonstrates the effect of IM 140 on $^{32}$P incorporation into FYF peptide in three experiments, expressed as a percentage of maximal $^{32}$P incorporation (200 nM dose of insulin) into FYF peptide.
Figure 52:
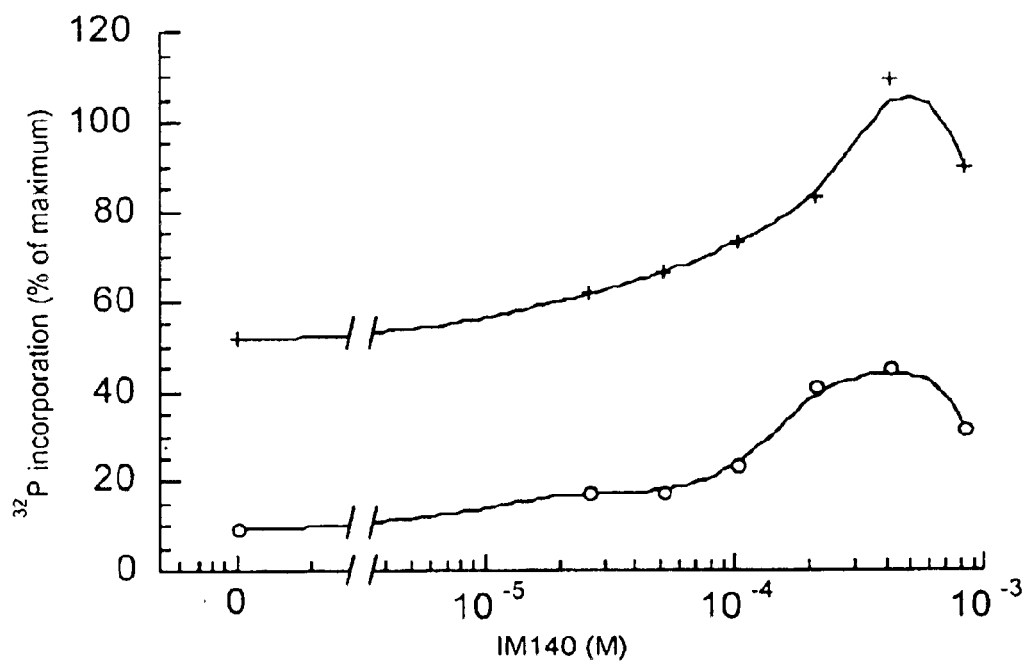
FIG. 52 demonstrates the effect of IM 140 on the total (in the presence of 100 nM insulin) (+) and basal (absence of insulin) (○) $^{32}$P incorporation into FYF peptide, expressed as a percentage of total $^{32}$P-γ-ATP added to reactions and where data points are expressed as the mean of a duplicate determination. Immunoprecipitated WGA.IR was used as the source of tyrosine kinase activity.
Figure 53:
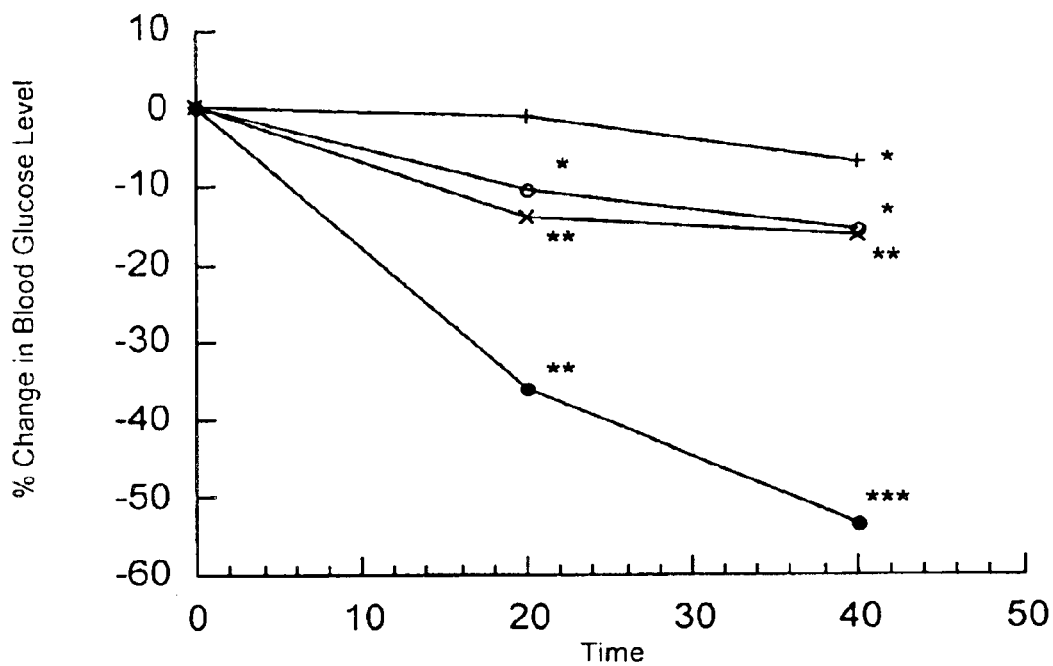
FIG. 53 illustrates the effect of IM 140 on blood glucose levels in streptozotocin induced diabetic mice. The scatter plot shows the effect of IM 140 at 21 μmol/kg (+), 30 μmol/kg (○), 37 μmol/kg (x) and human insulin at 2 U/kg over a period of 40 minutes. A significant change in blood glucose levels in an unpaired 1-tail t-test are indicated by a single asterisk where p<0.05, a double asterisk where p<0.01 and a triple asterisk * * * where p<0.001.

IM 140 is an agonist of insulin action because, as FIGS. 47 to 49 illustrate, it activates glucose transport in 3T3L1 cells, as FIGS. 51 and 52 illustrate, it causes phosphorylation of an exogenous insulin receptor tyrosine kinase substrate by insulin receptors of differing levels of purity and, as FIG. 53 demonstrates, lowers blood glucose levels in experimentally induced diabetic mice. IM 140 has an efficacy of 25–40% compared with insulin (inter experimental variation) and exhibits a bi-phasic dose-response curve with an apparent EC50 of 20–30 μM (Glucose transport). Moreover, as FIGS. 48 and 49 demonstrate IM 140 acts in a synergistic manner with a sub-maximal dose of insulin (2 nM) to stimulate glucose transport to 80% of maximal efficacy (100 nM insulin) at a concentration of 15 μM with an apparent EC50 of 8 μM. The observed difference in concentration of IM 140 effecting insulin binding and biological activity appears to be, at least in part, an artefact of inter-assay variation. When these parameters were measured using identical receptor sources (3T3L1 adipocyte cells), identical buffers and the same temperature, IM 140 was found to effect each assay over a similar concentration range, as illustrated in FIG. 49.

FIG. 51 shows that IM 140 also promotes the ATP-dependent phosphorylation of endogenous FYF peptide in a dose dependent manner. FIG. 52 indicates that when immunoprecipitated WGA.IR receptors are used as the source of tyrosine kinase activity, IM 140 promotes phosphorylation of endogenous FYF peptide in a bi-phasic manner. The immunoprecipitated WGA.IR receptors were only stimulated by a 100 fold excess of IGF-1 relative to insulin, indicating that the preparation was IGF-1 receptor free. This indicates that the phosphorylation of exogenous FYF peptide substrate was via the insulin receptor.

FIG. 53 demonstrates that IM140 significantly lowers blood glucose levels in diabetic mice with an efficacy of about 25% of human insulin at a dose of 35 μmol/kg. Preliminary studies also indicate that IM 140 does not decrease blood glucose levels in diabetic mice at a concentration of 100 μmol/kg. Therefore IM 140 displays a bi-phasic dose response curve in vivo with a peak activity of 20–40 μmol/kg and an EC50 of 15 μmol/kg.

Figure 50:
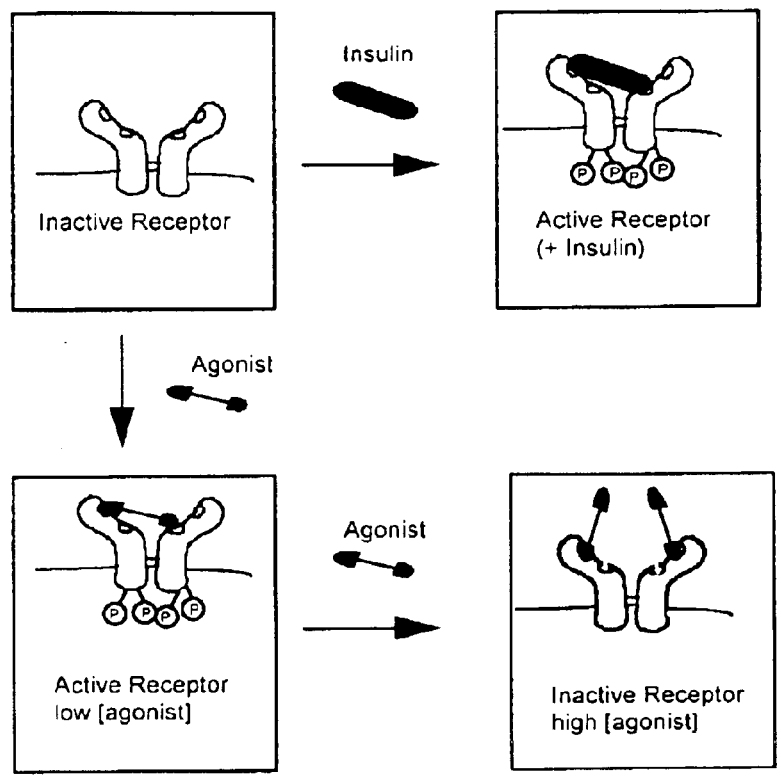
FIG. 50 represents a possible mechanism for agonist activation of insulin receptors, in which two alpha-beta halves of the insulin receptor, joined by disulfide bonds are illustrated, activated receptors are phosphorylated on their β-subunits, insulin is represented by oblong shaped objects and agonist molecules are represented by dumbbell shaped objects.

The bi-phasic dose response curve is analogous to growth hormone activation of its receptor. This indicates that IM 140 may be activating the insulin receptor by cross-linking its α-subunits. This is consistent with the model of insulin's interaction with its receptor proposed by P. De Meyts (14) and L. Schaffer (15). They propose that insulin activates the insulin receptor by cross-linking the α1 and α2 sites on adjacent insulin receptor α-subunits. IM 140 presumably contains some features that also enable it to cross-link these sites. The bell shaped dose response curve can then be explained by high concentrations of IM 140 binding each of the α-subunits thereby preventing cross-linking of the receptor (FIG. 50). IM compounds that are antagonists would lack some of the features of IM 140 or due to size or conformational restraints may be unable to interact concomitantly with both the α1 and α2 sites. Antagonist compounds may be similar to growth hormone mutants that are modified at one of their receptor contact sites which leads to them becoming potent antagonists of hGH.

Specificity

Figure 54:
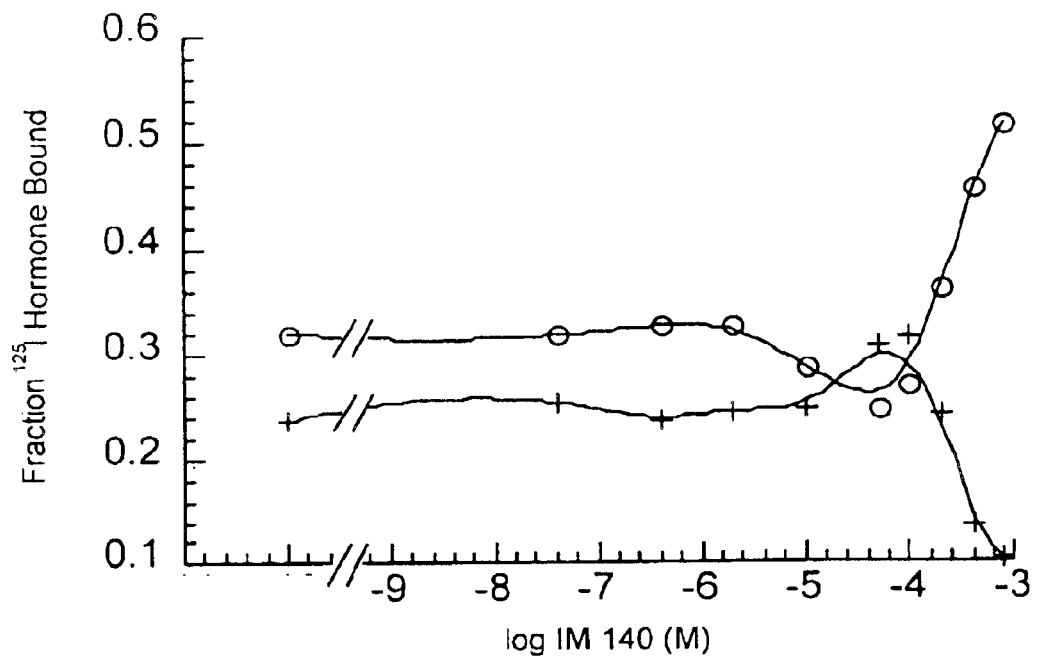
FIG. 54 illustrates the effect of IM 140 on $^{125}$I IGF-1 bound (○) and $^{125}$I insulin bound (+) to human placental plasma membranes expressed as a fraction of total $^{125}$I IGF-1 and $^{125}$I insulin added respectively, where each data point is the mean of a triplicate determination.
Figure 55:
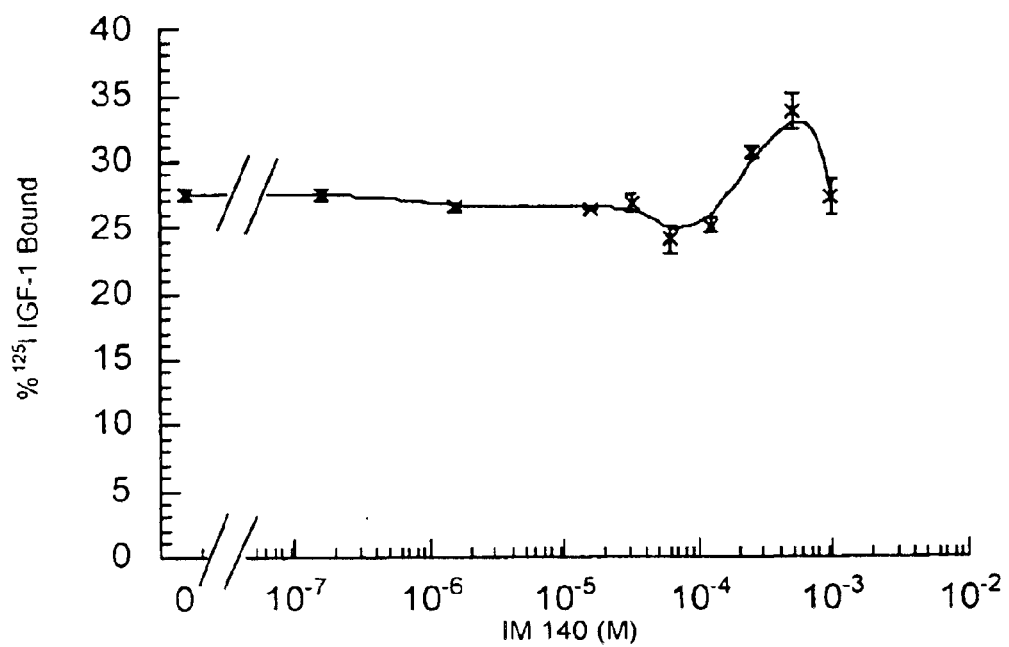
FIG. 55 illustrates the effect of IM 140 on $^{125}$I IGF-1 bound (x) to WGA.IR expressed as a percent of total $^{125}$I IGF-1 added to assay tubes, where each data point is the mean of a triplicate determination±one standard deviation.

IM 140 effects $^{125}$I insulin and $^{125}$I IGF-1 binding to HPPM in a dose dependent and complex manner, as can be seen in FIG. 54. However, over the range of IM 140 tested, the compound does not compete for $^{125}$I IGF-1 binding to HPPM. In contrast, at high concentrations IM 140 promotes $^{125}$I IGF-1 binding to HPPM which may be a shift to the right of the bell shaped displacement curve observed for $^{125}$I insulin binding. FIG. 55 indicates that IM140 does not compete for $^{125}$I IGF-1 binding in WGA purified receptor preparations from solubilised CHO wild-type cells. These cells are almost devoid of insulin receptors but have high endogenous populations of IGF-1 receptors.

It is not surprising that IM 140 effects both IGF-1 binding and Insulin binding to membrane preparations considering the homology and degree of cross-reactivity between the hormones and their receptors. Each receptor probably has a common shaped binding domain that can accommodate either hormone in a structurally equivalent manner. This result suggests that IM 140 has features that allow it to interact more specifically with the insulin receptor than the IGF-1 receptor, within a common binding domain.

EXAMPLE 13

8,8'-[Carbonylbis[imino-3,1-phenylenecarbonylimino(4-methyl-3,1-phenylene) carbonylimino]]bis-1,3,5-naphthalenetrisulfonic acid hexasodium salt (IM 175)

Effect on Insulin Binding and Specificity

Figure 56:
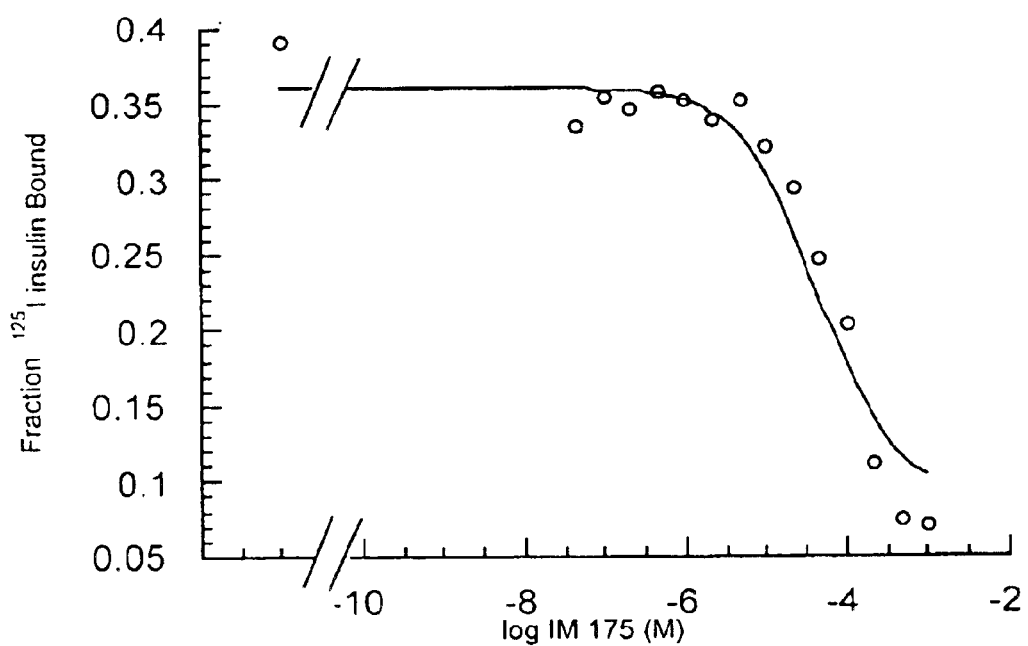
FIG. 56 shows the effect of IM 175 on $^{125}$I insulin bound to human placental plasma membranes (○), expressed as a fraction of total $^{125}$I insulin added and overlayed with a 1-site fit to the data (solid line).
Figure 57:
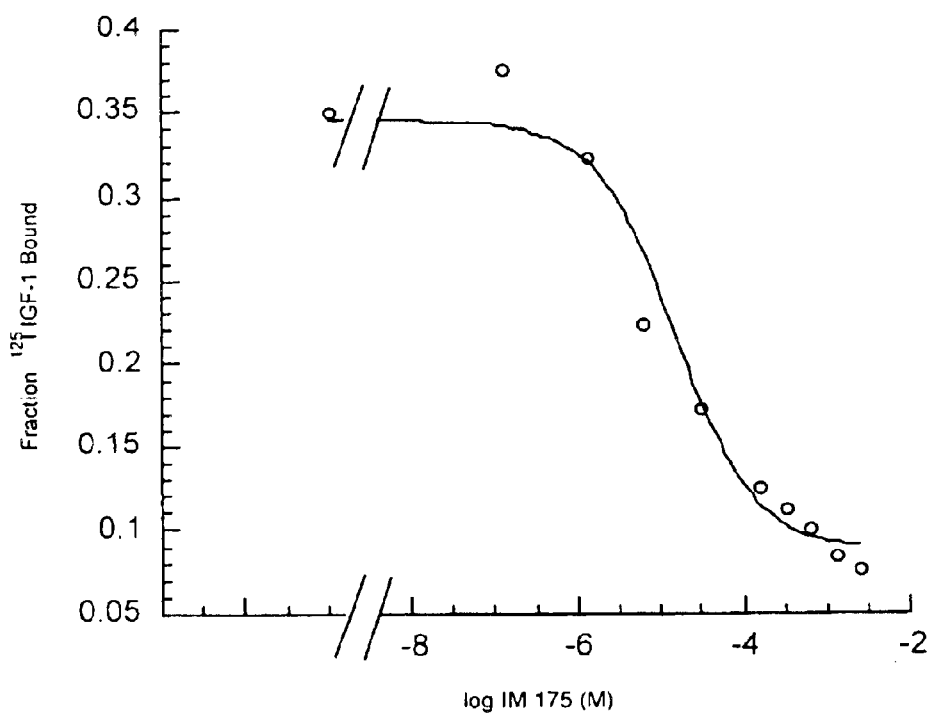
FIG. 57 represents the effect of IM 175 on $^{125}$I IGF-1 bound to human placental plasma membranes (○), expressed as a fraction of total $^{125}$I IGF-1 added and overlayed with a 1-site fit to the data (solid line), where each data point is the mean of a triplicate determination.

IM 175 competes with $^{125}$I insulin for binding to HPPM. FIG. 56 shows that the apparent Ki is 46–48 μM. IM 175 competes for binding according to a simple 1-site model and does not display the complex binding kinetics associated with other agonist compounds (eg IM 140). This may be because IM 175 is a larger compound and its size may prevent additional molecules of insulin interacting with the receptor. IM 175 also competes for $^{125}$I IGF-1 binding to HPPM with an estimated Ki of 9 μM as shown in FIG. 57), suggesting that it is a more potent competitor of IGF-1 binding than insulin binding. These results support the premise that both insulin and IGF-1 receptors have a common hormone binding site and also suggests that IM compounds are accommodated within this site. Differential specificity of compounds for either receptor is explained by structural differences between compounds.

Effect on Biological Activity

Figure 58:
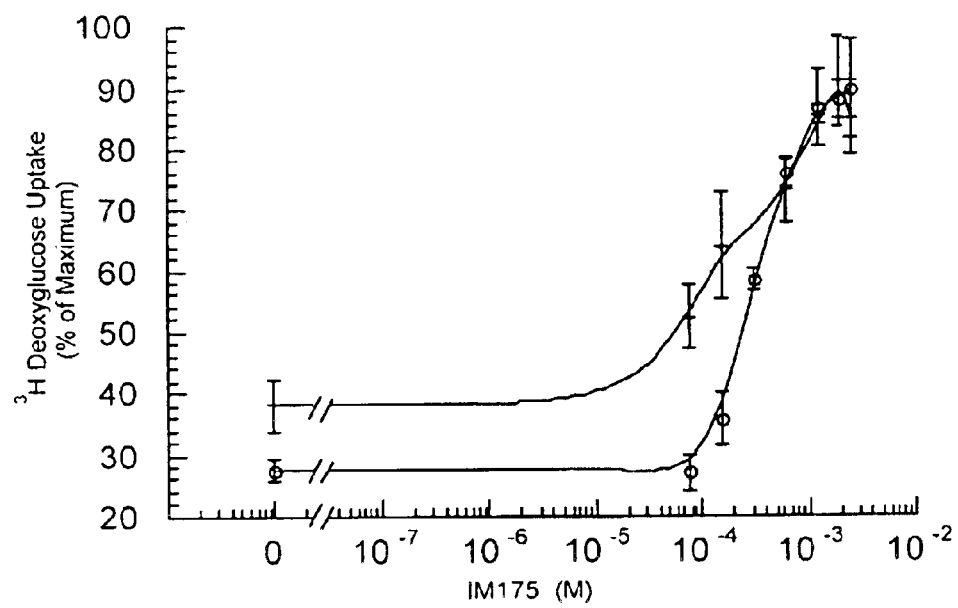
FIG. 58 is illustrative of the effect of IM 175 on total (presence of 2 nM insulin) (+) and basal (no insulin) (○) $^3$H-deoxyglucose uptake by 3T3L1 cells expressed as a percentage of total $^3$H-deoxyglucose added to cells, where each data point is the mean of a triplicate determination±one standard deviation.

IM 175 promotes glucose transport to levels approaching maximal stimulation by insulin in 3T3L1 adipocyte cells. FIG. 58 shows a typical experiment, the apparent EC50 is about 250 μM.

Figure 59:
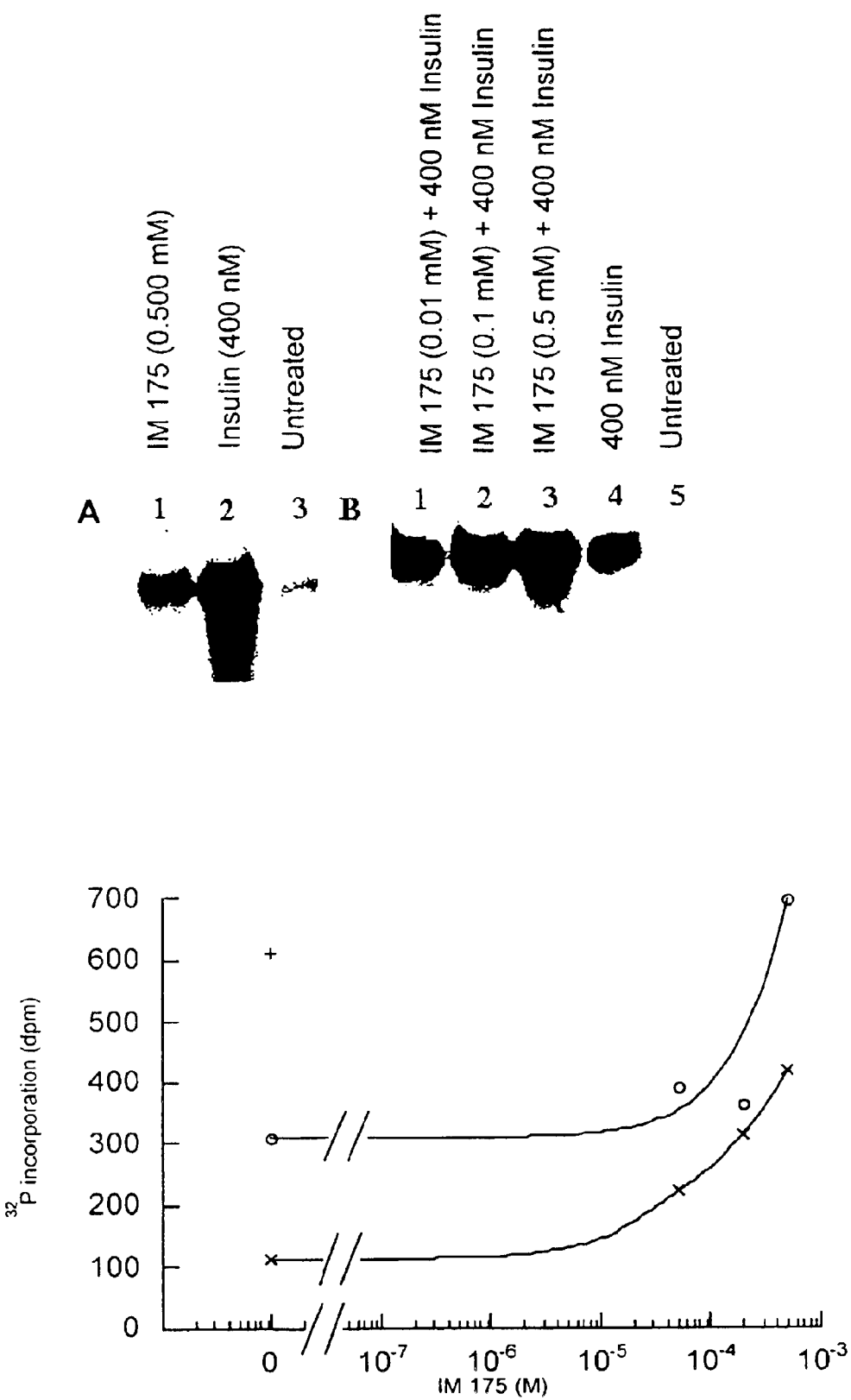
FIG. 59 demonstrates the incorporation of $^{32}$P into the 90 kDa protein band of immunoprecipitated insulin receptors, where the uppermost autoradiograph demonstrates phosphorylation of immunoprecipitated insulin receptor β-subunit in response to the indicated concentrations of IM 175 and insulin. Untreated lanes show phosphorylation in the absence of both insulin and IM 175, where both autoradiographs were taken from the same experiment, the leftmost (A) being a 48 hour exposure of the gel to X-ray film, and the rightmost (B) a 24 hour exposure. The lowermost plot demonstrates the effect of IM 175 on $^{32}$P incorporation into the 90 kDa protein band of immunoprecipitated insulin receptors in the presence (○) and absence (x) of 5 nM insulin compared to a 100 nM dose of insulin (+).
Figure 60:
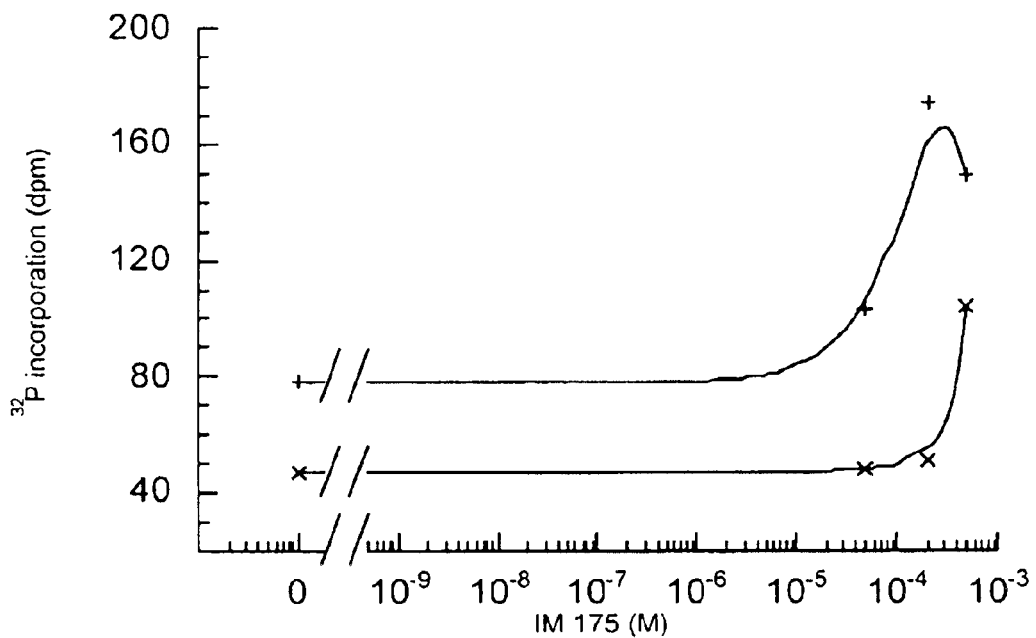
FIG. 60 demonstrates the effect of IM 175 on the incorporation of $^{32}$P into the 90 kDa protein band of immunoprecipitated IGF-1 receptors in the presence (+) and absence (x) of 2 nM IGF-1.

FIG. 59 demonstrates that IM 175 stimulates autophosphorylation of insulin receptor β-subunits with about 65% of the efficacy of a 100 nM dose of insulin. The immunoprecipitated insulin receptors used for this experiment are free of contaminating IGF-1 receptors, indicating that IM 175 specifically stimulates the phosphorylation of the insulin receptor. FIG. 60 illustrates that IM 175 can also stimulate the IGF-1 receptor, where immunoprecipitated IGF-1 receptors are free of insulin receptors. However, the dose-response curves indicate that IM175 has a lower potency on IGF-1 receptors than it does on insulin receptors.

IM 175 is structurally a symmetrical molecule and is a dimer of other IM compounds. It fits a general formula of ZXYXA-AXYXZ whereas IM 140 fits the general formula AXYXZ. This dimeric structure may be related to it having the highest efficacy of agonist compounds as other studies have implicated a role of symmetry and dimer structure in increased molecule activity. For example, small peptide agonists of the erythropoietin receptor and thrombopoeitin receptor, when dimerised, activate their respective receptors with greater potency than monomers. Additionally, bivalent anti insulin receptor antibodies activate insulin receptors, whereas monovalent Fab fragments do not.

EXAMPLE 14

2,4-dichloro-6-(N-(trifluoromethanesulfonyl)) sulfamoylphenyl 3,5-dichloro-2-hydroxybenzene sulfonate (IM 103)

Effect on Insulin Binding

Figure 61:
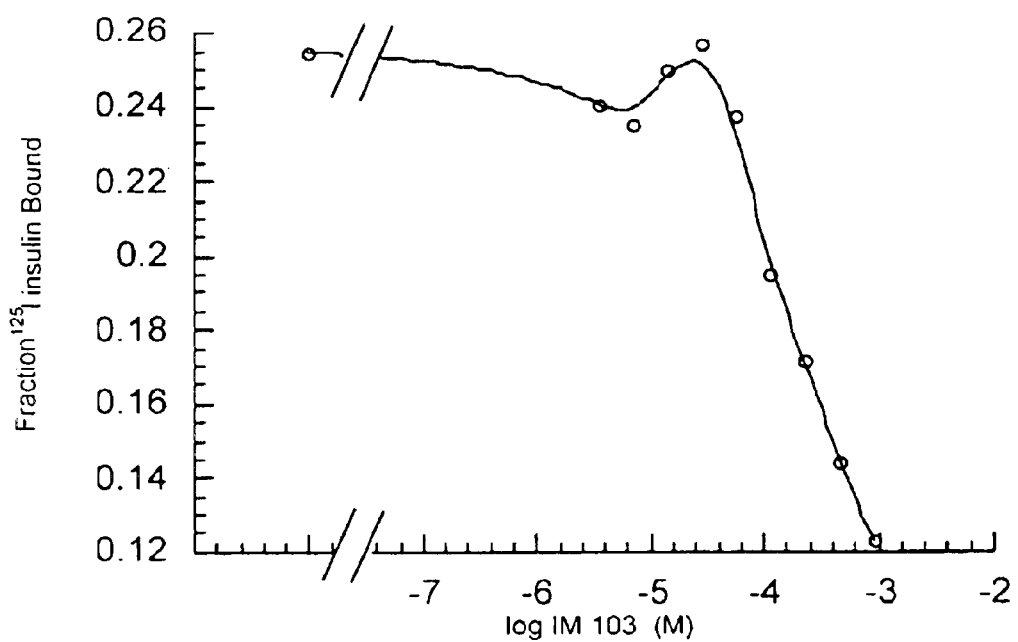
FIG. 61 shows the effect of IM 103 on $^{125}$I insulin bound to human placental plasma membranes (○), expressed as a fraction of total $^{125}$I insulin added, where each data point is the mean of a triplicate determination.
Figure 62:
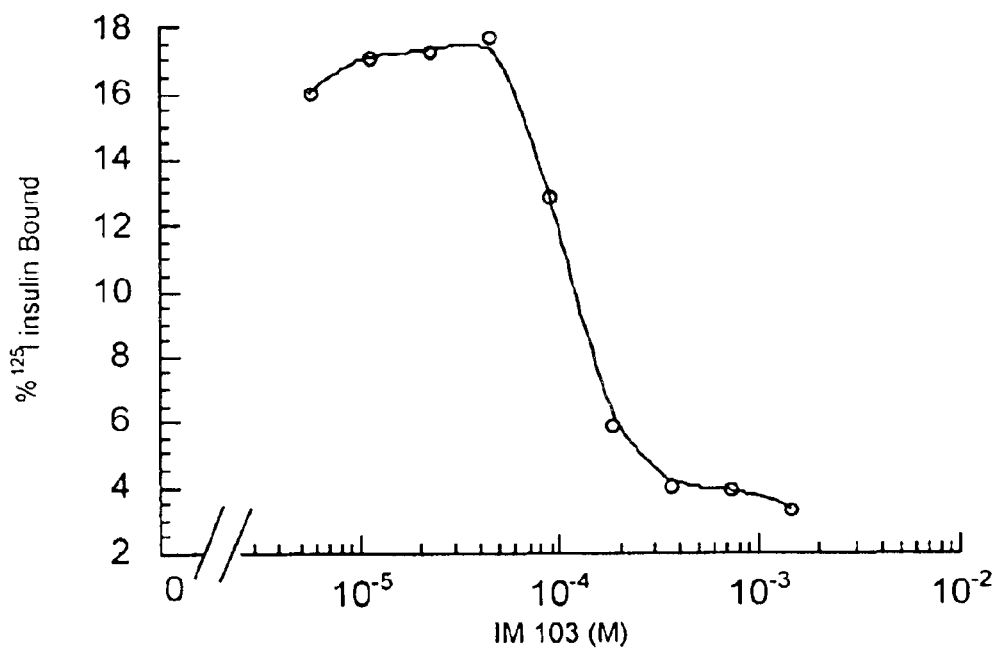
FIG. 62 illustrates the effect of IM 103 on $^{125}$I insulin bound to CHO.T11 cells (○) expressed as a fraction of total $^{125}$I insulin added, where each data point is the mean of a triplicate determination.
Figure 63:
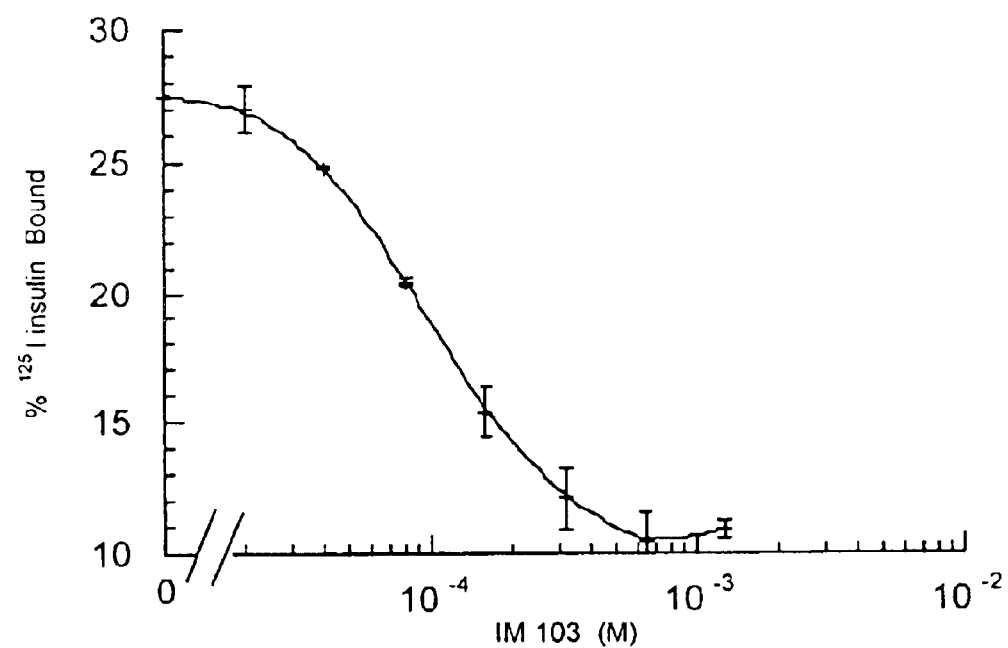
FIG. 63 shows the effect of IM 103 on $^{125}$I insulin bound to WGA.IR (+) expressed as a fraction of total $^{125}$I insulin added, where each data point is the mean of a triplicate determination±one standard deviation.

IM 103 competes with insulin for binding to insulin receptors in a dose dependent manner. The displacement plot is similar to other IM compounds (exemplified by IM 129 and IM 140) and does not fit a simple 1-site or 2-site model. The apparent inhibition constant is dependent upon receptor source and is 137±45 μM (LIGAND, 1-site fit) in HPPM, 132±29 μM in CHO.T11 cells and 83 μM in WGA.IR receptors, as can be seen in FIGS. 61, 62 and 63 respectively.

Effect on Biological Activity

Figure 64:
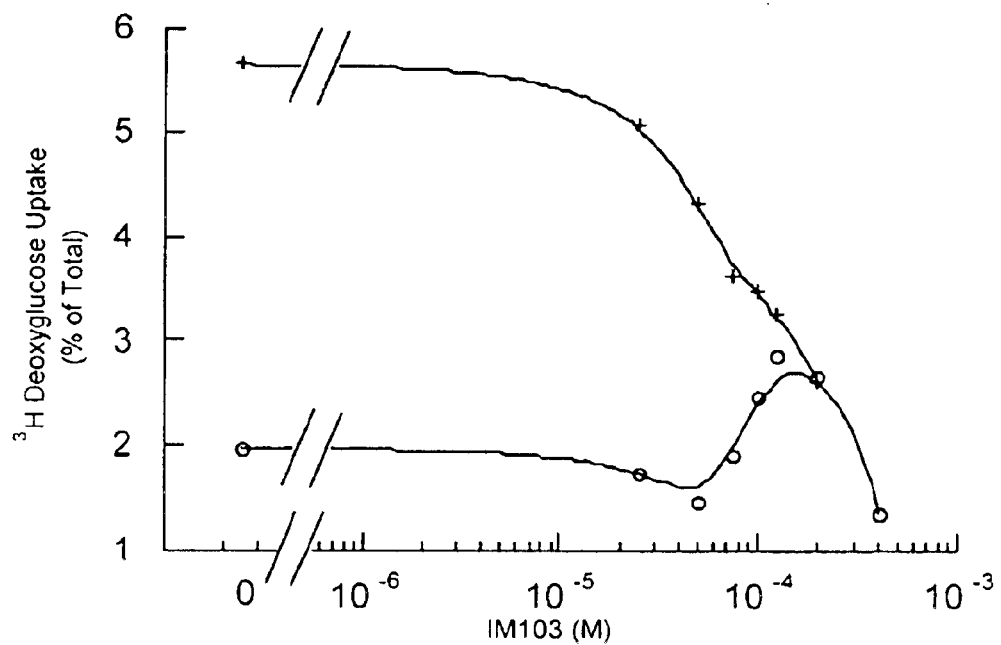
FIG. 64 shows the effect of IM 103 on total (presence of 2 nM insulin) (+) and basal (no insulin) (○) $^3$H-deoxyglucose uptake by 3T3L1 cells expressed as a percentage of total $^3$H-deoxyglucose added to cells, where each point is the mean of a triplicate determination.

IM 103 is an agonist of insulin action displaying a bi-phasic biological dose response curve with an apex at concentration of 110 μM and an apparent EC50 of 45±7 μM, as illustrated by FIG. 64. The efficacy is about 15% of that achieved at a maximal dose of insulin (100 nM). IM 103 abolishes the insulin stimulation of glucose transport in a dose dependent manner. However the dose response curve indicates complex kinetics.

Specificity

Figure 65:
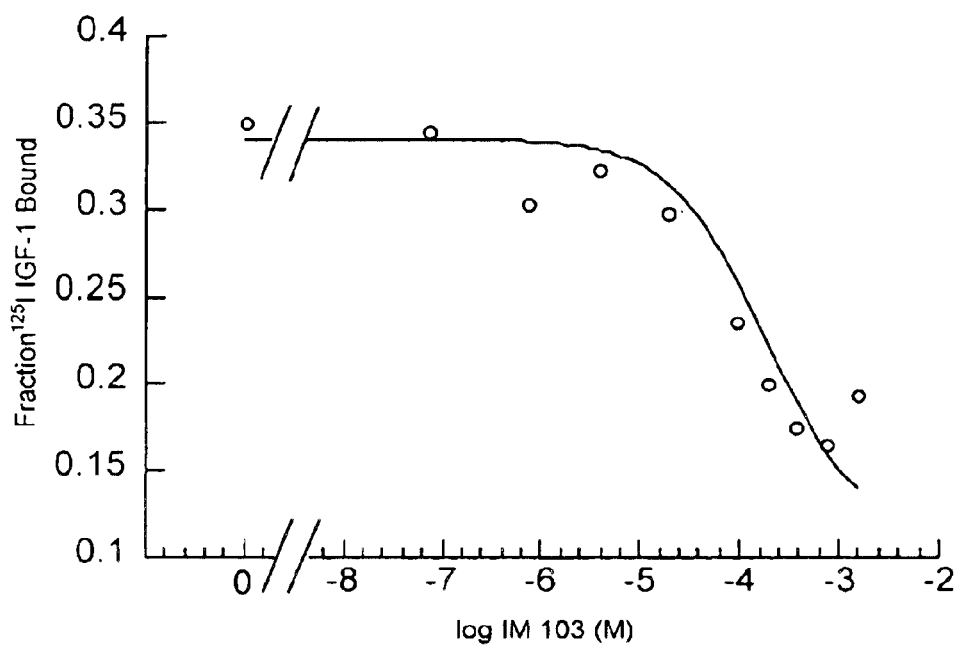
FIG. 65 illustrates The effect of IM 103 on $^{125}$I IGF-1 bound to human placental plasma membranes (○) expressed as a fraction of total $^{125}$I IGF-1 added and overlayed with a 1-site fit to the data (solid line), where each data point is the mean of a triplicate determination.

IM 103 displaces $^{125}$I IGF-1 binding from HPPM in a dose dependent manner with an apparent Ki of 59 μM (LIGAND estimated 1-site fit), as can be seen in FIG. 65 which compares with a Ki for $^{125}$I insulin binding of 137±45 μM (LIGAND estimated 1-site fit). Thus, IM 103 appears to have a higher specificity for IGF-1 receptors than insulin receptors.

Modifications and variations such as would be apparent to the skilled addressee are considered to fall within the scope of the present invention.

REFERENCES

1. Hubbard et at. Nature (1994) 372 746–54;
2. Hubbard Embo J. (1997) 16 5572–81
3. Garrett et al. Nature (1998) 394 395–99
4. Lou et al. Science (1999) 285 1077–80
5. Kahn et al. J. Biol. Chem. (1974) 249 2249–2257

6. Hammond et al. Am. J. Physiol. (1997) 272 E113644
7. De Meyts et al. Biochem. Biophys. Res. Commun. (1973) 55 154–161
8. Helmerhorst Biochem. Biophys. Res. Commun. (1987) 147 399–407
9. Pollet et al. J. Biol. Chem. (1977) 252 5828–5834
10. Donner Proc. Nati. Acad. Sci. USA (1980) 77 3176–3180
11. Corin and Donner J. Biol. Chem. (1982) 257 104–110
12. Helmerhorst and Yip Biochemistry (1993) 32 2356–62
13. Donner and Yonkers J. Biol. Chem. (1983) 258 9413–8
14. De Meyts Bull. Mem. Acad. R Med. Belg. (1994) 149 181–90
15. Schaffer Eur. J. Biochem. (1994) 221 1127–32
16. Harmon et al. J. Biol. Chem. (1983) 258 6875–6881
17. Kohanski and Lane J. Biol. Chem. (1985) 260 5014–5025
18. Maturo and Hollenberg Proc. Natl. Acad. Sci. USA (1978) 75 3070–3074
19. Mortensen et al. Biochem. J. (1992) 281 735–743
20. Varma et al. Biochem Mol Biol Int (1994) 32 807–17
21. Li, et al. (1991). J. Biol. Chem. 266, 7051-7057
22. Konstantopoulos Doctor of Philosophy Thesis, Department of Medicine, University of Melbourne (1997) 288 pages
23. Isakoff et al. Proc. Nati. Acad. Sci. USA (1995) 92 10247–51
24. Soos et al. Proc. Natl. Acad. Sci. USA (1989) 86 5217–21
25. Steele-Perkins and Roth J. Biol. Chem. (1990) 265 9458–63
26. Hem, et al. P Lab Animals (1998) 32(4) 364–368
27. Djuric et al. J. Med. Chem. (1989), 32,1145–1147
28. Harper et al. J. Med. Chem. (1994), 37, 2411–2420 at 2419
29. Sawyer et al. J. Med. Chem. (1993), 36, 3982–3984, on page 3982.

What is claimed is:

1. A method for treating a patient suffering from one or more insulin related ailments selected from the group consisting of hyperglycemia and hyperglycemia associated with diabetes mellitus, which method comprises the step of: administering to a patient in need thereof a therapeutically effective amount of a non-peptidyl compound, which possesses one or more ionic and hydrophobic chemical moieties spatially located so as to mimic the spatial location of at least an ionic or a hydrophobic amino acid residue of insulin and which binds to the insulin binding site of the insulin receptor, wherein said compound is an insulin agonist.

2. A method according to claim 1, wherein the ionic amino acid residue is selected from the group consisting of: A21 Asn, B21 Glu and A17 Glu.

3. A method according to claim 1, wherein the ionic and hydrophobic amino acid residue(s) is(are) selected from the group consisting of: A21 Asn, B21 Glu, A17 Glu, B24 Phe, B25 Phe, A19 Tyr, B12 Val, B16 Tyr, A2 Ile, A3 Val and A1 Gly.

4. A method according to claim 1, wherein at least one amino acid is selected from the group consisting of: A17 Glu, B21 Glu and A21 Asn; and at least one amino acid is selected from the group consisting of: B24 Phe, B25 Phe, A19 Tyr, B12 Val and B16 Tyr.

5. A method according to claim 1, wherein the non-peptidyl compound possesses ionic and hydrophobic chemical moieties spatially located so as to mimic ionic and hydrophobic residues associated with at least one of the following groups of amino acid residues:

(i.) A21 Asn, B21 Glu, A17 Glu, B24 Phe, B25 Phe;
(ii.) A21 Asn, B21 Glu, B24 Phe, B25 Phe;
(iii.) A21 Asn, B21 Glu, B24 Phe, B25 Phe, A1 Gly, A2 Ile, A3 Val;
(iv.) A21 Asn, B21 Glu, A17 Glu, A19 Tyr, A1 Gly, A2 Ile, A3 Val;
(v.) A21 Asn, B21 Glu, A17 Glu, B12 Val, A1 Gly, A2 Ile, A3 Val;
(vi.) A21 Asn, B21 Glu, B12 Val, A1 Gly, A2 Ile, A3 Val;
(vii.) A21 Asn, B21 Glu, A17 Glu, B16 Tyr, A1 Gly, A2 Ile, A3 Val;
(viii.) A21 Asn, B21 Glu, A17 Glu, A19 Tyr, B12 Val, B16 Tyr;
(ix.) A21 Asn, B21 Glu, A19 Tyr, B12 Val, B16 Tyr;
(x.) A21 Asn, B21 Glu, A17 Glu, B24 Phe, B25 Phe, A19 Tyr, B132 Val, B16 Tyr;
(xi.) A21 Asn, B21 Glu, B24 Phe, B25 Phe, A19 Tyr, B12 Val, B16 Tyr;
(xii) A21 Asn, B21 Glu, B24 Phe, B25 Phe, B12 Val, B16 Tyr;
(xiii.) A21 Asn, B21 Glu, A17 Glu, B24 Phe, B25 Phe, A19 Tyr;
(xiv.) A21 Asn, B21 Glu, B24 Phe, B25 Phe, A19 Tyr;
(xv.) A21 Asn, A17 Glu, B24 Phe, B25 Phe, A19 Tyr;
(xvi.) B21 Glu, A17 Glu, B24 Phe, B25 Phe, A19 Tyr;
(xvii.) A21 Asn, B21 Glu, A17 Glu, B24 Phe, B25 Phe, B12 Val;
(xviii.) A21 Asn, B21 Glu, B24 Phe, B25 Phe, B12 Val;
(xix.) A21 Asn, A17 Glu, B24 Phe, B25 Phe, B12 Val;
(xx.) B21 Glu, A17 Glu, B24 Phe, B25 Phe, B12 Val;
(xxi.) A21 Asn, B21 Glu, A17 Glu, B24 Phe, B25 Phe, B16 Tyr;
(xxii.) A21 Asn, B21 Glu, B24 Phe, B25 Phe, B16 Tyr;
(xxiii.) A21 Asn, A17 Glu, B24 Phe, B25 Phe, B16 Tyr;
(xxiv.) B21 Glu, A17 Glu, B24 Phe, B25 Phe, B16 Tyr;
(xxv.) A21 Asn, B21 Glu, A17 Glu, A19 Tyr, B12 Val, B16 Tyr;
(xxvi.) A21 Asn, B21 Glu, B24 Phe, A19 Tyr, B12 Val, B16 Tyr;
(xxvii.) A21 Asn, B21 Glu, A17 Glu, A19 Tyr, B12 Val, B16 Tyr;
(xxviii.) B21 Glu, A17 Glu, B24 Phe, A19 Tyr, B12 Val, B16 Tyr;
(xxix.) A21 Asn, B21 Glu, A17 Glu, B25 Phe, A19 Tyr, B12 Val, B16 Tyr;
(xxx.) A21 Asn, B21 Glu, B25 Phe, A19 Tyr, B12 Val, B16 Tyr;
(xxxi.) A21 Asn, A17 Glu, B25 Phe, A19 Tyr, B12 Val, B16 Tyr; and
(xxxii.) B21 Glu, A17 Glu, B25 Phe, A19 Tyr, B12 Val.

6. A method according to claim 1, wherein the non-peptidyl compound has the following formula:

$$AXYXZ_n \qquad \text{(formula 1)}$$

where A is W or VXW;
V is $V_1$ or $V_2$;
V is substituted with up to two X groups;
$V_1$ is a phenyl or 6 membered heteroaromatic ring, optionally substituted with up to 5 $R_1$ groups;

V₂ is a 5 member ring system which may incorporate up to 4 hetero atoms which may be independently a nitrogen atom, a nitrogen atom optionally substituted with R₂, oxygen or sulfur, the ring system being optionally substituted with up to 4 R₁ groups;

W is W₁ or W₂ or W₃;

W is substituted with up to two X groups;

W₁ is V₁;

W₂ is a fused bicyclic ring system comprising rings of 5 or 6 atoms, which may incorporate up to 4 hetero atoms, which may be independently a nitrogen atom, a nitrogen atom optionally substituted with R₂, oxygen or sulfur, the system being optionally substituted with up to seven R₁ groups;

W₃ is —N(R₂)R'₂;

R₁ is independently H, OH, alkyl, alkenyl, alkynyl, alkoxy, alkanol, hydroxyalkoxy, haloalkyl, haloalkoxy, halogen, SH, thioalkyl, cyano (—CN), N(R₂)R'₂, phenyl, phenyl optionally substituted with up to five alkyl groups of 1 to 3 carbon atoms or up to five halogen atoms, benzyl, phenethyl, nitro, —COR₃, —R₅COR₃, —R₅SOR₃, —R₅SO₂R₃, —SO₂N(R₂)R'₂ or azido;

R₂ and R'₂ are independently H, alkyl of 1 to 6 carbon atoms, alkenyl of 3 to 6 carbon atoms, alkynyl of 3 to 6 carbons, hydroxyalkyl of 2 to 6 carbons, alkoxy of 2 to 6 carbons, haloalkyl, haloalkenyl, haloalkoxy, benzyl, benzyl optionally substituted with up to four R₁ groups, phenylethyl, phenylethyl optionally substituted with up to four R₁ groups, arylalkyl, and where R₂ and R'₂ can also be joined to form cyclic structures;

R₃ is independently H, OH, alkyl, alkenyl, alkynyl, alkoxy, alkanol, hydroxyalkoxy, —R₄N(R₂)R'₂, mesyl, triflouromesyl, —NHSO₂CH₃ or —NHSO₂CF₃;

R₄ is independently a bond, alkyl, alkenyl or alkynyl;

X is independently, a bond, —R₄N(R₂)R₄—, —R₄N=NR₄—, —R₄N(R₂)—N(R₂)R₄—, —R₄OR₄—, —R₄SR₄—, —R₅—, —R₅O—, —R₅S—, —R₅N(R₂)—, —SO—, sulfonyl (—SO₂—), —CO—, —CONH—, —NHCONH—, —NHCO—, —CONHCO—, —CON(R₂)—, —RCOR₅—, —R₅COR₅N(R₂)R₅—, —N(R₂)CO— or —R₄N(R₂)R₄COR₄—;

R₅ is independently alkyl, alkenyl, alkynyl, alkoxy, alkanol, hydroxyalkoxy;

Y is either Y₁, Y₂ or Y₃;

Y is substituted with at least two, but optionally up to four X linking groups;

Y₁ is a fused bicyclic ring system comprising rings of 5 or 6 atoms which may incorporate up to 4 hetero atoms, which may be independently a nitrogen atom, a nitrogen atom optionally substituted with R₂, oxygen or sulfur, the ring system optionally independently incorporating a sulfoxide (SO), sulfone (SO₂) or carbonyl (CO) group and optionally up to seven R₁ groups;

Y₂ is a 6:6:6 or a 6:5:6 fused tricyclic system which may incorporate up to 4 hetero atoms which may be independently a nitrogen atom, a nitrogen atom optionally substituted with R₂, oxygen or sulfur, the ring system optionally independently incorporating a sulfoxide (SO), sulfone (SO₂) or carbonyl (CO) group, and the ring system being substituted with at least two, but optionally up to four X linking groups and optionally up to seven R₁ groups;

Y₃ is V₁;

Z is independently —R₆COOH, —R₆SO₃H, —R₆NO₂, —R₆SO₂H, —R₆SO₂NHR₂; —R₇SO₂NHCOR₄—N-trifluoromesylsulfonanidate, —OH, -2-yl-hydroxyethanoic acid (—CH(OH)COOH), -3-yl-2-hydroxypropanoic acid (—CH₂CH(OH)COOH)-2-yl-2-hydroxypropanoic acid (—CH(CH₃)(OH)COOH), -3-yl-2,3-dihydroxypropanoic acid (—CH(OH)CH(OH)COOH), -2-yl-2,3-dihydroxypropanoic acid (—C(CH₂(OH))(OH)COOH), -3-yl-2-hydroxypropan-3-one-1-oic acid (—COCH(OH)COOH, 2-yl-2-hydroxypropandioic acid (—C(COOH)(OH)COOH), -2-yl-propandioic acid (—C(COOH)(H)COOH), -4-yl-2-hydroxybutan4-one-1-oic acid (—COCH₂CH(OH)COOH, 2-yl-2-hydroxybutan-1,4-dioic acid (—C(OH)(COOH)CH₂COOH), 3-yl-2-hydroxybutan-1,4-dioic acid (—CH(CH(OH)COOH)COOH), 5-yl-tetrazole,

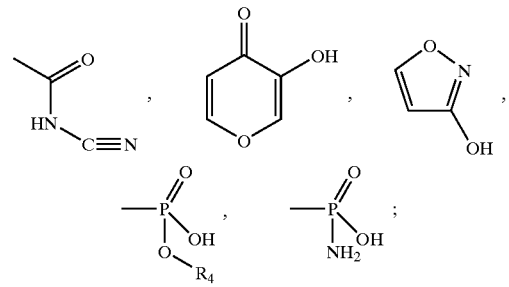

R₆ is independently a bond, alkyl, alkenyl, alkynyl, alkoxy, —CO(CH₂)ₙ—, where n is an integer between 0 and 4, alkanoic, alkenoic or alkynoic;

with the exception that where W₁ is an optionally substituted phenyl then Y₃ cannot be an optionally substituted phenyl.

7. A method according to claim 6, wherein the non-peptidyl compound is a dimer or heterodimer wherein the compounds are joined through a X linking group by way of their V or W groups.

8. A method according to claim 6, wherein when V is V₁ or V₂, then:

V₁ is selected from the group consisting of, benzene, pyridine, pyridazine, pyrimidine, pyrazine and triazine and is optionally substituted with up to 5 R₁ groups; and V2 is selected from the group consisting of, cyclopenta-1,3-diene, pyrrole, furan, thiophene, oxazole, isoxazole, pyrazole, imidazole, thiazole, isothiazole and triazole and is optionally substituted with up to 4 R₁ groups;

and W is W₂ then

W₂ is selected from the group consisting of naphthalene, quinoline, isoquinoline, phthalazine, naphthyridine, quinoxaline, quinazoline, cinnoline, pteridine, indole, benzothiophene, benzofuran, benzimidazole, indazole, benzoxazole, benzisooxazole, henzthiazole, benzisothiazole, purine, indoline and isoindoline and is optionally substituted with up to seven R₁ groups;

and Y is either Y₁ or Y₂ then

Y₁ is selected from the group consisting of croman, isochroman, benzofuran, cromene, 1,2,3,4-tetrahydronaphthalene, 1,4-dihydronaphthalene, indan, indene, benzopiperidine, indoline, isoindoline, quinoline, isoquinoline, phthalazine, naphthyridine, quinoxaline, quinazoline, cinnoline or pteridine, coumarin and 2,3-dihydrocoumarin and is optionally substituted with up to seven $R_1$ groups; and $Y_2$ is selected from the group consisting of 9H-xanthone, 9H-xanthene, phenoxathiin, phenoxathiin-10-oxide, phenoxathiin-10-dioxide, acridine, phenazine, phenothiazine, phenoxazine, phenothiazine-5-oxide, phenothiazine-5-dioxide, thiathrene-5-dioxide, thiathrene-5-oxide, carbazole, dibenzo[b,d]furan and dibenzo[b,d]thiophene and is optionally substituted with up to seven $R_1$ groups.

9. A method according to claim 6, wherein when A is VXW then: V is phenyl or pyrazole, optionally substituted with up to 5 $R_1$ groups; and when A is W or VXW then W is $W_1$, $W_2$ or $W_3$ wherein $W_1$ is phenyl optionally substituted with up to 5 $R_1$ groups;

$W_2$ is naphthalene or quinoline optionally substituted with up to seven $R_1$ groups wherein $R_1$ is independently H, OH, methyl, ethyl, propyl, nitro, methoxy, ethoxy, 2-hydroxyethoxy, chloro, fluoro or acetyl;

$W_3$ is —N($R_2$)$R_2$ wherein $R_2$ is propyl; X is independently, a bond, methoxy (—OCH$_2$), oxypropoxy (—O(CH$_2$)$_3$O—), hexenyloxy (—O(CH$_2$)$_4$CH=CH—), sulfonyloxy (—SO$_2$O—), methyl (—CH$_2$—), amidyl (—CONH—) or —NHCONH—; and Y is either $Y_1$ or $Y_2$ then $Y_1$ is croman, 4-H-chromen-4-one or napthalene optionally substituted with up to seven $R_1$ groups wherein $R_1$ is independently H, OH, methyl, ethyl, propyl, nitro, methoxy, ethoxy, 2-hydroxyethoxy, chloro, fluoro or acetyl;

$Y_2$ is 9H-xanthone optionally substituted with up to seven $R_1$ groups wherein $R_1$ is independently H, OH, methyl, ethyl, propyl, nitro, methoxy, ethoxy, 2-hydroxyethoxy, chloro, fluoro or acetyl;

$Y_3$ is phenyl optionally substituted with up to 5 $R_1$ groups wherein $R_1$ is independently H, OH, methyl, ethyl, propyl, nitro, methoxy, ethoxy, 2-hydroxyethoxy, chloro, fluoro or acetyl; and Z is independently —$R_6$COOH, —$R_6$SO$_3$H or —N-trifluoromesylsulfonarnidate wherein $R_6$ is independently a bond or propyl.

10. A method according to claim 6, wherein the non-peptidyl compound is selected from the following group of compounds:

(i.) 4,4'-Methylenebis[3-hydroxy-2-naphthalenecarboxylic acid];

(ii.) 7-[3-(4-acetyl-2-ethyl-5-hydroxyphenoxy)propoxy]-3,4-dihydro-8-propyl-2H-1-benzopyran-2-carboxylic acid;

(iii.) 2,4-dichloro-6-(N-(trifluoromethanesulfonyl)) sulfamoylphenyl 3,5-dichloro-2-hydroxybenzenesulfonate;

(iv.) 7-[(4-acetyl-3-hydroxy-2-propylphenyl)methoxy]4-oxo-8-propyl4H-1-benzopyran-2-carboxylic acid;

(v.) 7-[3-(4-acetyl-3-methoxy-2-propylphenoxy) propoxy]-3,4-dihydro-8-propyl-2H-1-benzopyran-2-carboxylic acid;

(vi.) 3,4-dihydro-8-propyl-7-[[3-[2-ethyl-5-hydroxy-4-(1H-pyrazol-3-yl)phenoxy]propyl]oxy]-2H-1-benzopyran-2-carboxylic acid;

(vii.) 3,4-dihydro-8-propyl-7-[[3-[2-ethyl-5-hydroxy-4-ethoxyphenoxy]propyl]oxy]-2H-1-benzopyran-2-carboxylic acid;

(viii.) 3-[4-[7-carboxy-9-oxo-3-[3-[2-ethyl-4-(4-fluorophenyl)-5-hydroxyphenoxy]propoxy]-9H-xanthene]]propanoic acid;

(ix.) 8-propyl-7-(quinol-2'-ylmethoxy)-3,4-dihydro-2H-1-benzopyran-2-carboxylic acid;

(x.) 7-(naphth-2'-ylmethoxy)-8-propyl-3,4-dihydro-2H-1-benzopyran-2-carboxylic acid;

(xi.) N-(trifluoromethanesulfonyl)-3,5-dinitro-4-(N',N'-dipropylamino)benzenesulfonamide;

(xii.) 8-propyl-7-[3-[4-(4-fluorophenyl)-2-ethyl-5-hydroxyphenoxy]propoxy]-3,4-dihydro-2H-1-benzopyran-2-carboxylic acid;

(xiii.) 3,4-dihydro-7-[[6-(4-methoxyphenyl)hexenyl]oxy]-8-propyl-2H-1-benzopyran-2-carboxylic acid; and (xiv.) 8,8'-[Carbonylbis[imino-3,1-phenylenecarbonyl-imino(4-methyl-3,1-phenylene)carbonylimino]]bis-1,3,5-naphthalenetrisulfonic acid.

11. A method for identifying a non-peptidyl compound possessing ionic and hydrophobic chemical moieties spatially located so as to mimic particular ionic and hydrophobic amino acid residues of insulin and which binds to the insulin binding site of the insulin receptor, said method comprising the steps of: (1) comparing the three dimensional structure of the non-peptidyl compound with a three dimensional pharmacophore of an active site of insulin; and (2) selecting a non-peptidyl compound with ionic and hydrophobic chemical moieties spatially located so as to mimic said site.

12. A method for determining whether a non-peptidyl compound identified according to the method of claim 11 is an agonist or an antagonist, said method comprising the step of: exposing the compound to an insulin or insulin like receptor and measuring the change in biological activity following exposure of the compound to the receptor.

13. A method according to claim 6 wherein $V_1$ is selected from the group consisting of: benzene, pyridine, pyridazine, pyrimidine, pyrazine and triazine.

14. A method according to claim 6 wherein $V_2$ is selected from the group consisting of: cyclopenta-1,3-diene, pyrrole, furan, thiophene, oxazole, isoxazole, pyrazole, imidazole, thiazole, isothiazole and triazole, optionally substituted with up to 4 $R_1$ groups.

15. A method according to claim 6 wherein $W_2$ is selected from the group consisting of: naphthalene, quinoline, isoquinoline, phthalazine, naphthyridine, quinoxaline, quinazoline, cinnoline, pteridine, indole, benzothiophene, benzofuran, benzimidazole, indazole, benzoxazole, benzisooxazole, benzthiazole, benzisothiazole, purine, indoline and isoindoline.

16. A method according to claim 6 wherein $R_2$ and $R'_2$ are joined to form cyclic structures selected from the group consisting of: pyrrolidine, piperidine, hexahydro-1H-azepine, morpholine and piperazine.

17. A method according to claim 6 wherein $Y_1$ is selected from the group consisting of: croman, isochroman, benzofuran, cromene, 1,2,3,4-tetrahydronaphthalene, 1,4-dihydronaphthalene, indan, indene, benzopiperidine, indoline, isoindoline, quinoline, isoquinoline, phthalazine, naphthyridine, quinoxaline, quinazoline, cinnoline pteridine, coumarin and 2,3-dihydrocoumarin.

18. A method according to claim 6 wherein $Y_2$ is selected from the group consisting of: 9H-xanthone, 9H-xanthene, phenoxathiin, phenoxathiin-10-oxide, phenoxathiin-10-dioxide, acridine, phenazine, phenothiazine, phenoxazine, phenothiazine-5-oxide, phenothiazine-5-dioxide, thiathrene-5-dioxide, thiathrene-5-oxide, carbazole, dibenzo[b,d]furan and dibenzo[b,d]thiophene.

19. A method for treating a patient suffering from one or more insulin related ailments selected from the group consisting of hypoglycemia, insulinomas, insulin and hypoglycemic drug overdose, gastric dumping syndrome and congenital hyperinsulinism, which method comprises the step of: administering to a patient in need thereof a therapeutically effective amount of a non-peptidyl compound which possesses one or more ionic and hydrophobic chemical moieties spatially located so as to mimic the spatial location of at least an ionic or a hydrophobic amino acid residue of insulin and which binds to the insulin binding site of the insulin receptor, wherein said compound is an insulin antagonist.

20. A method according to claim 19, wherein the ionic amino acid residue is selected from the group consisting of: A21 Asn, B21 Glu and A17 Glu.

21. A method according to claim 19, wherein the ionic and hydrophobic amino acid residue(s) is(are) selected from the group consisting of: A21 Asn, B21 Glu, A17 Glu, B24 Phe, B25 Phe, A19 Tyr, B12 Val, B16 Tyr, A2 Ile, A3 Val and A1 Gly.

22. A method according to claim 19, wherein at least one amino acid is selected from the group consisting of: A17 Glu, B21 Glu and A21 Asn; and at least one amino acid is selected from the group consisting of: B24 Phe, B25 Phe, A19 Tyr, B12 Val and B16 Tyr.

23. A method according to claim 19, wherein the non-peptidyl compound possesses ionic and hydrophobic chemical moieties spatially located so as to mimic ionic and hydrophobic residues associated with at least one of the following groups of amino acid residues:

(i.) A21 Asn, B21 Glu, A17 Glu, B24 Phe, B25 Phe;
(ii.) A21 Asn, B21 Glu, B24 Phe, B25 Phe;
(iii.) A21 Asn, B21 Glu, B24 Phe, B25 Phe, A1 Gly, A2 Ile, A3 Val;
(iv.) A21 Asn, B21 Glu, A17 Glu, A19 Tyr, A1 Gly, A2 Ile, A3 Val;
(v.) A21 Asn, B21 Glu, A17 Glu, B12 Val, A1 Gly, A2 Ile, A3 Val;
(vi.) A21 Asn, B21 Glu, B12 Val, A1 Gly, A2 Ile, A3 Val;
(vii.) A21 Asn, B21 Glu, A17 Glu, B16 Tyr, A1 Gly, A2 Ile, A3 Val;
(viii.) A21 Asn, B21 Glu, A17 Glu, A19 Tyr, B12 Val, B16 Tyr;
(ix.) A21 Asn, B21 Glu, A19 Tyr, B12 Val, B16 Tyr;
(x.) A21 Asn, B21 Glu, A17 Glu, B24 Phe, B25 Phe, A19 Tyr, B12 Val, B16 Tyr;
(xi.) A21 Asn, B21 Glu, B24 Phe, B25 Phe, A19 Tyr, B12 Val, B16 Tyr;
(xii.) A21 Asn, B21 Glu, B24 Phe, B25 Phe, B12 Val, B16 Tyr;
(xiii.) A21 Asn, B21 Glu, A17 Glu, B24 Phe, B25 Phe, A19 Tyr;
(xiv.) A21 Asn, B21 Glu, B24 Phe, B25 Phe, A19 Tyr;
(xv.) A21 Asn, A17 Glu, B24 Phe, B25 Phe, A19 Tyr;
(xvi.) B21 Glu, A17 Glu, B24 Phe, B25 Phe, A19 Tyr;
(xvii.) A21 Asn, B21 Glu, A17 Glu, B24 Phe, B25 Phe, B12 Val;
(xviii.) A21 Asn, B21 Glu, B24 Phe, B25 Phe, B12 Val;
(xix.) A21 Asn, A17 Glu, B24 Phe, B25 Phe, B12 Val;
(xx.) B21 Glu, A17 Glu, B24 Phe, B25 Phe, B12 Val;
(xxi.) A21 Asn, B21 Glu, A17 Glu, B24 Phe, B25 Phe, B16 Tyr;
(xxii.) A21 Asn, B21 Glu, B24 Phe, B25 Phe, B16 Tyr;
(xxiii.) A21 Asn, A17 Glu, B24 Phe, B25 Phe, B16 Tyr;
(xxiv.) B21 Glu, A17 Glu, B24 Phe, B25 Phe, B16 Tyr;
(xxv.) A21 Asn, B21 Glu, A17 Glu, B24 Phe, A19 Tyr, B12 Val, B16 Tyr;
(xxvi.) A21 Asn, B21 Glu, B24 Phe, A19 Tyr, B12 Val, B16 Tyr;
(xxvii.) A21 Asn, A17 Glu, B24 Phe, A19 Tyr, B12 Val, B16 Tyr;
(xxviii.) B21 Glu, A17 Glu, B24 Phe, A19 Tyr, B12 Val, B16 Tyr;
(xxix.) A21 Asn, B21 Glu, A17 Glu, B25 Phe, A19 Tyr, B12 Val, B16 Tyr;
(xxx.) A21 Asn, B21 Glu, B25 Phe, A19 Tyr, B12 Val, B16 Tyr;
(xxxi.) A21 Asn, A17 Glu, B25 Phe, A19 Tyr, B12 Val, B16 Tyr; and
(xxxii.) B21 Glu, A17 Glu, B25 Phe, A19 Tyr, B12 Val.

24. A method according to claim 19, wherein the non-peptidyl compound has the following formula:

$$AXYXZ_n \qquad \text{(formula 1)}$$

where A is W or VXW;

V is $V_1$ or $V_2$;

V is substituted with up to two X groups;

$V_1$ is a phenyl or 6 membered heteroaromatic ring, optionally substituted with up to 5 $R_1$ groups;

$V_2$ is a 5 member ring system which may incorporate up to 4 hetero atoms which may be independently a nitrogen atom, a nitrogen atom optionally substituted with $R_2$, oxygen or sulfur, the ring system being optionally substituted with up to 4 $R_1$ groups;

W is $W_1$ or $W_2$ or $W_3$;

W is substituted with up to two X groups;

$W_1$ is $V_1$;

$W_2$ is a fused bicyclic ring system comprising rings of 5 or 6 atoms, which may incorporate up to 4 hetero atoms, which may be independently a nitrogen atom, a nitrogen atom optionally substituted with $R_2$, oxygen or sulfur, the system being optionally substituted with up to seven $R_1$ groups;

$W_3$ is $-N(R_2)R'_2$;

$R_1$ is independently H, OH, alkyl, alkenyl, alkynyl, alkoxy, alkanol, hydroxyalkoxy, haloalkyl, haloalkoxy, halogen, SH, thioalkyl, cyano (—CN), $N(R_2)R'_2$, phenyl, phenyl optionally substituted with up to five alkyl groups of 1 to 3 carbon atoms or up to five halogen atoms, benzyl, phenethyl, nitro, —COR$_3$, —R$_5$COR$_3$, —R$_5$SOR$_3$, —R$_5$SO$_2$R$_3$, —SO$_2$N(R$_2$)R'$_2$ or azido;

$R_2$ and $R'_2$ are independently H, alkyl of 1 to 6 carbon atoms, alkenyl of 3 to 6 carbon atoms, alkynyl of 3 to 6 carbons, hydroxyalkyl of 2 to 6 carbons, alkoxy of 2 to 6 carbons, haloalkyl, haloalkenyl, haloalkoxy, benzyl, benzyl optionally substituted with up to four $R_1$ groups, phenylethyl, phenylethyl optionally substituted with up to four $R_1$ groups, arylalkyl, and where $R_2$ and $R'_2$ can also be joined to form cyclic structures;

$R_3$ is independently H, OH, alkyl, alkenyl, alkynyl, alkoxy, alkanol, hydroxyalkoxy, —R$_4$N(R$_2$)R'$_2$, mesyl, triflouromesyl, —NHSO$_2$CH$_3$ or —NHSO$_2$CF$_3$;

$R_4$ is independently a bond, alkyl, alkenyl or alkynyl;

X is independently, a bond, —R$_4$N(R$_2$)R$_4$—, —R$_4$N=NR$_4$—, —R$_4$N(R$_2$)—N(R$_2$)R$_4$—, —R$_4$OR$_4$, —R₄SR₄—, —R₅—, —R₅O—, —R₅S—, —R₅N(R₂)—, —SO—, sulfonyl (—SO₂—), —CO—, —CONH—, —NHCONH—, —NHCO—, —CONHCO—, —CON(R₂)—, —R₅COR₅—, —R₅COR₅N(R₂)R₅—, —N(R₂)CO— or —R₄N(R₂)R₄COR₄—;

R₅ is independently alkyl, alkenyl, alkynyl, alkoxy, alkanol, hydroxyalkoxy;

Y is either Y₁, Y₂ or Y₃;

Y is substituted with at least two, but optionally up to four X linking groups;

Y₁ is a fused bicyclic ring system comprising rings of 5 or 6 atoms which may incorporate up to 4 hetero atoms, which may be independently a nitrogen atom, a nitrogen atom optionally substituted with R₂, oxygen or sulfur, the ring system optionally independently incorporating a sulfoxide (SO), sulfone (SO₂) or carbonyl (CO) group and optionally up to seven R₁ groups;

Y₂ is a 6:6:6 or a 6:5:6 fused tricyclic system which may incorporate up to 4 hetero atoms which may be independently a nitrogen atom, a nitrogen atom optionally substituted with R₂, oxygen or sulfur, the ring system optionally independently incorporating a sulfoxide (SO), sulfone (SO₂) or carbonyl (CO) group, and the ring system being substituted with at least two, but optionally up to four X linking groups and optionally up to seven R₁ groups;

Y₃ is V₁;

Z is independently —R₆COOH, —R₆SO₃H, —R₆NO₂, —R₆SO₂H, —R₆SO₂NHR₂; —R₇SO₂NHCOR₄—N-trifluoromesylsulfonamidate, —OH, -2-yl-hydroxyethanoic acid (—CH(OH)COOH), -3-yl-2-hydroxypropanoic acid (—CH₂CH(OH)COOH)-2-yl-2-hydroxypropanoic acid (—CH(CH₃)(OH)COOH), -3-yl-2,3-dihydroxypropanoic acid (—CH(OH)CH(OH)COOH), -2-yl-2,3-dihydroxypropanoic acid (—C(CH₂(OH))(OH)COOH), -3-yl-2-hydroxypropan-3-one-1-oic acid (—COCH(OH)COOH, 2-yl-2-hydroxypropandioic acid (—C(COOH)(OH)COOH), -2-yl-propandioic acid (—C(COOH)(H)COOH), -4-yl-2-hydroxybutan-4-one-1-oic acid (—COCH₂CH(OH)COOH, 2-yl-2-hydroxybutan-1,4-dioic acid (—C(OH)(COOH)CH₂COOH), 3-yl-2-hydroxybutan-1,4-dioic acid (—CH(CH(OH)COOH)COOH), 5-yl-tetrazole,

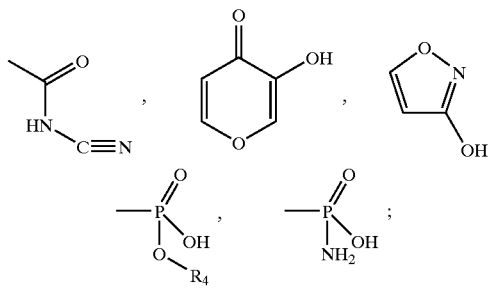

R₆ is independently a bond, alkyl, alkenyl, alkynyl, alkoxy, —CO(CH₂)ₙ—, where n is an integer between 0 and 4, alkanoic, alkenoic or alkynoic;

with the exception that where W₁ is an optionally substituted phenyl then Y₃ cannot be an optionally substituted phenyl.

25. A method according to claim 24, wherein the non-peptidyl compound is a dimer or heterodimer wherein the compounds are joined through a X linking group by way of their V or W groups.

26. A method according to claim 24, wherein when V is V₁ or V₂, then:
V₁ is selected from the group consisting of, benzene, pyridine, pyridazine, pyrimidine, pyrazine and triazine and is optionally substituted with up to 5 R₁ groups; and V₂ is selected from the group consisting of, cyclopenta-1,3-diene, pyrrole, furan, thiophene, oxazole, isoxazole, pyrazole, imidazole, thiazole, isothiazole and triazole and is optionally substituted with up to 4 R₁ groups;

and W is W₂ then

W₂ is selected from the group consisting of naphthalene, quinoline, isoquinoline, phthalazine, naphthyridine, quinoxaline, quinazoline, cinnoline, pteridine, indole, benzothiophene, benzofuran, benzimidazole, indazole, benzoxazole, benzisooxazole, benzthiazole, benzisothiazole, purine, indoline and isoindoline and is optionally substituted with up to seven R₁ groups; and Y is either Y₁ or Y₂ then Y₁ is selected from the group consisting of croman, isochroman, benzofuran, cromene, 1,2,3,4-tetrahydronaphthalene, 1,4-dihydronaphthalene, indan, indene, benzopiperidine, indoline, isoindoline, quinoline, isoquinoline, phthalazine, naphthyridine, quinoxaline, quinazoline, cinnoline or pteridine, coumarin and 2,3-dihydrocoumarin and is optionally substituted with up to seven R₁ groups; and Y₂ is selected from the group consisting of 9H-xanthone, 9H-xanthene, phenoxathiin, phenoxathiin-10-oxide, phenoxathiin-10-dioxide, acridine, phenazine, phenothiazine, phenoxazine, phenothiazine-5-oxide, phenothiazine-5-dioxide, thiathrene-5-dioxide, thiathrene-5-oxide, carbazole, dibenzo[b,d]furan and dibenzo[b,d]thiophene and is optionally substituted with up to seven R₁ groups.

27. A method according to claim 24, wherein when A is VXW then:
V is phenyl or pyrazole, optionally substituted with up to 5 R₁ groups;

and when A is W or VXW then W is W₁, W₂ or W₃ wherein W₁ is phenyl optionally substituted with up to 5 R₁ groups;

W₂ is naphthalene or quinoline optionally substituted with up to seven R₁ groups wherein R₁ is independently H, OH, methyl, ethyl, propyl, nitro, methoxy, ethoxy, 2-hydroxyethoxy, chloro, fluoro or acetyl;

W₃ is —N(R₂)R₂ wherein R₂ is propyl;

X is independently, a bond, methoxy (—OCH₂—), oxypropoxy (—O(CH₂)₃O—), hexenyloxy (—O-(CH₂)₄CH=CH—), sulfonyloxy (—SO₂—), methyl (—CH₂—), amidyl (—CONH—) or —NHCONH—;

and Y is either Y₁ or Y₂ then

Y₁ is croman, 4-H-chromen-4-one or napthalene optionally substituted with up to seven R₁ groups wherein R₁ is independently H, OH, methyl, ethyl, propyl, nitro, methoxy, ethoxy, 2-hydroxyethoxy, chloro, fluoro or acetyl;

Y₂ is 9H-xanthone optionally substituted with up to seven R₁ groups wherein R₁ is independently H, OH, methyl, ethyl, propyl, nitro, methoxy, ethoxy, 2-hydroxyethoxy, chloro, fluoro or acetyl;

Y₃ is phenyl optionally substituted with up to 5 R₁ groups wherein R₁ is independently H, OH, methyl, ethyl, propyl, nitro, methoxy, ethoxy, 2-hydroxyethoxy, chloro, fluoro or acetyl; and Z is independently —$R_6$COOH, —$R_6$SO$_3$H or —N-trifluoromesylsulfonamidate wherein $R_6$ is independently a bond or propyl.

28. A method according to claim 24, wherein the nonpeptidyl compound is selected from the following group of compounds:

(i.) 4,4'-Methylenebis[3-hydroxy-2-naphthalenecarboxylic acid];

(ii.) 7-[3-(4-acetyl-2-ethyl-5-hydroxyphenoxy)propoxy]-3,4-dihydro-8-propyl-2H-1-benzopyran-2-carboxylic acid;

(iii.) 2,4-dichloro-6-(N-(trifluoromethanesulfonyl))sulfamoylphenyl 3,5-dichloro-2-hydroxybenzenesulfonate;

(iv.) 7-[(4-acetyl-3-hydroxy-2-propylphenyl)methoxy]-4-oxo-8-propyl4H-1-benzopyran-2-carboxylic acid;

(v.) 7-[3-(4-acetyl-3-methoxy-2-propylphenoxy)propoxy]-3,4dihydro-8-propyl-2H-1-benzopyran-2-carboxylic acid;

(vi.) 3,4-dihydro-8-propyl-7-[[3-[2-ethyl-5-hydroxy-4-(1H-pyrazol-3-yl)phenoxy]propyl]oxy]-2H-1-benzopyran-2-carboxylic acid;

(vii.) 3,4-dihydro-8-propyl-7-[[3-[2-ethyl-5-hydroxy-4-ethoxyphenoxy]propyl]oxy]-2H-1-benzopyran-2-carboxylic acid;

(viii.) 3-[4-[7-carboxy-9-oxo-3-[3-[2-ethyl-4-(4-fluorophenyl)-5-hydroxyphenoxy]propoxy]-9H-xanthene]]propanoic acid;

(ix.) 8-propyl-7-(quinol-2'-ylmethoxy)-3,4-dihydro-2H-1-benzopyran-2-carboxylic acid;

(x.) 7-(naphth-2'-ylmethoxy)-8-propyl-3,4-dihydro-2H-1-benzopyran-2-carboxylic acid;

(xi.) N-(trifluoromethanesulfonyl)-3,5-dinitro-4-(N',N'-dipropylamino)benzenesulfonamide;

(xii.) 8-propyl-7-[3-[4-(4-fluorophenyl)-2-ethyl-5-hydroxyphenoxy]propoxy]-3,4-dihydro-2H-1-benzopyran-2-carboxylic acid; and (xiii.) 3,4-dihydro-7-[[6-(4-methoxyphenyl)hexenyl]oxy]-8-propyl-2H-1-benzopyran-2-carboxylic acid.

29. A method according to claim 24 wherein $V_1$ is selected from the group consisting of: benzene, pyridine, pyridazine, pyrimidine, pyrazine and triazine.

30. A method according to claim 24 wherein $V_2$ is selected from the group consisting of: cyclopenta-1,3-diene, pyrrole, furan, thiophene, oxazole, isoxazole, pyrazole, imidazole, thiazole, isothiazole and triazole, optionally substituted with up to 4 $R_1$ groups.

31. A method according to claim 24 wherein $W_2$ is selected from the group consisting of: naphthalene, quinoline, isoquinoline, phthalazine, naphthyridine, quinoxaline, quinazoline, cinnoline, pteridine, indole, benzothiophene, benzofuran, benzimidazole, indazole, benzoxazole, benzisooxazole, benzthiazole, benzisothiazole, purine, indoline and isoindoline.

32. A method according to claim 24 wherein $R_2$ and $R'_2$ are joined to form cyclic structures selected from the group consisting of: pyrrolidine, piperidine, hexahydro-1H-azepine, morpholine and piperazine.

33. A method according to claim 24 wherein $Y_1$ is selected from the group consisting of: croman, isochroman, benzofuran, cromene, 1,2,3,4-tetrahydronaphthalene, 1,4-dihydronaphthalene, indan, indene, benzopiperidine, indoline, isoindoline, quinoline, isoquinoline, phthalazine, naphthyridine, quinoxaline, quinazoline, cinnoline or pteridine, coumarin and 2,3-dihydrocoumarin.

34. A method according to claim 24 wherein $Y_2$ is selected from the group consisting of: 9H-xanthone, 9H-xanthene, phenoxathiin, phenoxathiin-10-oxide, phenoxathiin-10-dioxide, acridine, phenazine, phenothiazine, phenoxazine, phenothiazine-5-oxide, phenothiazine-5-dioxide, thiathrene-5-dioxide, thiathrene-5-oxide, carbazolc, dibenzo[b,d]furan and dibenzo[b,d]thiophene.

* * * * *